(12) United States Patent
Khosla et al.

(10) Patent No.: US 7,680,601 B1
(45) Date of Patent: Mar. 16, 2010

(54) DESIGN OF POLYKETIDE SYNTHASE GENES

(75) Inventors: Chaitan Khosla, Palo Alto, CA (US); Ralph C. Reid, San Rafael, CA (US); Daniel V. Santi, San Francisco, CA (US); Michael A. Siani, San Francisco, CA (US)

(73) Assignee: Kosan Biosciences, Hayward, CA (US)

( * ) Notice: Subject to any disclaimer, the term of this patent is extended or adjusted under 35 U.S.C. 154(b) by 131 days.

(21) Appl. No.: 09/867,845

(22) Filed: May 29, 2001

Related U.S. Application Data

(60) Provisional application No. 60/207,331, filed on May 30, 2000, provisional application No. 60/237,382, filed on Oct. 4, 2000.

(51) Int. Cl.
*G01N 33/48* (2006.01)
*C12Q 1/68* (2006.01)
*C12P 19/62* (2006.01)
*C07H 21/02* (2006.01)

(52) U.S. Cl. .............................. 702/19; 702/20; 435/6; 435/76; 536/23.1; 536/23.2

(58) Field of Classification Search .................... 702/19, 702/20; 435/183, 76
See application file for complete search history.

(56) References Cited

U.S. PATENT DOCUMENTS

| | | | | |
|---|---|---|---|---|
| 5,672,491 | A | 9/1997 | Khosla et al. | 435/148 |
| 5,712,146 | A | 1/1998 | Khosla et al. | 435/252.35 |
| 5,824,513 | A | 10/1998 | Katz et al. | 435/76 |
| 5,962,290 | A | 10/1999 | Khosla et al. | 435/183 |
| 6,303,342 | B1 | 10/2001 | Julien et al. | |

FOREIGN PATENT DOCUMENTS

| | | |
|---|---|---|
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |
| WO | WO 99/03986 | 1/1999 |
| WO | WO 00/04865 | 2/2000 |
| WO | WO 00/24907 | 5/2000 |
| WO | WO 00/31247 | 6/2000 |
| WO | WO 00/44717 | 8/2000 |

OTHER PUBLICATIONS

McKusick, VA, Jun. 25, 1986 (printed on Jul. 22, 2005 from website <http://srs.sanger.ac.uk/srsbin/cgi-bin/wgetz?%5Bomim-ID:311010%5D+-e>.*
Gokhale et al., Science (1999) 284:482-485.
Nicolaou et al., Angew. Chem. Int. Ed. (1998) 37:2014-2045.
Ranganathan et al., Chemistry & Biology (1999) 6:731-741.
Khosla, C. et al. (1996) *Trends in Biotechnology* 14(9):335-341.
Siani, M.A. et al. (1994) *J Chem Inf Comput Sci* 54:588-593.
Siani, M.A. et al. (2000) *J of Molecular Graphics and Modelling* 18(4-5):497-511.
Xue, Q. et al. (1999) *PNAS USA* 96(21):11740-11745.
Marsden et al., Science (1998) 279:199-202.
Tang et al., Chemistry & Biology (Jan. 2000) 7:77-84.
Cane et al., Science (1998) 282:63.
Carreras and Santi, Curr. Opin. Biotech. (1998) 9:403-411.
Fu et al., Biochemistry (1994) 33:9321-9326.
Hutchinson, Curr. Opin. Microbiol. (1998) 1:319-329.
Kao et al., Science (1994) 265:509-512.
McDaniel et al., Science (1993) 262:1546-1555.
Rohr, Angew. Chem. Int. Ed. Engl. (1995) 34(8):881-888.

* cited by examiner

*Primary Examiner*—Shubo (Joe) Zhou
(74) *Attorney, Agent, or Firm*—Stephen C. D'Amico

(57) ABSTRACT

Methods for the computational analysis of polyketides and the computer-assisted design of PKS genes are facilitated by representing the structure of a polyketide and/or a PKS gene that encodes the PKS that produces the polyketide by alpha-numeric symbols that facilitates computer assisted analysis. A database of polyketides and corresponding PKS genes that can be rapidly searched and information extracted for a variety of applications, including the design and specification of PKS genes via the recombining of modules or portions of modules or sets of modules from already known and available PKS genes.

14 Claims, 45 Drawing Sheets

CHUCKLES: ADGJDD

SMILES:
C1(=O)-[C@H](C)[C@@H](OH)-[C@@H](C)[C@@H](OH)-
[C@@H](C)C-[C@@H](C)C(=O)-[C@H](C)[C@@H](C)-
[C@@H](C)[C@@H](CC)O1

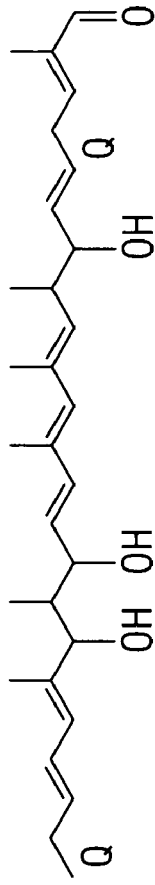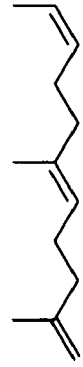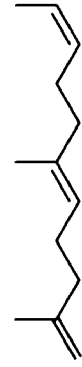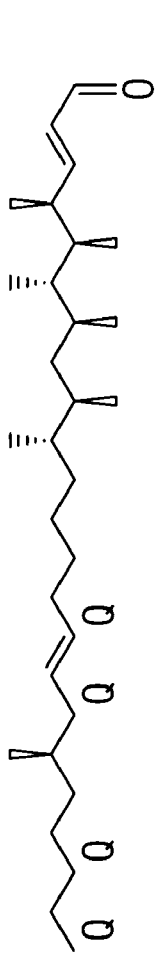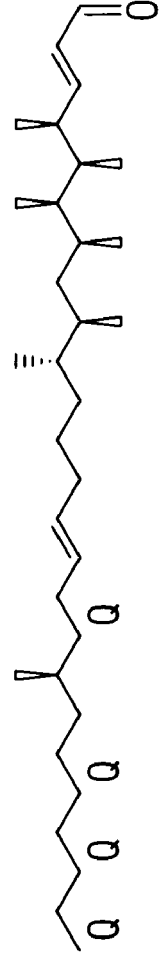
FIG. 6D boromycin fragment 2
ELaFKQ borophycin
FnLFgEKQ borrelidin
FnLFgEKQ calyculin
QFBBBMmNm candicidin
CDNNNNNNFCEELIEE

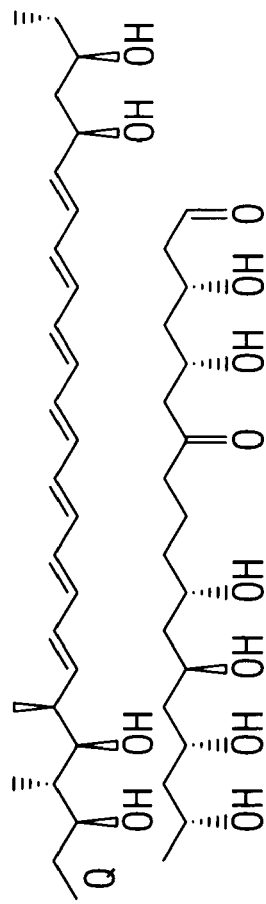
candidin
QDNNNNNNNFCEEFELIEE
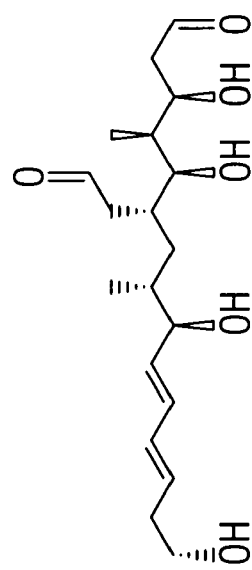
carbomycin
ENNCODF
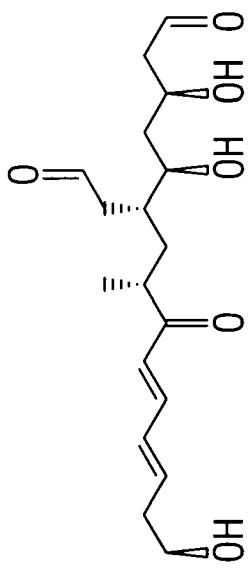
carbomycin B
FNNGOFF
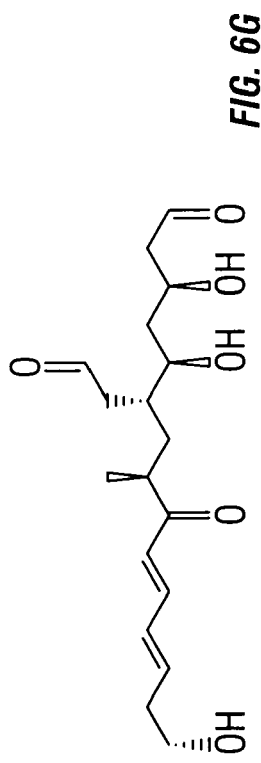
carbomycin A
ENNHOFF
FIG. 6G

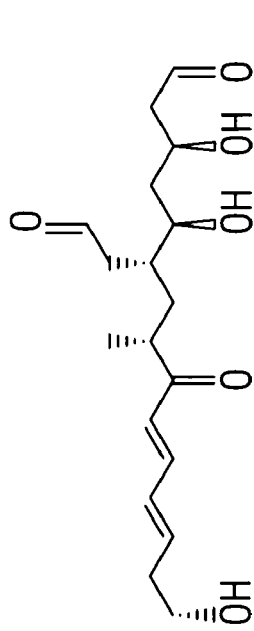
deltamycin Z
ENNGOFF
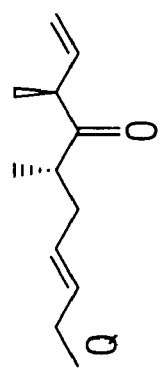
engleromycin
QNJHN
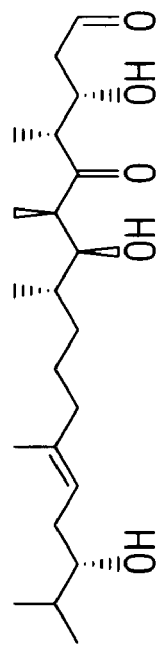
epothilone D
MEMLJDgE
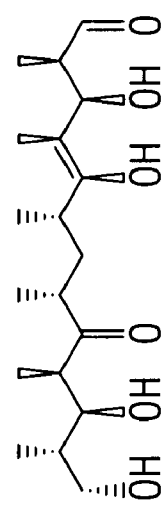
erthromycin
ADGJDD
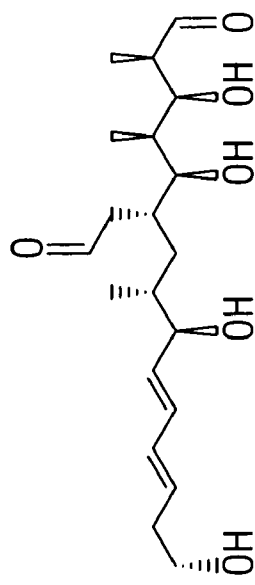
espinomycin A2
ENNCOFF
FIG. 6L

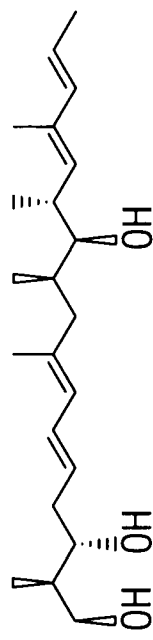
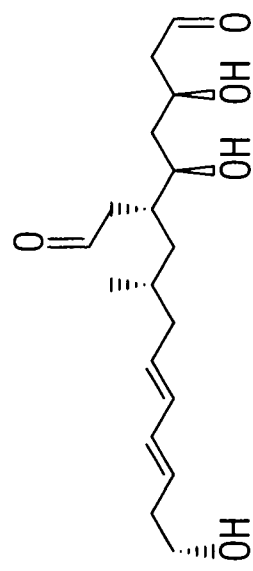
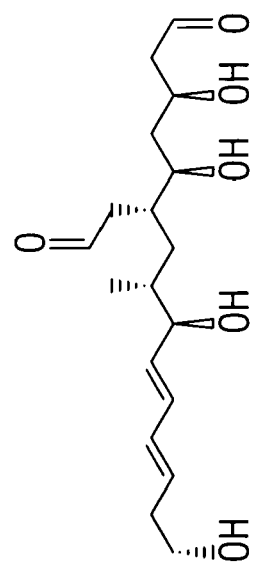
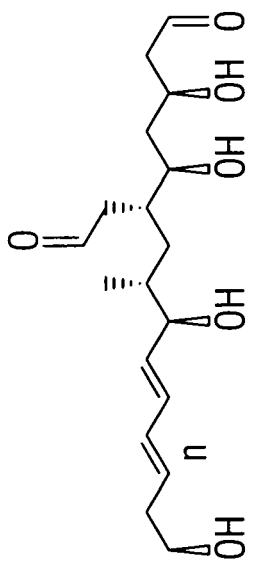
leucanicidin
CENMKCMN
leucomycin A3
ENNAOFF
leucomycin A5
ENNCOFF
leucomycin A12
FnNCOFF
FIG. 6R

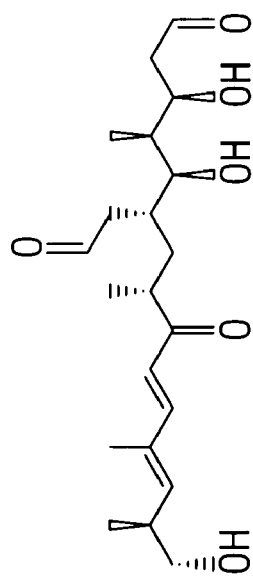
macrocin
BMNGODF
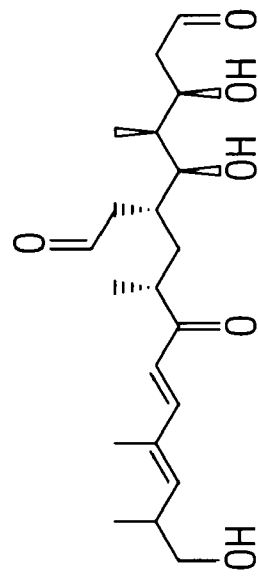
macrocin/YO07625
RMNGODF
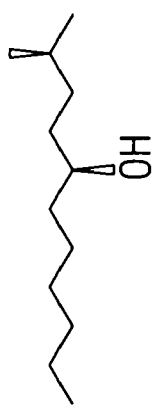
malyngolide
LLLFK
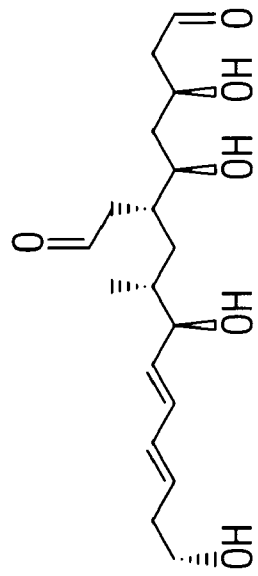
maridomycin
ENNCOFF
FIG. 6T

FIG. 6W mycolactone A
SRMJSMSSL mycolactone B
sSMNMMN myxovirescin A1
QEFLNNLLILKJ myxovirescin A2
QEFLNNLLILJJ myxovirescin B
QEFLNNLLILKM myxovirescin C
QEFLNNLLLLKJ

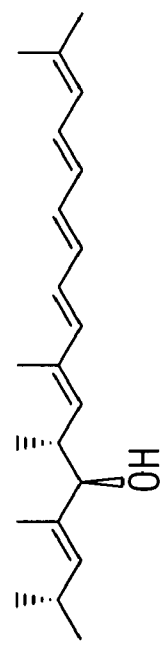
phenalamide C
JMCMNNNM
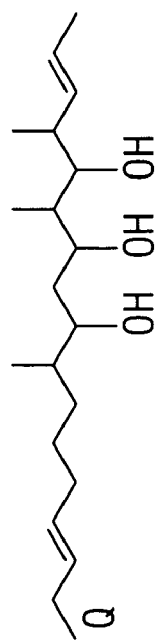
phthoramycin
QNLUSRRN
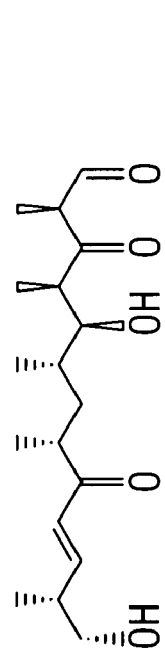
pikromycin
ANGJDH
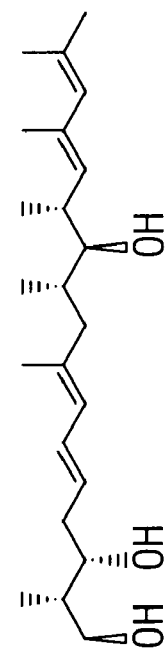
prasinon B
CENMJCMM
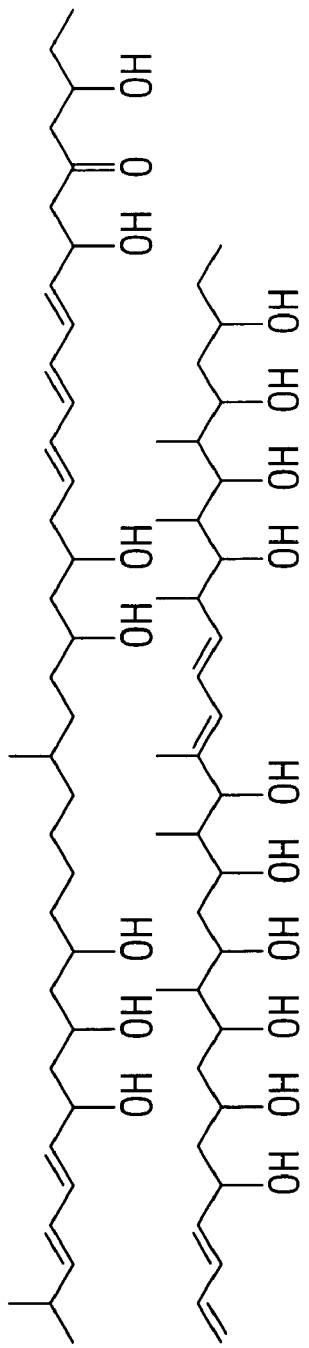
quinolidomicin
UNNSSSLULSSNWNSIS
NNSSSUSRR=L=URRSS
FIG. 6AC

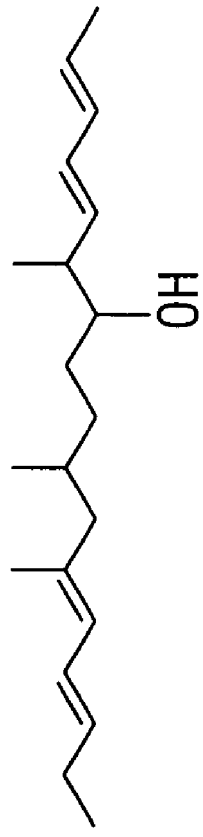
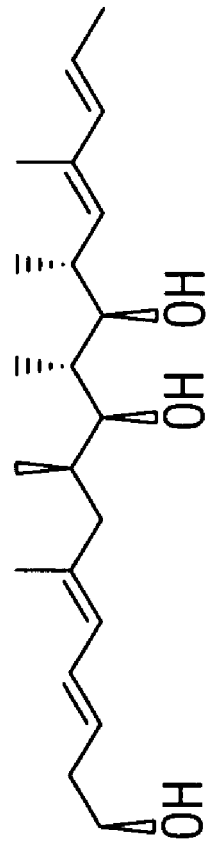
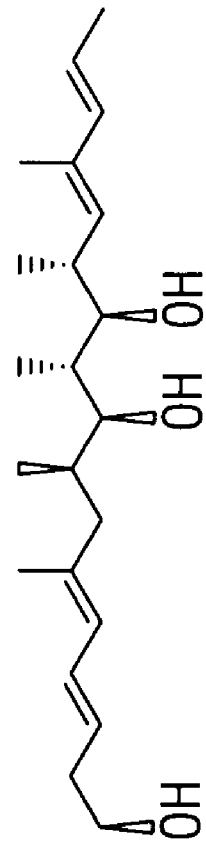
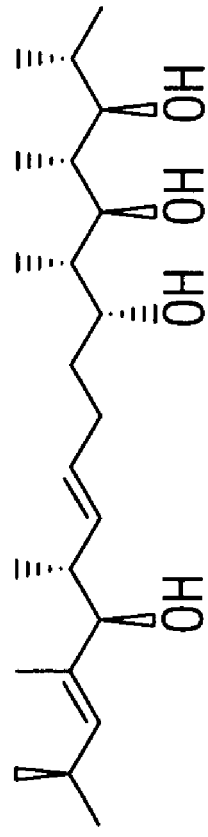
vicenistatin
LNMULRNN
viranam

DESIGN OF POLYKETIDE SYNTHASE GENES

CROSS REFERENCE TO RELATED APPLICATIONS

This application asserts priority to U.S. Provisional Application Nos.: 60/237,382 filed Oct. 4, 2000 by inventor Daniel Santi entitled DEVELOPMENT AND SCREENING OF A VIRTUAL POLYKETIDE LIBRARY; and 60/207,331 filed May 30, 2000 by inventors Daniel Santi, Michael Siani and Chaitan Khosla entitled DESIGN OF POLYKETIDE SYNTHASE GENES, all of which are incorporated herein by reference.

CD APPENDIX

This disclosure includes a computer program listing appendix, containing appendix A, B, and D. Appendix C is submitted herewith as a paper copy, as FIGS. 6A-6AJ. The appendices A, B, C and D are incorporated herein by reference.

Appendix A, B, and D are contained on compact disc. The content of the following submission on compact disc is incorporated herein by reference in its entirety: A computer readable form (CRF) of Appendix A-20055.00, (file name: 020220_1044, date recorded: Jan. 28, 2002, size: 32,768 bytes); Appendix B-20055.00 (file name: 020220_1044, date recorded: Jan. 28, 2002, size: 38,912 bytes); and Appendix D-Morph-library (file name: 020220_1044, date recorded: Jan. 28, 2002, size: 16,384 bytes).

FIELD OF INVENTION

The present invention provides methods for the analysis of polyketides and the design of polyketide synthase genes. The invention relates to the fields of computational analysis, chemistry, molecular biology, and medicine.

BACKGROUND OF THE INVENTION

The class of compounds known as polyketides is a large family of diverse compounds synthesized primarily from 2-carbon unit building block compounds through a series of condensations and subsequent modifications. Polyketides occur in many types of organisms, including fungi and mycelial bacteria such as the actinomycetes. There are a wide variety of polyketide structures, and the class of polyketides encompasses numerous compounds with diverse activities. Epothilone, erythromycin, FK-506, FK-520, megalomicin, narbomycin, oleandomycin, picromycin, rapamycin, spinocyn, and tylosin are examples of such compounds.

Given the difficulty in producing polyketide compounds by traditional chemical methodology, and the typically low production of polyketides in wild type cells, there has been considerable interest in finding improved or alternate means to produce polyketide compounds. See PCT Publication Nos. WO 95/08548; WO 96/40968; WO 97/02358; and 98/27203; U.S. Pat. Nos. 5,962,290; 5,672,491; and 5,712,146; Fu et al., *Biochemistry* 33: 9321-9326 (1994); McDaniel et al, *Science* 262:1546-1555 (1993); and Rohr, *Angew. Chem. Int. Ed. Engl.* 34(8): 881-888 (1995), each of which is incorporated herein by reference.

Polyketides are synthesized in nature by polyketide synthase (PKS) enzymes. These enzymes, which are complexes of multiple large proteins, are similar to the synthases that catalyze condensation of 2-carbon unit building block compounds in the biosynthesis of fatty acids. The genes that encode PKS enzymes usually consist of three or more open reading frames (ORFs). Two major types of PKS enzymes are known that differ in their composition and mode of synthesis. These two major types of PKS enzymes are commonly referred to as Type I or "modular" and Type II or "iterative" PKS enzymes.

Modular PKSs produce many different polyketides, including a large number of 12-, 14-, and 16-membered macrolide antibiotics including erythromycin, megalomicin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D., The polyketide metabolites, E. Horwood, New York, 1991, which is incorporated herein by reference).

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al. *Science,* 265: 509-512 (1994), McDaniel et al., *Science* 262: 1546-1557 (1993), and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, *Saccharopolyspora erythraea,* allows more facile construction of recombinant PKSs, and reduces the complexity of PKS analysis by providing a "clean" host background. This system also expedited construction of a combinatorial modular polyketide library in Streptomyces (see PCT publication No. WO 98/49315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, *Curr. Opin. Microbiol.* 1: 319-329 (1998); Carreras and Santi, *Curr. Opin. Biotech.* 9: 403-411 (1998); and U.S. Pat. Nos. 5,962,290; 5,712,146; and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

Polyketides are assembled by polyketide synthases through successive condensations of activated coenzyme-A thioester monomers derived from small organic acids such as acetate, propionate, and butyrate. Active sites required for condensation include an acyltransferase (AT), acyl carrier protein (ACP), and beta-ketoacylsynthase (KS). Each condensation cycle results in a β-keto group that undergoes all, some, or none of a series of processing activities. Active sites that perform these reactions include a ketoreductase (KR), dehydratase (DH), and enoylreductase (ER). Thus, the absence of any beta-keto processing domain results in the presence of a ketone, a KR alone gives rise to a hydroxyl, a KR and DH result in an alkene, while a KR, DH, and ER combination leads to complete reduction to an alkane. After assembly of the polyketide chain, the molecule typically undergoes cyclization(s) and post-PKS modification (e.g. glycosylation, oxidation, acylation) to achieve the final active compound.

To illustrate the synthesis of a macrolide by a modular PKS (see Cane et al., *Science* 282: 63 (1998), incorporated herein by reference), one can refer to the PKS that produces the erythromycin polyketide (6-deoxyerythronolide B synthase or DEBS; see U.S. Pat. No. 5,824,513, incorporated herein by reference). In the modular DEBS PKS enzyme, the enzymatic steps for each round of condensation and reduction are encoded within a single "module" of the polypeptide (i.e., one distinct module for every condensation cycle). As shown in FIG. 1, DEBS consists of a loading module and 6 extender modules and a chain terminating thioesterase (TE) domain within three extremely large polypeptides encoded by three open reading frames (ORFs, designated eryAI, eryAII, and eryAIII).

Each of the three polypeptide subunits of DEBS (DEB1, DEBS2, and DEBS3 in FIG. 1) contains 2 extender modules. DEBS1 additionally contains the loading module, and DEBS3 contains the TE domain. Collectively, these proteins catalyze the condensation and appropriate reduction of one propionyl CoA starter unit and six methylmalonyl CoA extender units. Modules 1, 2, 5, and 6 contain KR domains; module 4 contains a complete set, KR/DH/ER, of reductive and dehydratase domains; and module 3 contains no functional reductive domain. Following the condensation and appropriate dehydration and reduction reactions, the enzyme bound intermediate is lactonized by the TE at the end of extender module 6 to form 6-dEB (compound 1 in FIG. 1).

More particularly, the loading module of DEBS consists of two domains, an acyl-transferase (AT) domain and an acyl carrier protein (ACP) domain. In other PKS enzymes, the loading module is not composed of an AT and an ACP but instead utilizes a partially inactivated KS, an AT, and an ACP. This partially inactivated KS is in most instances called $KS^Q$, where the superscript letter is the abbreviation for the amino acid, glutamine, that is present instead of a cysteine in the active site that is believed to be required for condensation activity. Although the $KS^Q$ domain lacks condensation activity, it retains decarboxylase activity. The AT domain of the loading module recognizes a particular acyl-CoA (propionyl for DEBS, which can also accept acetyl) and transfers it as a thiol ester to the ACP of the loading module. Concurrently, the AT on each of the extender modules recognizes a particular extender-CoA (methylmalonyl for DEBS) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS and a methylmalonyl ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain (various intermediates are shown in FIG. 1) is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a polyketone, from which the name polyketide arises. Commonly, however, additional enzymatic activities modify the beta keto group of the polyketide chain to which the two carbon unit has been added before the chain is transferred to the next module. Modules may contain additional enzymatic activities as well, such as methyl transferase domains, but there are no such additional activities in DEBS.

Once a polyketide chain traverses the final extender module of a modular PKS, it encounters the releasing domain or thioesterase found at the carboxyl end of most PKSs. Here, the polyketide is cleaved from the enzyme and cyclyzed. The resulting polyketide can be modified further by tailoring or modification enzymes; these enzymes add carbohydrate groups or methyl groups, or make other modifications, i.e., oxidation or reduction, on the polyketide core molecule. For example, the final steps in conversion of 6-dEB to erythromycin A include the actions of a number of modification enzymes, such as: C-6 hydroxylation, attachment of mycarose and desosamine sugars, C-12 hydroxylation (which produces erythromycin C), and conversion of mycarose to cladinose via O-methylation. These modifications in various combinations result in erythromycins A (compound 2 in FIG. 1), B, C, and D.

While the detailed understanding of the mechanisms by which PKS enzymes function and the development of methods for manipulating PKS genes have facilitated the creation of novel polyketides, there remain substantial impediments to the creation of novel polyketides by genetic engineering. One such impediment is the availability of PKS genes. Many polyketides are known but only a relatively small portion of the corresponding PKS genes have been cloned and are available for manipulation. Moreover, in many instances the producing organism for an interesting polyketide is obtainable only with great difficulty and expense, and techniques for its growth in the laboratory and production of the polyketide it produces are unknown or difficult or time-consuming to practice. Also, even if the PKS genes for a desired polyketide have been cloned, those genes may not serve to drive the level of production desired in a particular host cell.

If there were a method to produce a desired polyketide without having to access the genes that encode the PKS that produces the polyketide, then many of these difficulties could be ameliorated or avoided altogether. The present invention meets this need.

SUMMARY OF THE INVENTION

In one embodiment, the present invention provides methods for the computational analysis of polyketides and the computer-assisted design of PKS genes.

In a first aspect, the present invention provides a method for representing the structure of a polyketide and/or a PKS gene that encodes the PKS that produces the polyketide by alpha-numeric symbols that facilitates computer assisted analysis.

In a second aspect, the present invention provides a database of polyketides and corresponding PKS genes that can be rapidly searched and information extracted for a variety of applications. More particularly, this database can include, in one mode, all known polyketides; and in another mode, the polyketides, optionally including all intermediates, produced by all known PKS genes or a subset thereof.

In a third aspect, the present invention provides a method for predicting the structure of a PKS and its corresponding genes from the structure of a polyketide.

In a fourth aspect, the present invention provides a method for designing novel PKS genes capable of producing a desired polyketide. This aspect of the invention is directed to the design and specification of PKS genes via the recombining of modules or portions of modules or sets of modules from already known and available PKS genes. In one mode, all possible PKS genes encoding a desired polyketide from a set of genes in a database are generated. In another mode, only a subset of such possible PKS genes is generated based on one or more parameters selected by the user. More particularly, a rating system is provided to sort the PKS genes designed for a particular target polyketide based on any one or more of several criteria, including number of non-native module interfaces, number of non-native protein interfaces, and other parameters as more particularly described below or selected by the user.

In another embodiment, the present invention provides methods and reagents for preparing novel PKS genes that encode PKS enzymes that produce a desired polyketide.

In a first aspect, the present invention provides a library of recombinant DNA compounds, wherein each member of said library encodes a module of a PKS or portions of modules or sets of modules having a desired specificity, and the library as a whole encompasses all of the members of a desired class of specificities.

In a second aspect, the present invention provides a method for assembling a PKS gene cluster that encodes a PKS that produces a desired polyketide from known and available PKS genes other than the naturally occurring PKS genes that produce the polyketide in nature.

These and other embodiments, modes, and aspects of the invention are described in more detail in the following description, the examples, and claims set forth below.

BRIEF DESCRIPTION OF THE FIGURES

FIG. 4 is a flowchart and block flow diagram in five parts designated A-E, inclusive.

Flowchart

Flowchart FIG. 4A is further defined.

Flowchart FIG. 4B is further defined.

Flowchart FIG. 4C is further defined.

Flowchart FIG. 4B is further defined.

DETAILED DESCRIPTION OF THE INVENTION

Because polyketides synthesized by modular PKS genes are built by the enzymatically controlled addition of primarily 2-carbon unit monomers and, to a lesser extent, other more complex monomers, each polyketide may be represented as a string of 2-carbon unit and other monomers. These monomers represent the portion of the polyketide backbone structure as a result of the incorporation of various starter and extender units (malonate, methyl malonate, etc.) and the subsequent chemical reactions.

These reactions include:

(1) condensation reactions, of which there are three basic reactions: malonyl-CoA condensation and methylmalonyl-CoA condensation with the branched methyl having either R or S stereochemistry; and (2) reduction reactions, of which there are five basic reactions: no reduction (ketone preserved), keto-reduction (to yield a hydroxyl having either R or S stereochemistry), dehydration (trans double bond), and enoyl-reduction (to yield a methylene).

An illustrative set of the basic monomers that can be used to represent a polyketide structure (and their corresponding symbols) comprises:

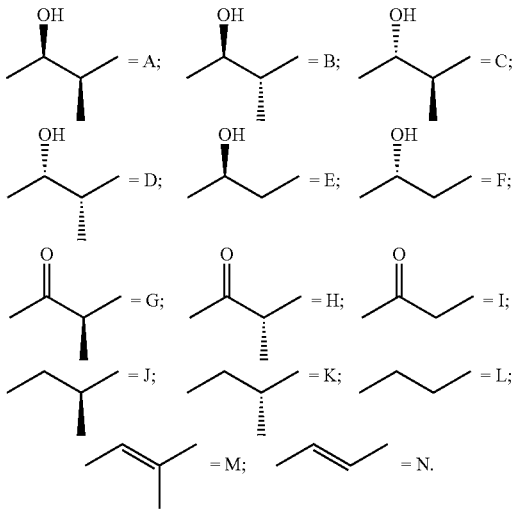

A miscellaneous monomer, Q, can be used to denote a portion of the polyketide structure that cannot be assigned by monomers A—N.

The monomer set shown above and in FIG. 2 does not represent the actual monomers incorporated during biosynthesis. Instead, these monomers include a carbon from two different biosynthetic monomers. This is best explained using a polyketide fragment depicted below.

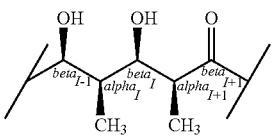

The fragment includes two two-carbon units, i and i+1 and part of a third two-carbon unit, i−1 that were incorporated into the polyketide during biosynthesis. The i-th extender module attaches the two carbon biosynthetic unit whose backbone carbons are designated as $alpha_i$ and $beta_i$ and the second extender module attaches the two carbon biosynthetic unit whose backbone carbons are designated as $alpha_{i+1}$ and $beta_{i+1}$. Using the monomer set shown above, this fragment consists of monomer A (derived from the beta carbon added in module i+1 and the alpha carbon added in module i) and another monomer A (derived from the beta carbon added in module i and the alpha carbon added in module i+1).

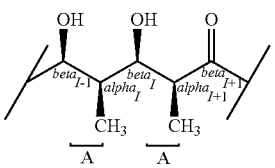

The fifth carbon designated $beta^{i+1}$ remains unassigned and will depend on the identity of the two-carbon biosynthetic unit that is incorporated in the polyketide by module i+2.

Figure 1:
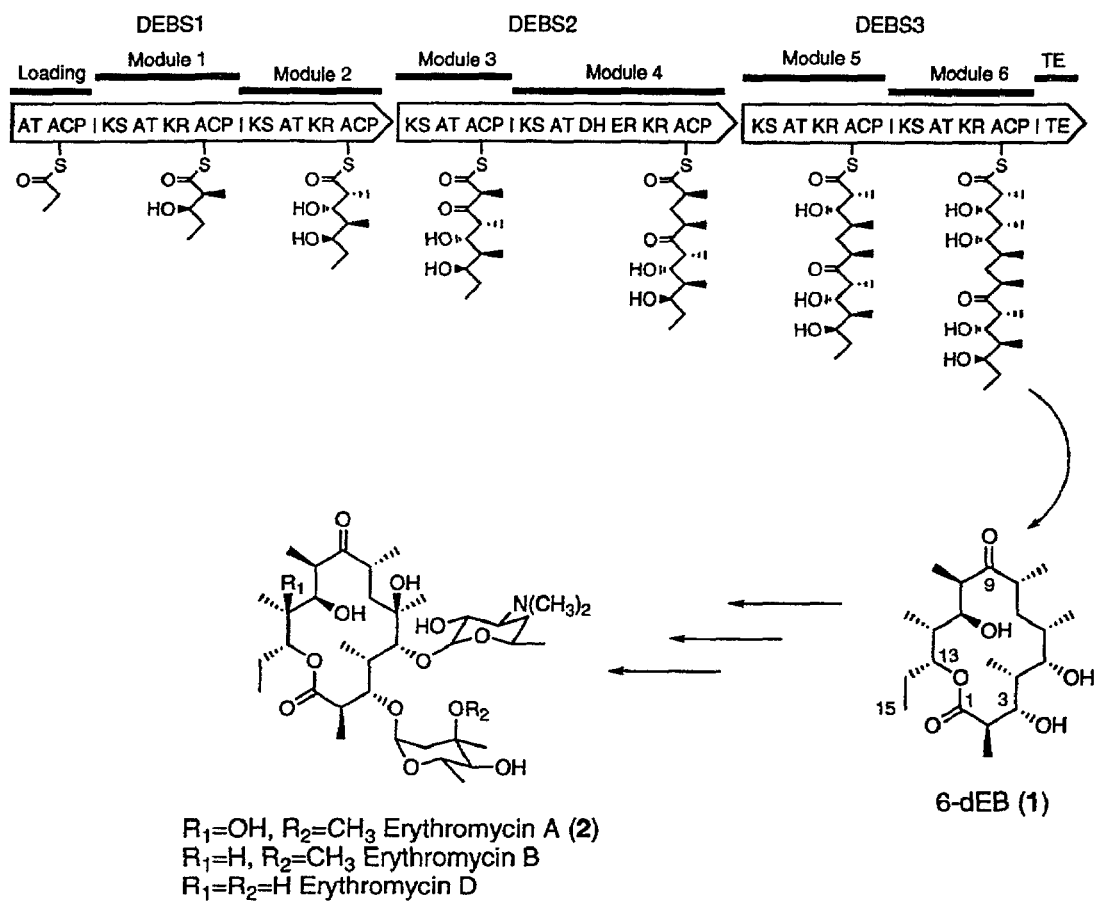
FIG. 1 shows a schematic representation of the PKS enzyme that synthesizes 6-deoxyerythronolide B (6-dEB, compound 1). The PKS is composed of three proteins, DEBS1, DEBS2, and DEBS3, each of which is represented by an arrow and contains two or more modules. Each module is represented by a solid line, and the domains in each module are shown inside the arrow. Various intermediates produced during the synthesis are also shown, as are the structures of erythromycins A (compound 2), B, and D resulting from modification of 6-dEB.
Figure 2:
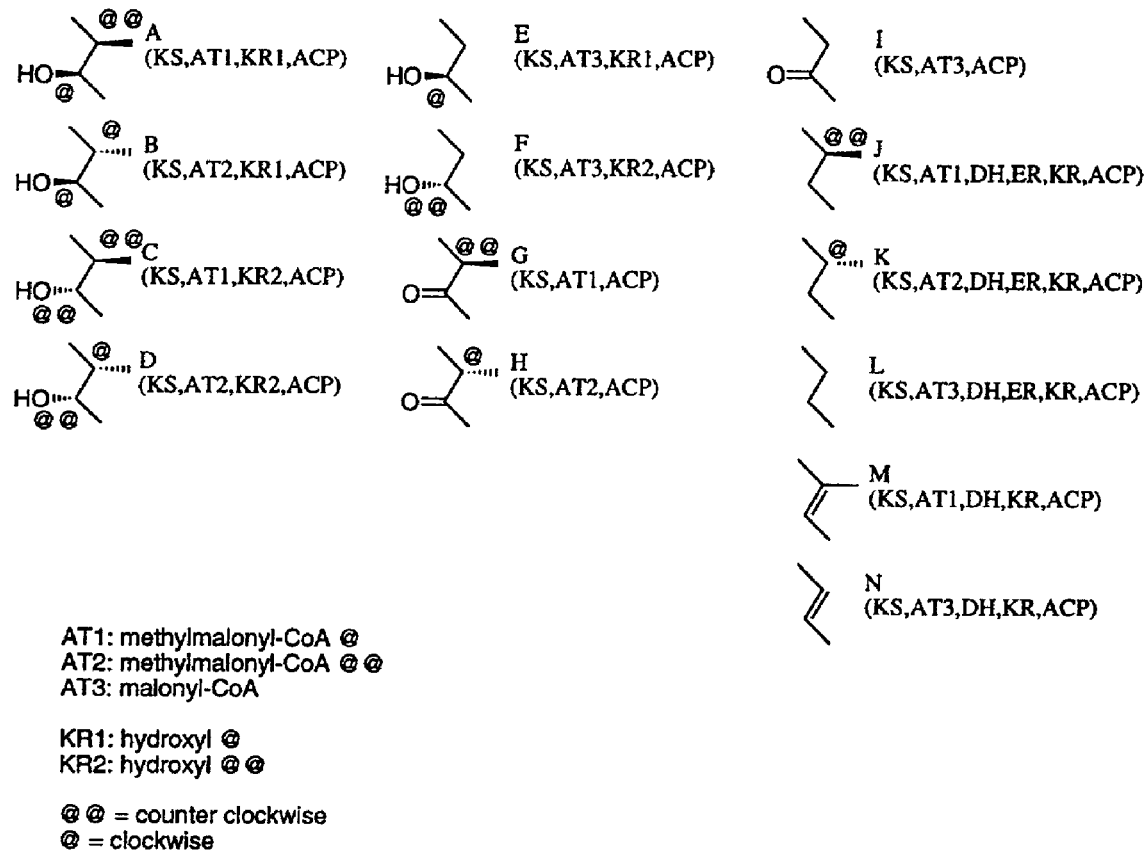
FIG. 2 shows an illustrative set of 2-carbon unit monomers present in macrocyclic polyketides; these monomers can be used to represent polyketide backbone diversity generated by commonly used starter and extender units (malonyl CoA and methylmalonyl CoA) and the condensation and reduction reactions mediated by PKS enzymes.

The set of monomers shown in FIG. 2 can be expanded to include other starter and extender units, of which there are many. Such starter and extender units include, for example but without limitation, hydroxymalonate (e.g., niddamycin), methoxymalonate (e.g. FK-520), ethylmalonate (e.g., FK-520), amino acids or amino acid derivatives that are incorporated into polyketides by the action of a non-ribosomal peptide synthase (e.g., thiazole in epothilone and pipecolate in rapamycin), or other units incorporated by, for example, an AMP ligase (e.g., the dihydroxycylohexyl moiety in rapamycin, FK-506, and FK-520) or a soluble CoA ligase. An illustrative set of additional starter and extender units includes:

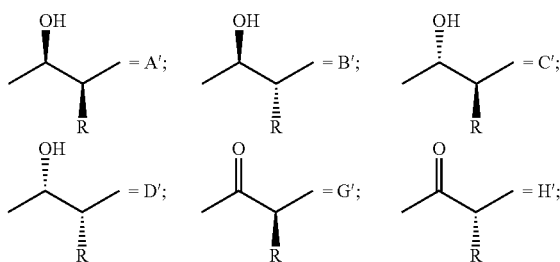

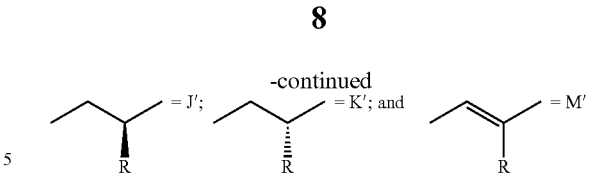

where R can be anything other than hydrogen or methyl (e.g., allyl, butyl, ethyl, hexyl, hydroxyl, isobutyl, and methoxy).

The set of monomers can also include post-PKS modifications, such as hydroxylation, methylation, epoxidation, glycosylation, or addition of intra-macrocyclic fused rings making the system polycyclic. Also, a variety of methods are known for the incorporation of unusual starter and or extender units in polyketide synthases (see, e.g., PCT Publication Nos. WO 97/02358; WO 99/03986; WO 98/01546; and WO 98/01571, each of which is incorporated herein by reference, and the monomer set can include such units.

By viewing polyketides as composed of sets of distinct monomers, one can in accordance with the present invention define a polyketide as a string of alpha-numeric symbols to facilitate computer analysis. In one method, a modified CHUCKLES methodology for representing polyketides is used. The CHUCKLES methodology (see Siani et al., "CHUCKLES: a method for representing and searching peptide and peptoid sequence," *J. Chem. Inf. Sci.* 34: 588-593 (1994) which is incorporated herein by reference) for representing peptides and related oligomers allows monomers to be strung together such that the molecular graph for the basic macrocycle can be generated from the string of monomers.

Figure 3:
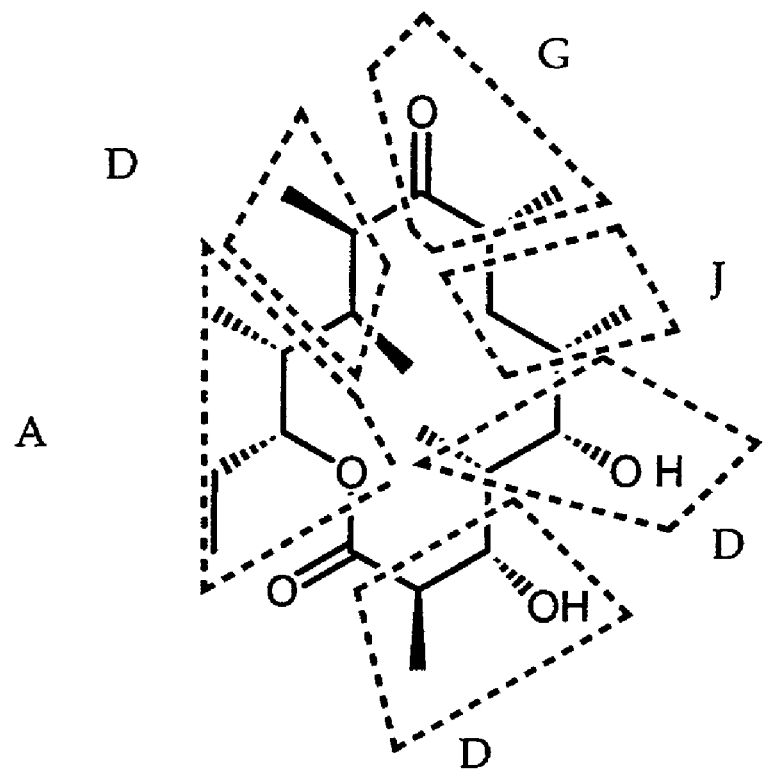
FIG. 3 shows a representation of 6-dEB by molecular graph, CHUCKLES notation, and SMILES notation. The CHUCKLES notation uses the 2-carbon unit monomers shown in FIG. 2. In the CHUCKLES notation, the order of attachment of monomers is designated by the order in which monomers are listed, and the attachment points within the monomers are specified in their definitions. In the SMILES notation, adjacent monomers are attached via single (covalent) bonds depicted by dashes. The cyclization bond is represented by the index 1 adjacent to the Start and Close monomers.

For example, using the set of monomers comprising A-N described above, the erythromycin macrocycle or 6-dEB can be represented as ADGJDD. This string of alphanumeric symbols is also referred to as the CHUCKLES string. FIG. 3 depicts the relationship between the CHUCKLES string, the SMILES string, and the actual molecular structure of 6-dEB. The CHUCKLES string for 6-dEB can be annotated to represent the structure of erythromycin A: A(1-lactone closure, 2-hydroxyl)DGJ(2-hydroxyl)D(1-glycosyl) D(1-glycosyl). Thus, ring closure (cyclization) and post-synthetic modifications (glycosylation and hydroxylation), and non-standard units where applicable (there are none in 6-dEB and erythromycin) are entered between parentheses after each monomer. Another example is an annotated CHUCKLES string for epothilone B: ME(1-lactone-closure)M(epoxide)LJDG(2-methylation)E. As above, cyclization, post-synthetic modifications (epoxide formation), and non-standard units (methyl at C-4) are entered between parentheses after each monomer.

In another aspect of the present invention, a database of polyketides is provided. In one aspect of the present invention, the polyketides are represented by a string of defined monomers. In one embodiment, the monomers are selected from a group consisting of:

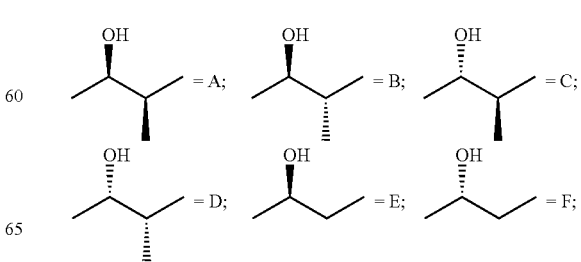

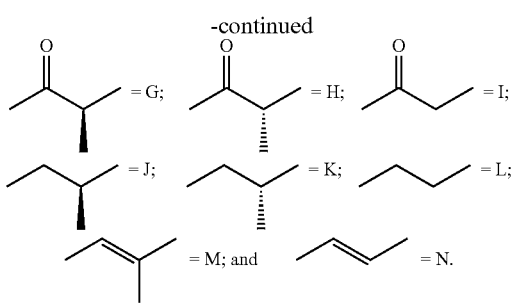

In another embodiment, polyketides are represented by the monomers A—N as well as additional monomers selected from the group consisting of

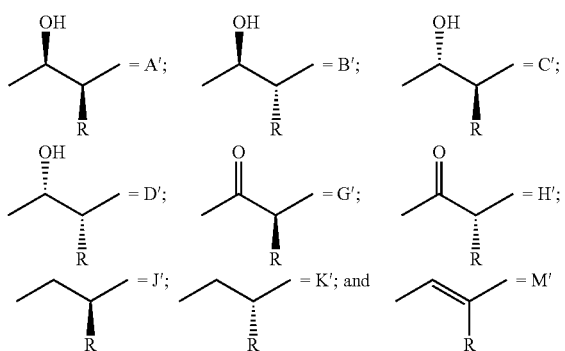

where R can be anything other than hydrogen or methyl.

The string of monomers can be represented as a linearized structure or as a string of symbols. For example, the erythromycin can be represented as its aglycone, 6-dEB, as

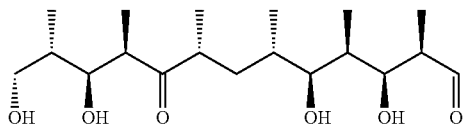

or as a string of symbols, ADGJDD. Optionally, the string of symbols can be annotated as "A(1-lactone closure,2-hydroxyl)DGJ(2-hydroxyl)D(1-glycosyl) D(1-glycosyl)" to more fully capture the erythromycin structure. This set of annotated strings is referred to as a "coded library" or a "coded" database of the present invention.

In an illustrative embodiment, the polyketide database consists of the polyketides described in current literature (Journal of Antibiotics (1981-present), Journal of Natural Products) and various databases (Chemical Abstracts CAPlus, Anti-Base). All unique macrocyclic polyketides are converted to the modified CHUCKLES format. Of the ~1000 novel polyketides obtained, only ~200 different strings of monomers and unique macrocycles are needed to represent the much larger collection of polyketides in the database, because many of the differences between the naturally-occurring polyketides are due to different glycosyl (sugar) groups attached at different positions on the macrocycle.

Thus, a macrocyclic polyketide can be converted to a string of 2-carbon monomers by mapping the monomers onto the polyketide. This can be performed manually or with computer assistance. First, any sugar moieties are conceptually removed by hydrolysis and any lactones (bond between the ketone and oxygen) are hydrolyzed thus generating a linearized structure of the backbone of the polyketide. Generally, this leaves a carboxy carbon at one end of the linear molecule and a hydroxyl at the other. The polyketide is then "sequenced" manually or in silico from the end containing the carboxy carbon, the end corresponding to the last monomer added by the PKS before synthesis is complete. This end serves as a convenient handle from which to start the mapping process. Although closing of the lactone often occurs between the two ends of the polyketide, this is not always the case. However, the last ketone added by the PKS is almost always involved in macrolactone formation and so serves as a more convenient handle than the hydroxyl for commencing sequencing.

The manual or in silico sequencing is performed by matching the monomers, one at a time, while traversing the macrocyclic backbone. First the carboxy carbon is skipped, and an attempt is made to match each of the monomers in the monomer set selected (i.e., monomer set A—N in FIG. 2) against the next two carbons in the macrocycle. The match takes into account carbon, oxygen, and no substitution at each backbone position, chirality at each backbone position, and bond order between the two backbone carbons.

If the sequencing is performed in silico, the method is referred to as back-translation and involves converting a molecular graph into a string of monomers. First, the monomer library is converted to SMARTS format. SMARTS is a superset of the SMILES language that specifies a pattern in a molecular graph (Daylight Software Manual: Theory; Daylight Chemical Information Systems; Irvine, Calif. 1993, incorporated herein by reference). SMARTS permits one to specify a variable number or a limit on the number of covalent bonds to non-hydrogen atoms from a particular atom. In contrast, SMILES assumes that the unspecified valences are hydrogens. For example, the SMILES string for monomer A is [C@@H](o)[C@H](C). The oxygen may be bonded to any other single atom; if the atom is not specified, it is assumed be a hydrogen. In the SMARTS string for monomer A, [C@@H](O;D2])[C@H]([CH3]), one can specify the exact number of hydrogens on some atoms (e.g., "CH3"). In addition, the "[O;D2]" indicates the oxygen is bonded to two (from D2) non-hydrogen atoms, in this case the first carbon and some other unspecified atom. This allows matching and distinction of post-modification moieties attached to the oxygen as well as additional cyclizations (six member rings can occur within the macrocycle; e.g., rapamcyin). Thus, the SMARTS notation allows pattern matching against the polyketide molecular graph.

When a match occurs, the atoms that match are tagged as part of a superset and labeled with the monomer name. Any atoms that are connected to the monomer that are not part of the macrocycle are tagged for identification as special precursor units (e.g., ethylmalonate instead of methyl malonate or malonate), or post-synthetic modification moieties (e.g., sugars, CCHO, hydroxylation, methylation). If all the atoms and bonds of the monomer cannot be identified, the monomer is given a designation to indicate the lack of identification (e.g., Q for question mark). These Q monomers can be used to identify monomers that are the site of post-PKS modifications that mask the function of the PKS module that generated that portion of the polyketide or that are not in the monomer set and so prevent the correlation of a particular segment of the backbone with one of the monomers in the monomer set.

Figure 5:
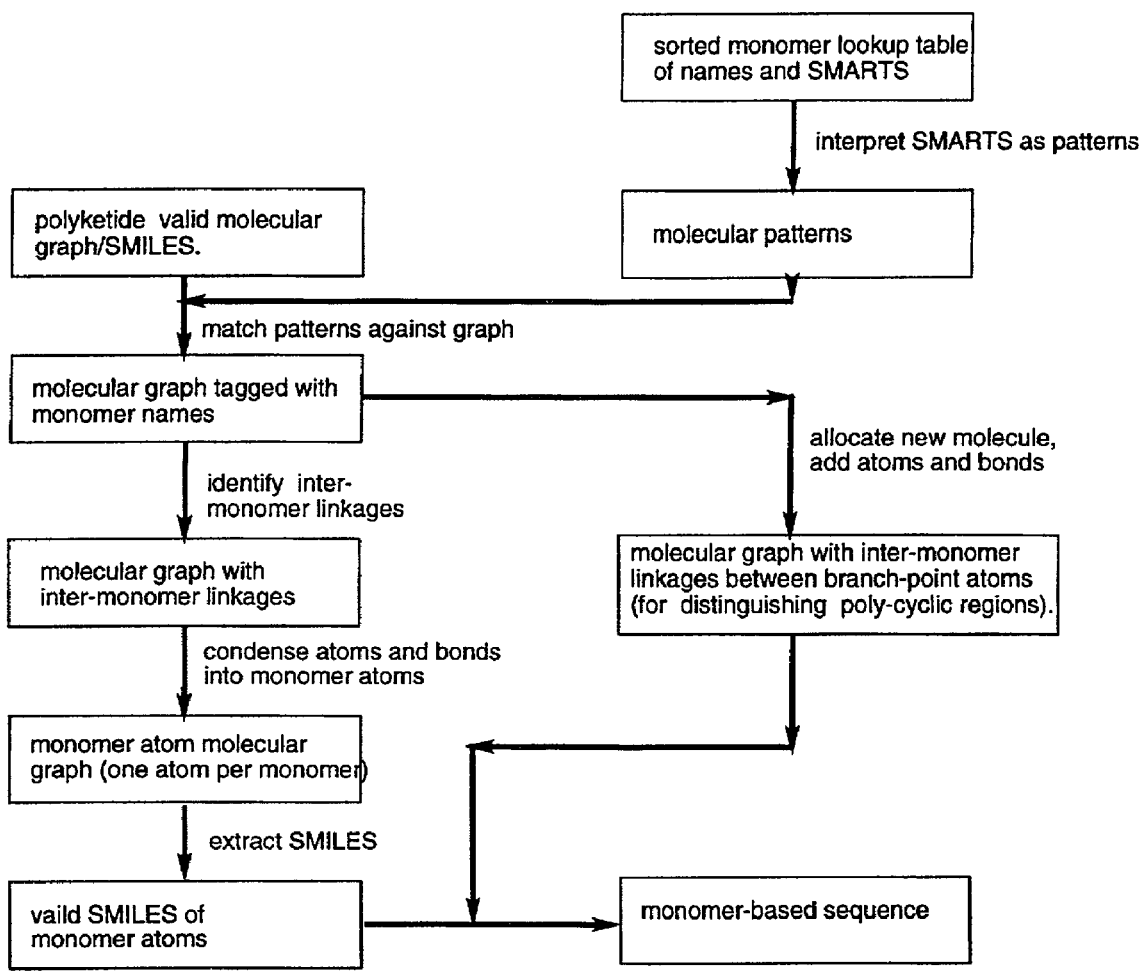
FIG. 5 shows a flowchart of a matching method for the generation of the CHUCKLES strings used for all polyketides in a library.
Figure 6A:
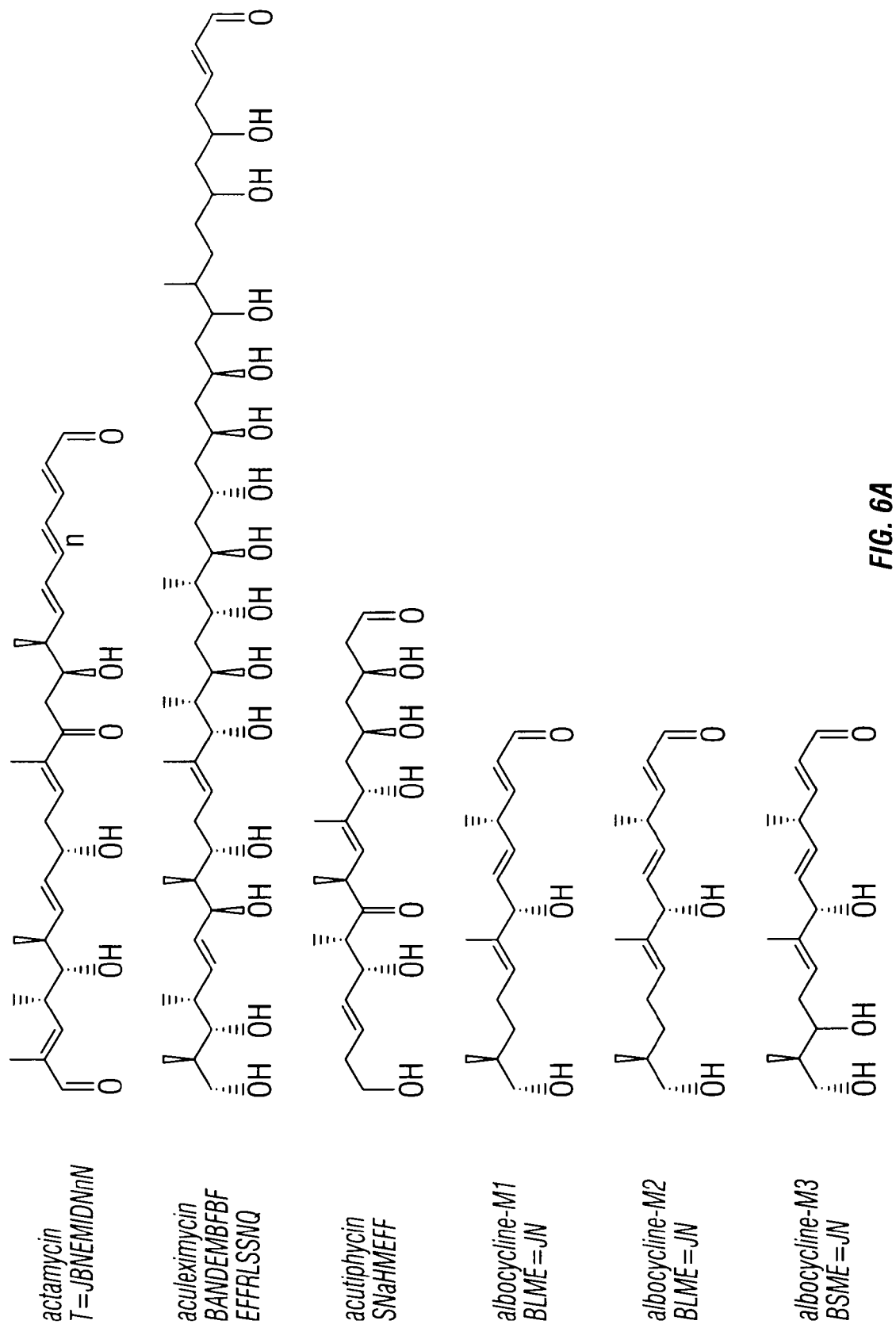
FIGS. 6A-6AJ show hieroglyphs under the compound names, which identify the string of PKS modules responsible for production of the compound.
Figure 6B:
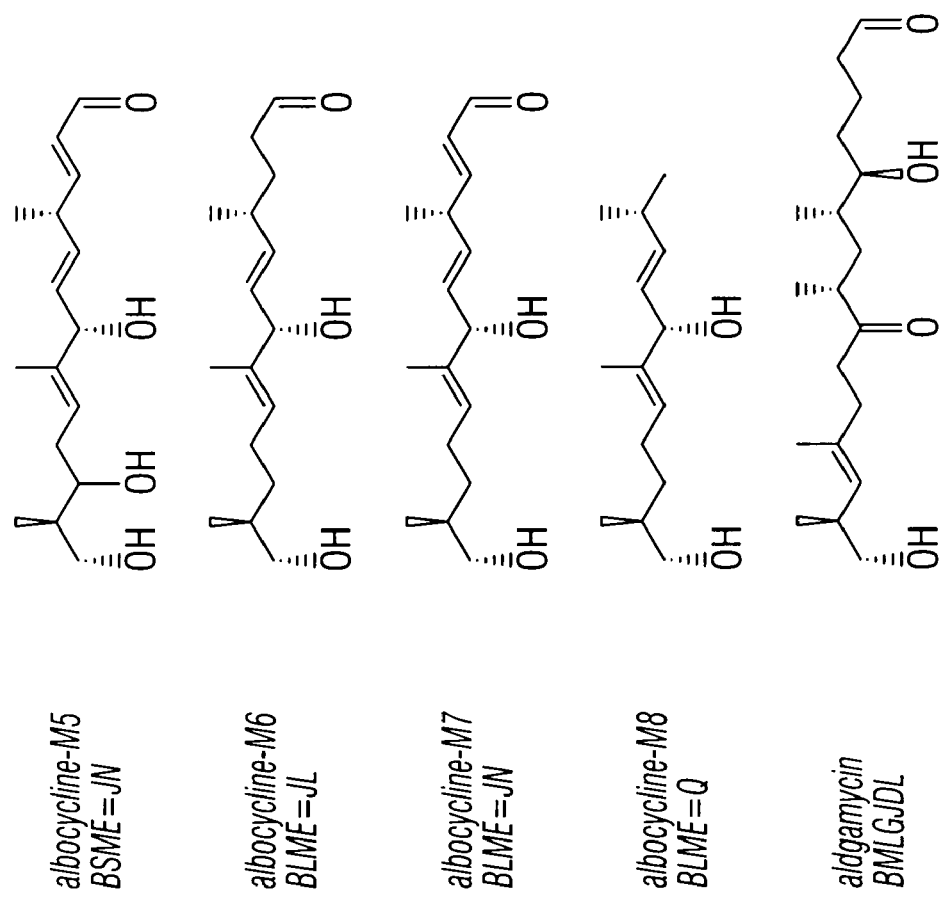
Figure 6C:
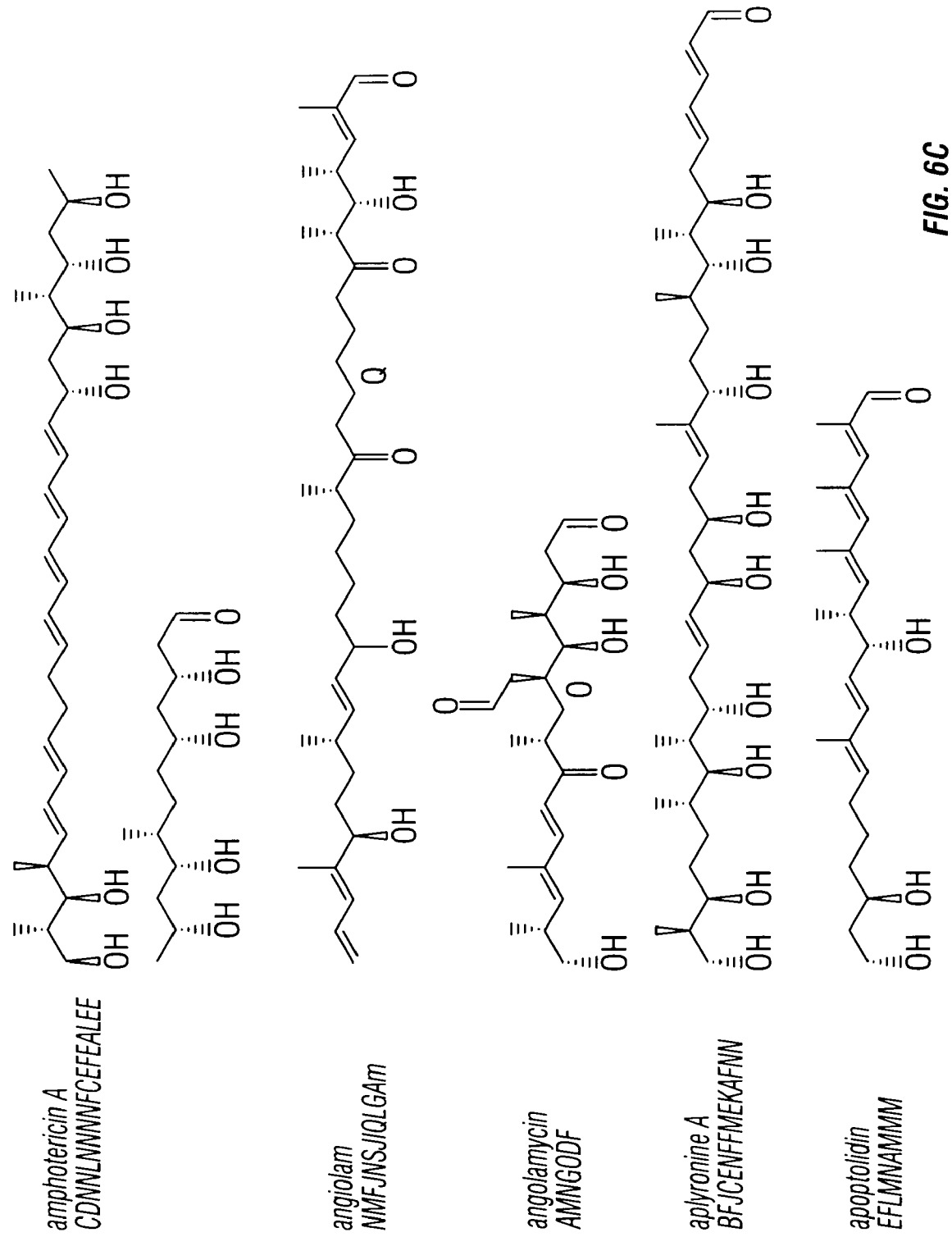
Figure 6E:
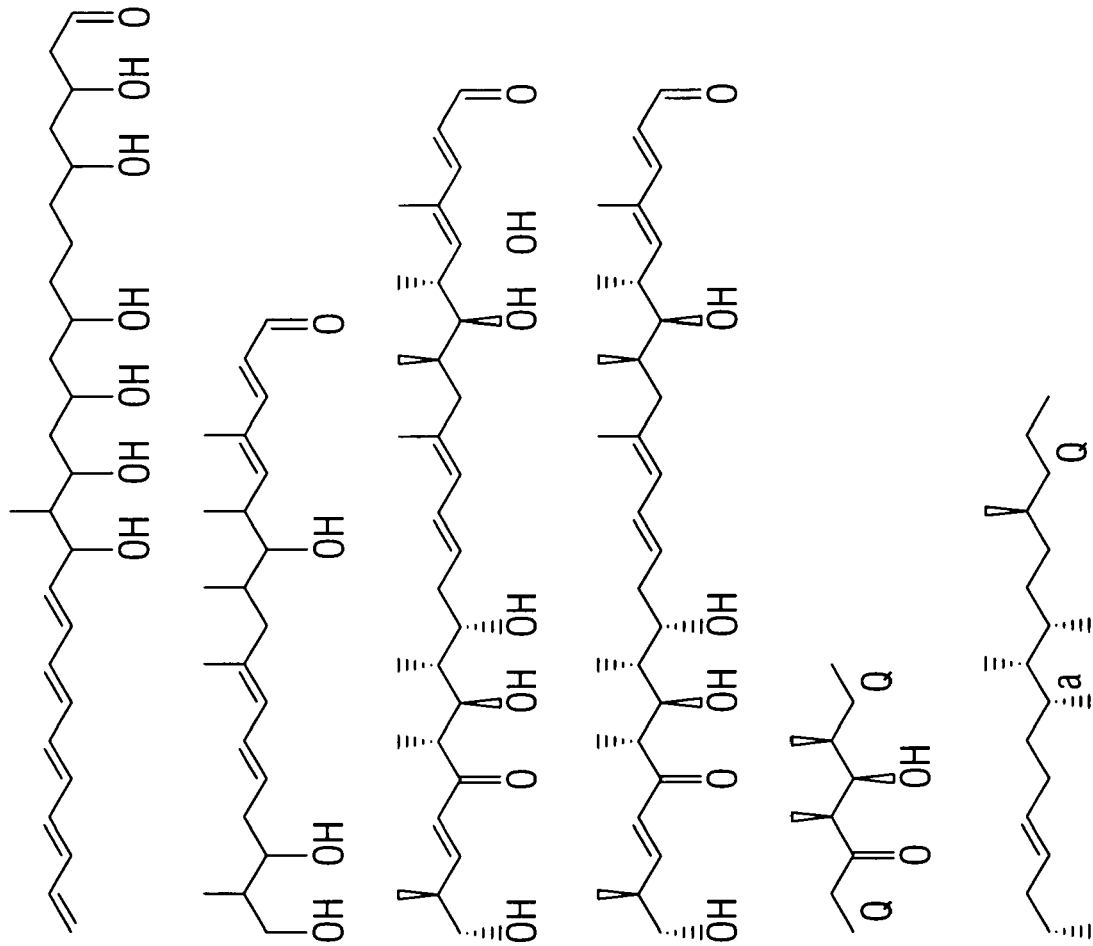
Figure 6F:
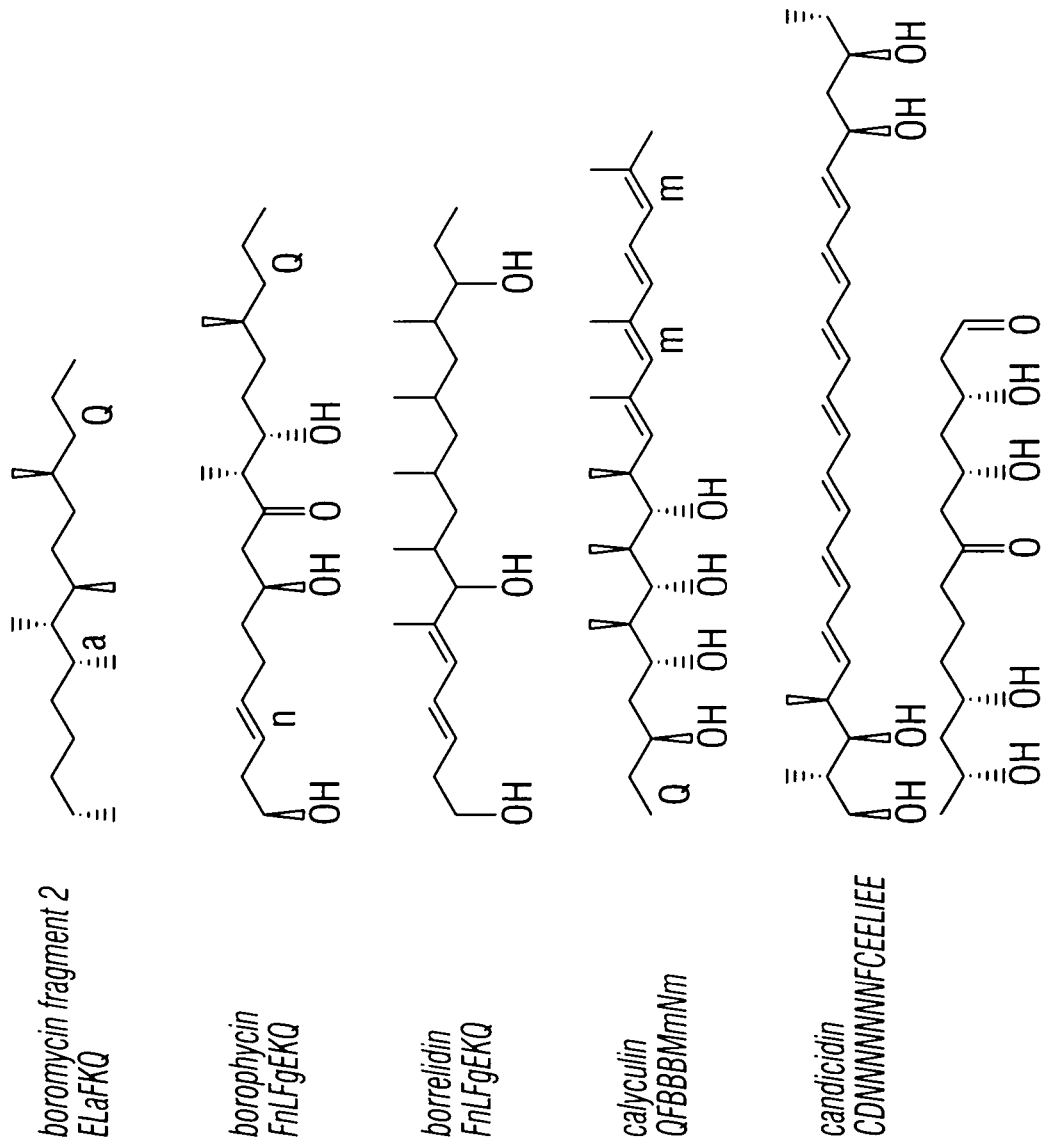
Figure 6H:
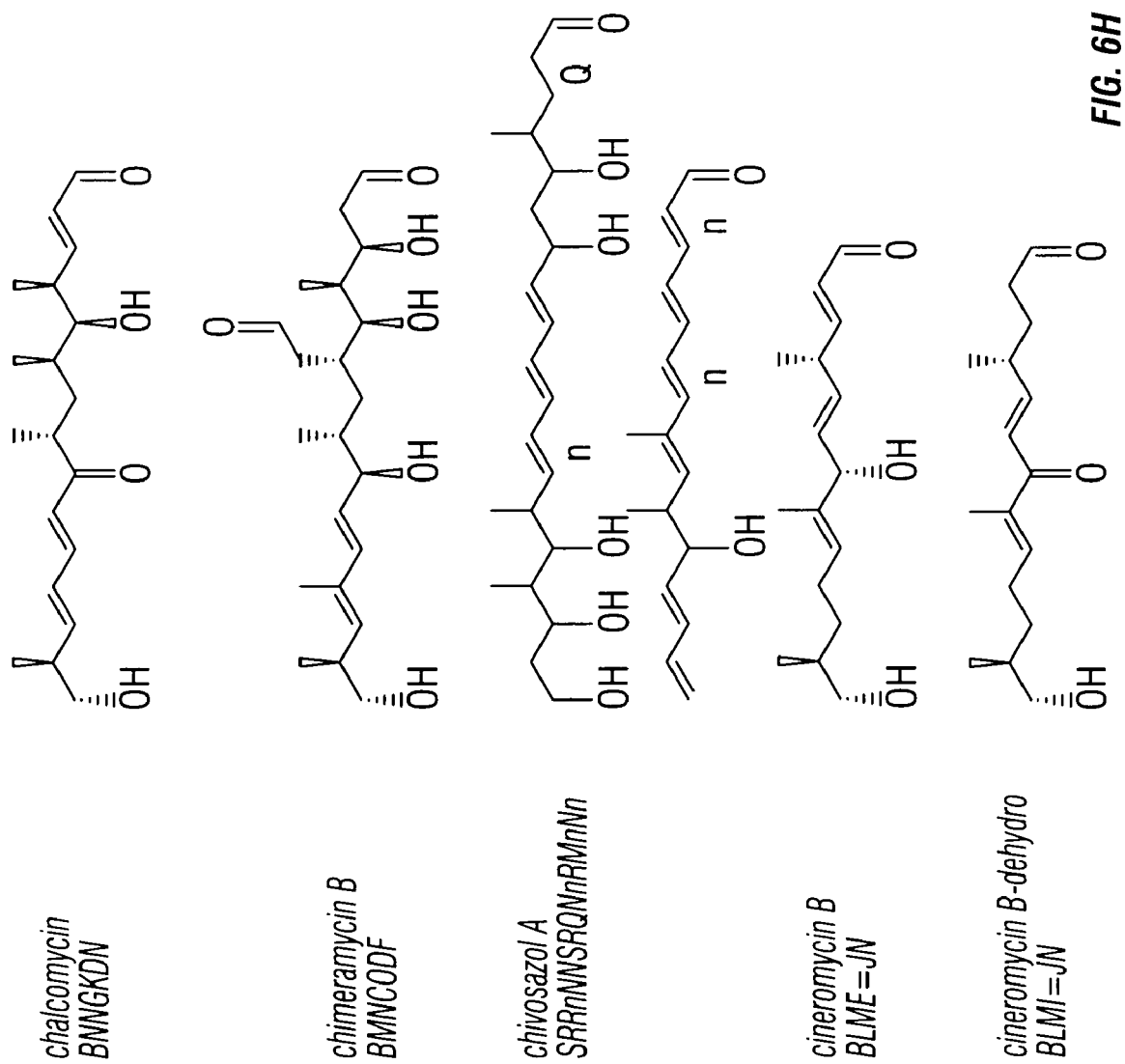
Figure 6I:
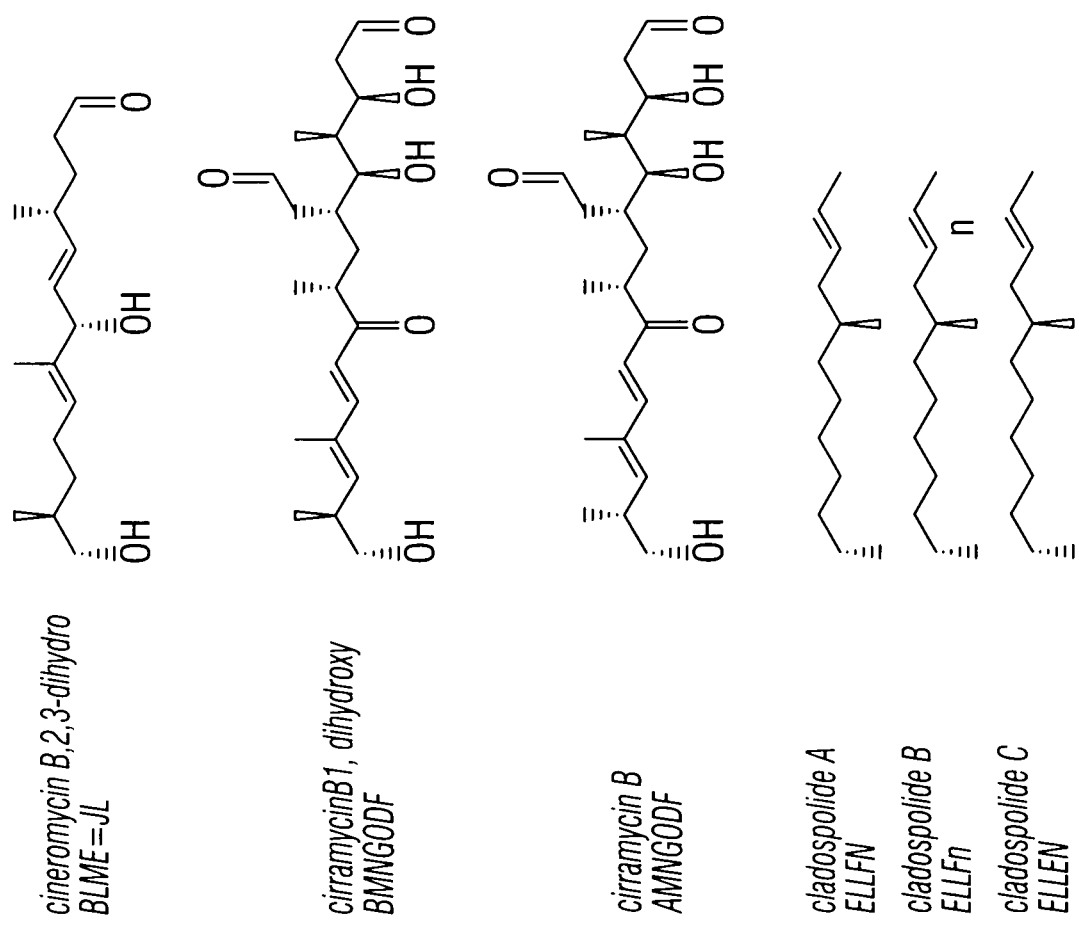
Figure 6J:
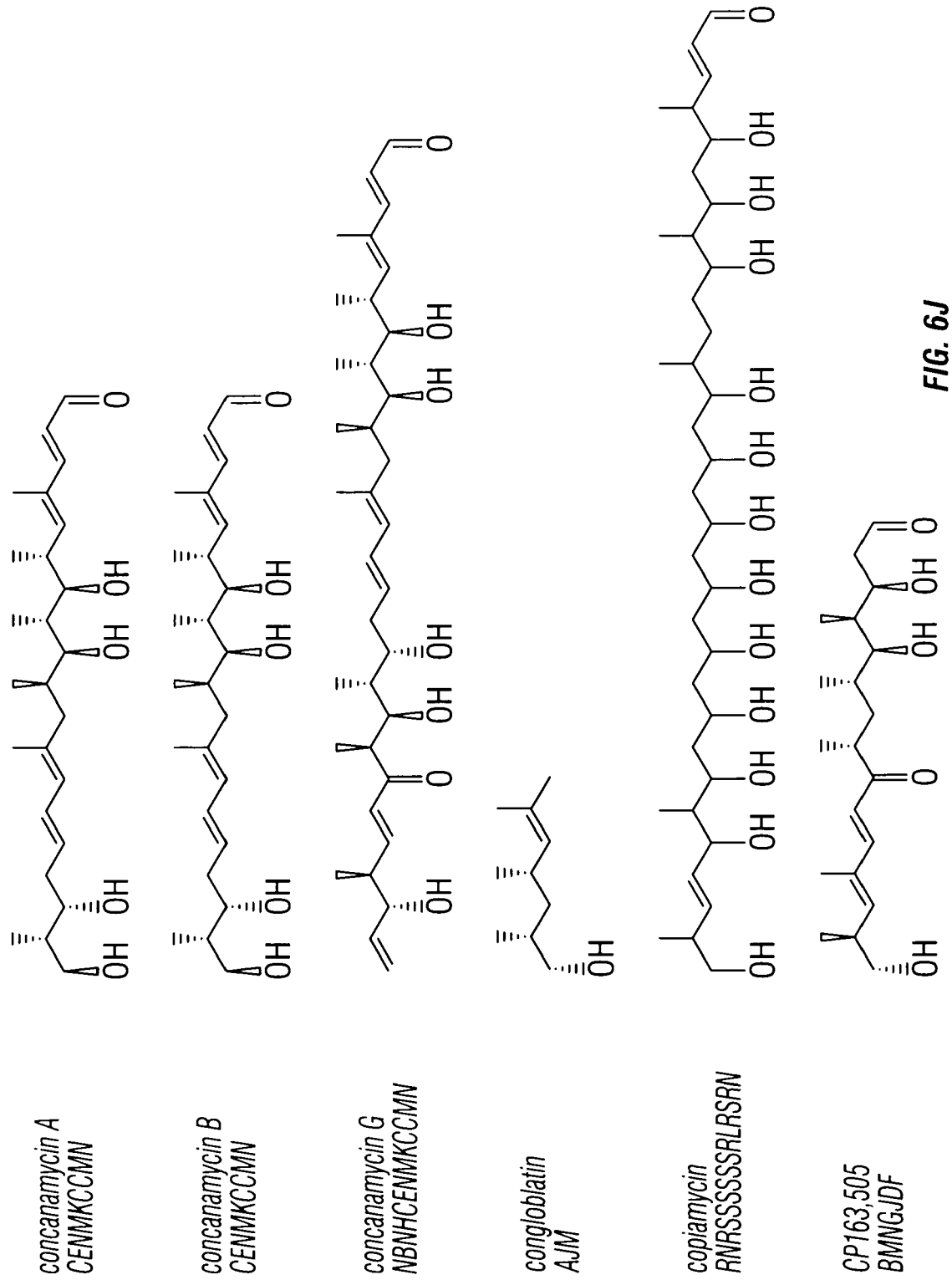
Figure 6K:
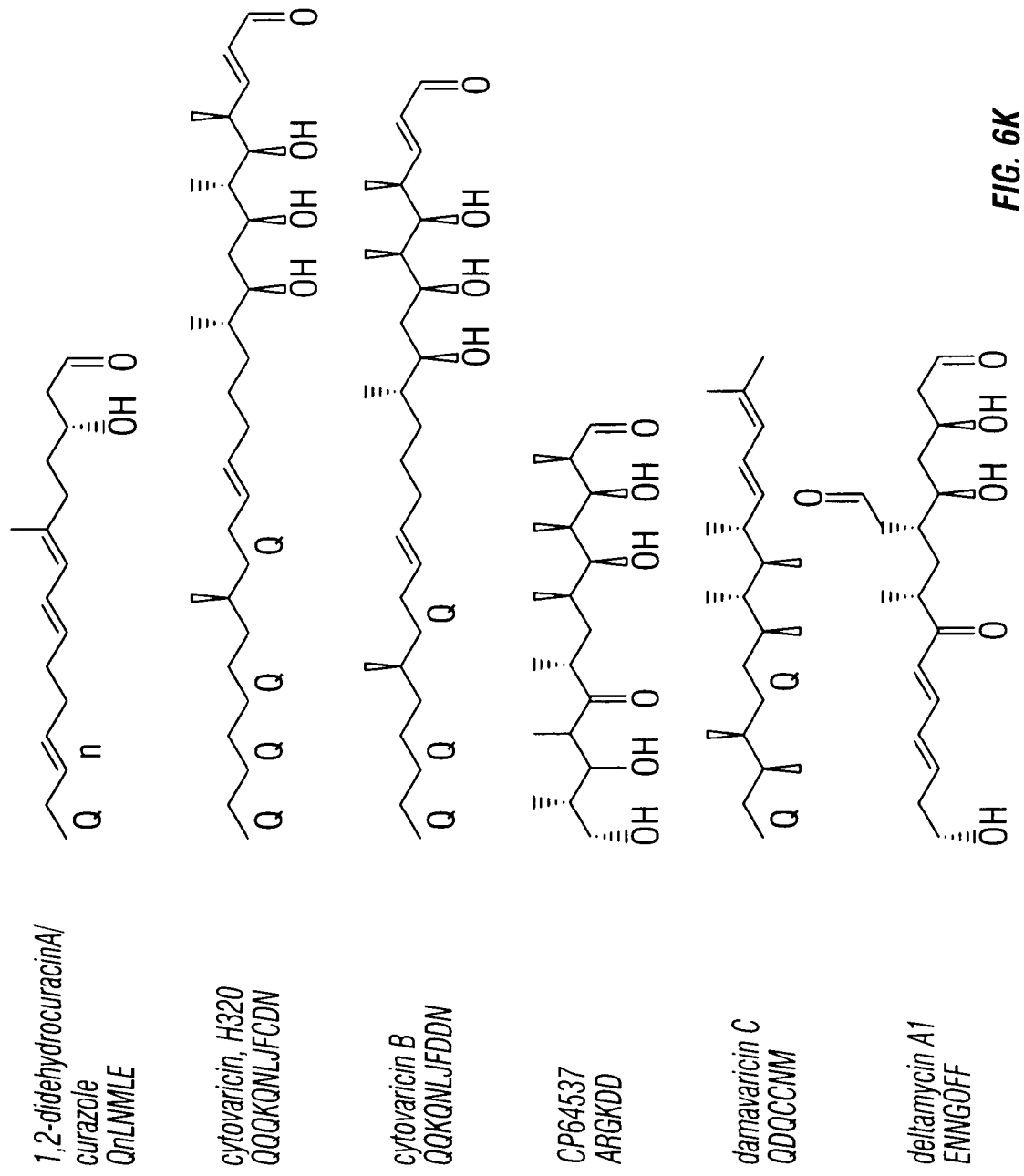
Figure 6M:
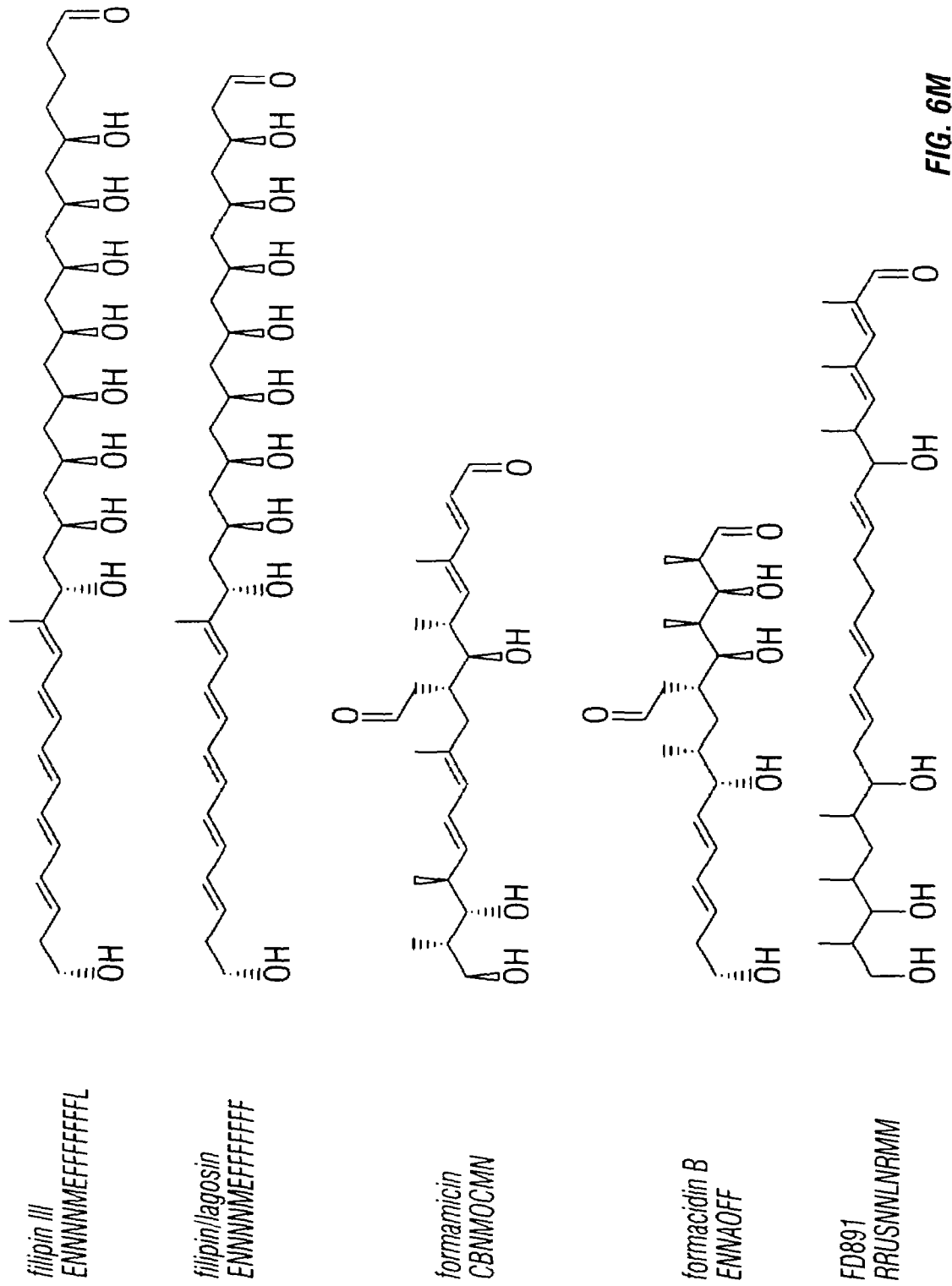
Figure 6N:
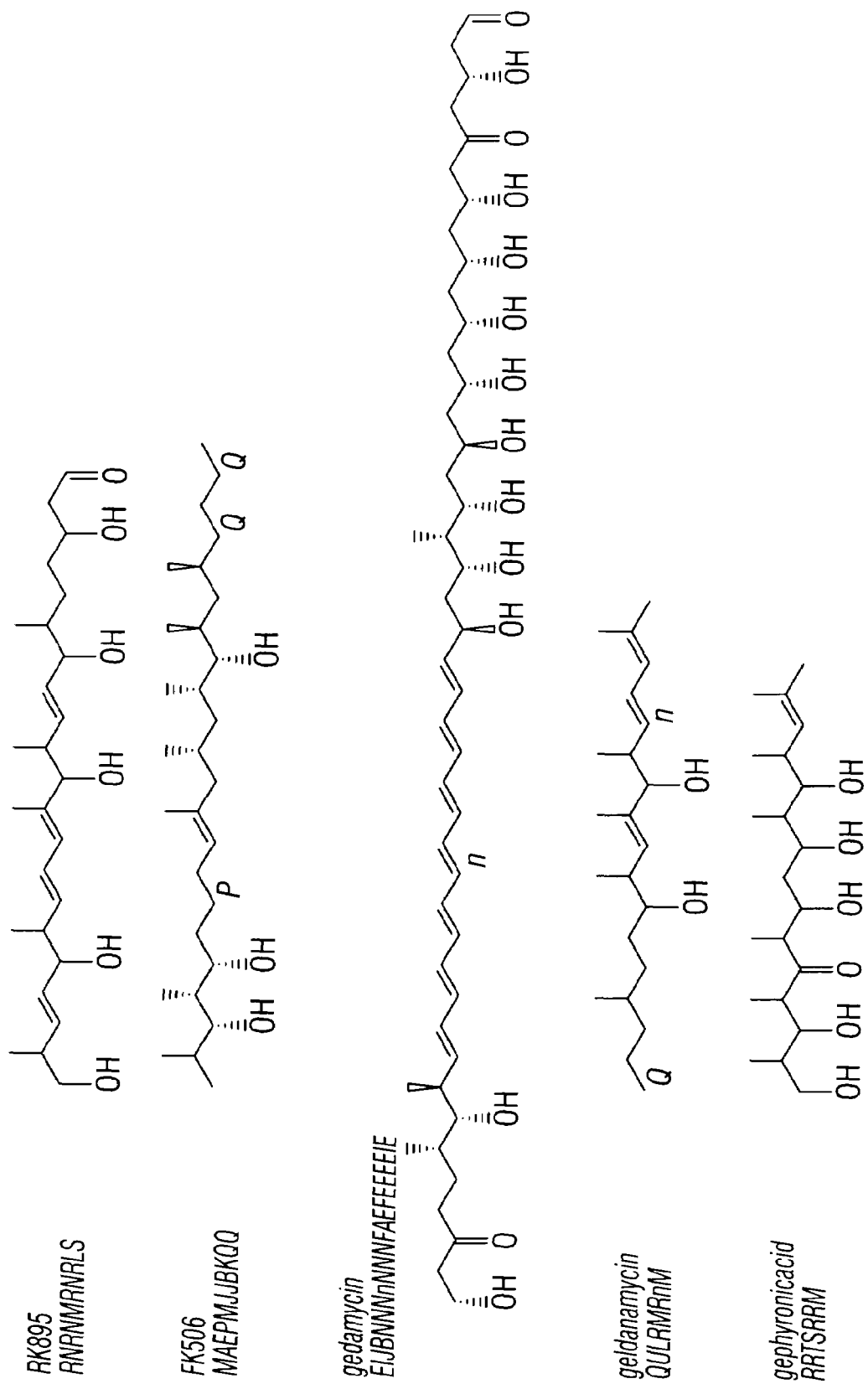
Figure 60:
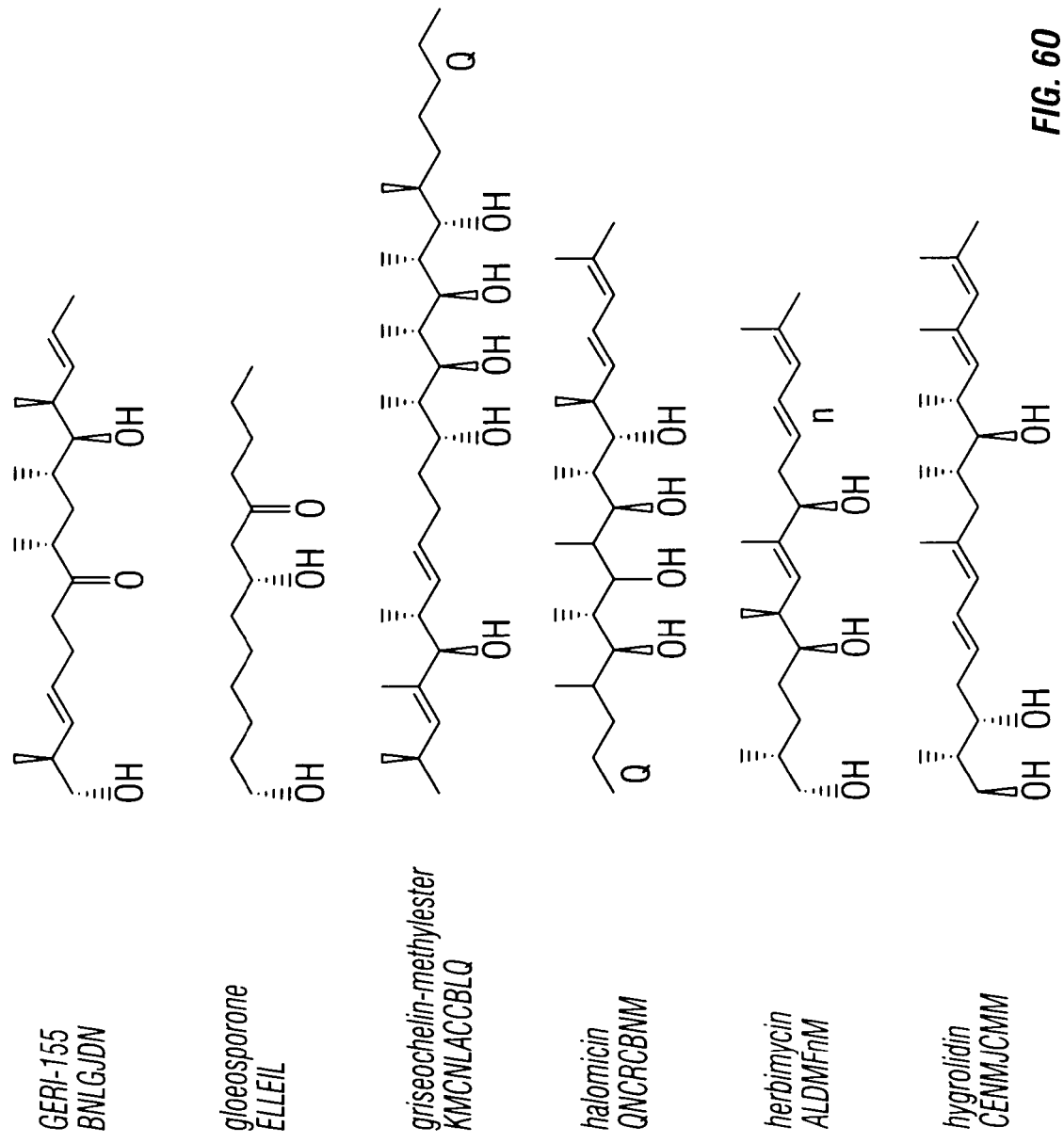
Figure 6P:
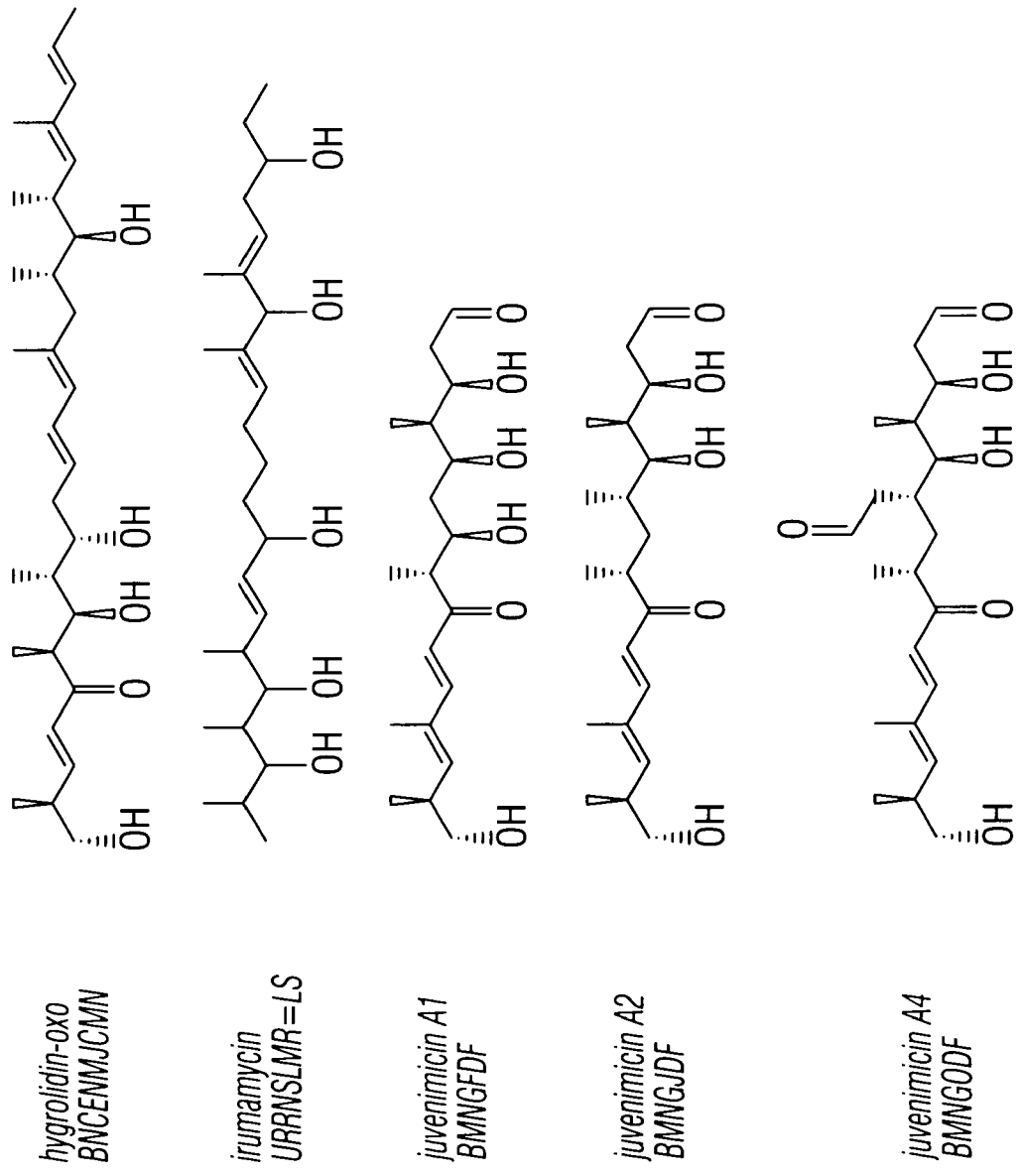
Figure 6Q:
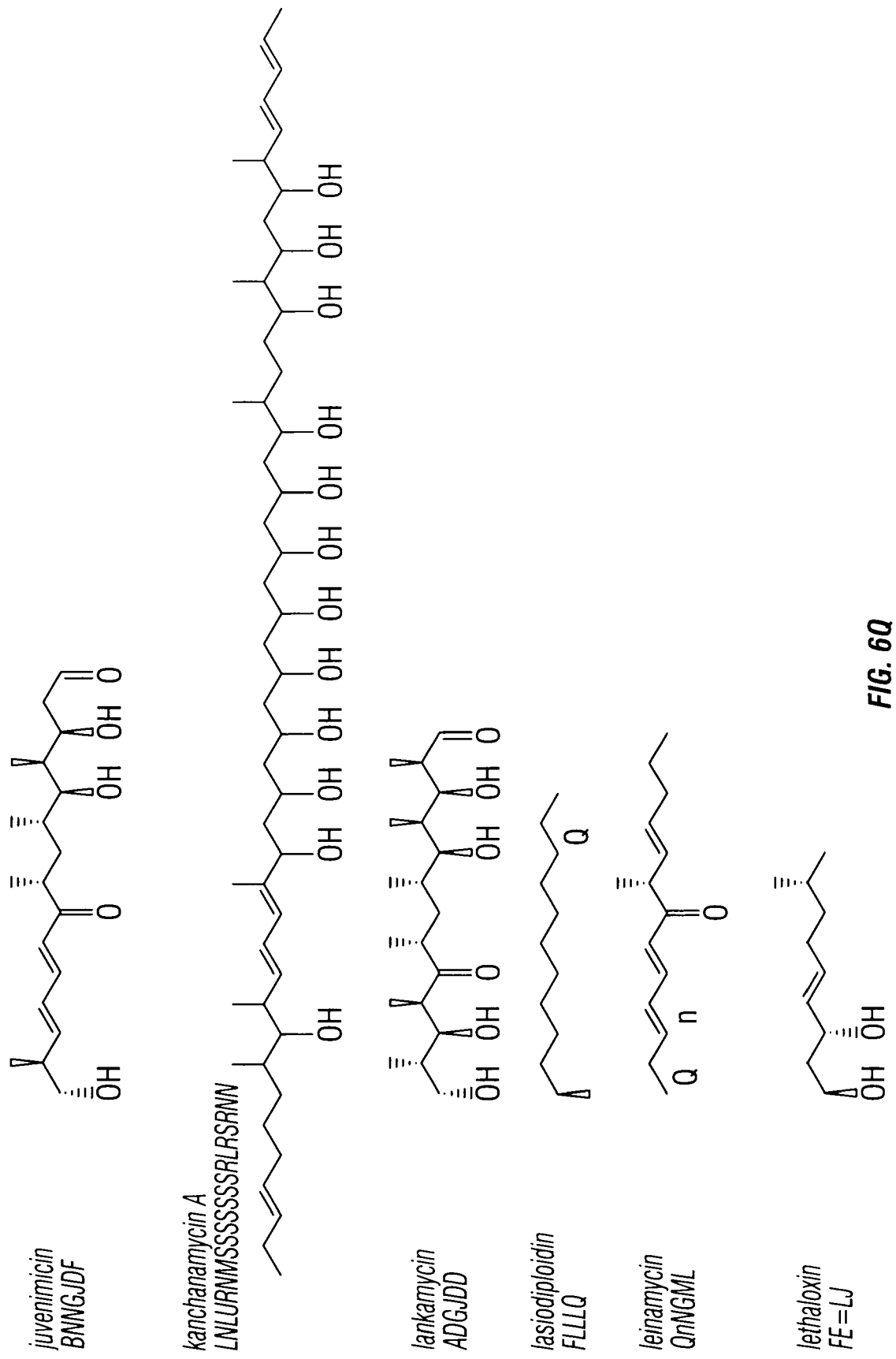
Figure 6S:
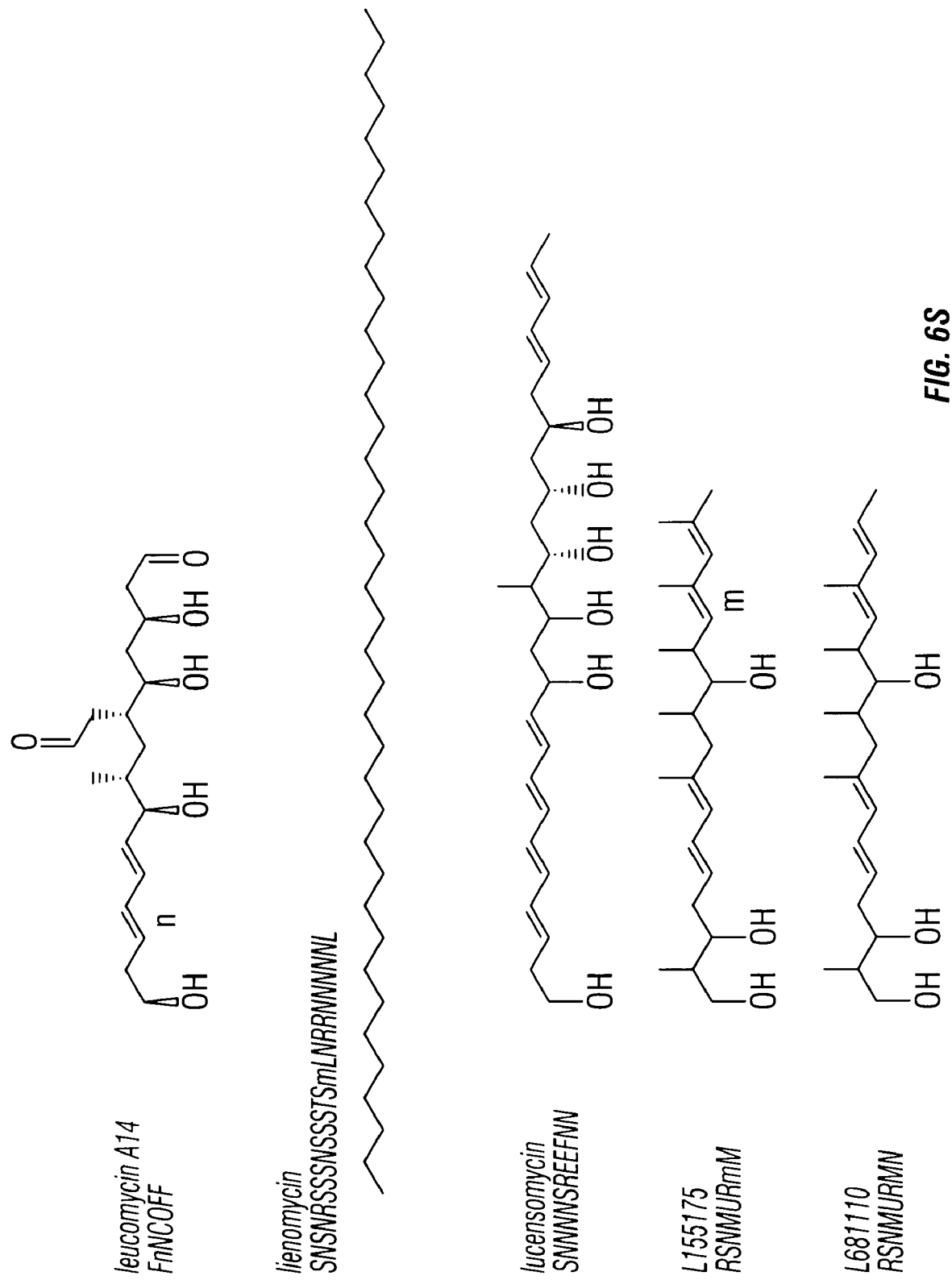
Figure 6U:
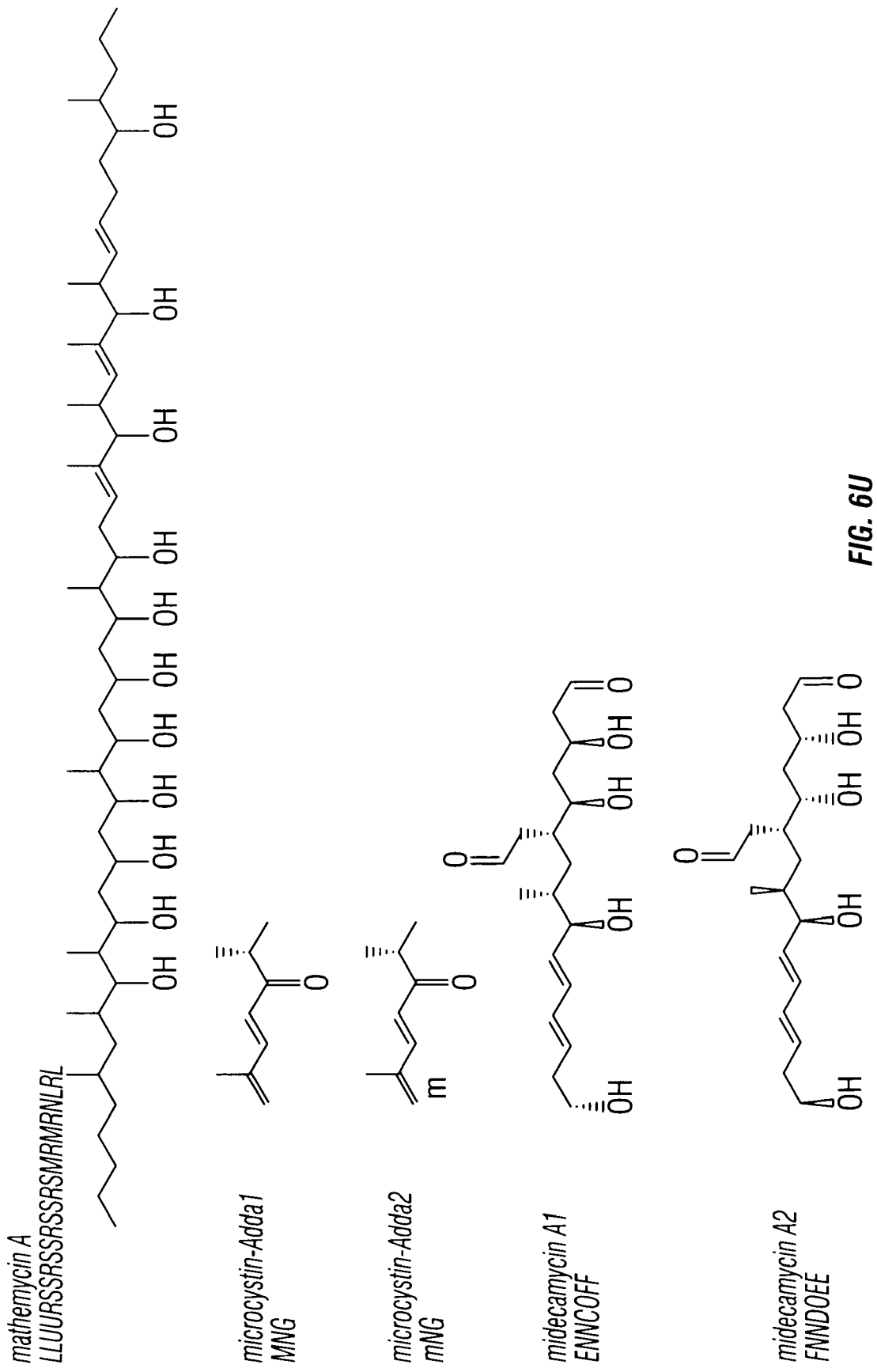
Figure 6V:
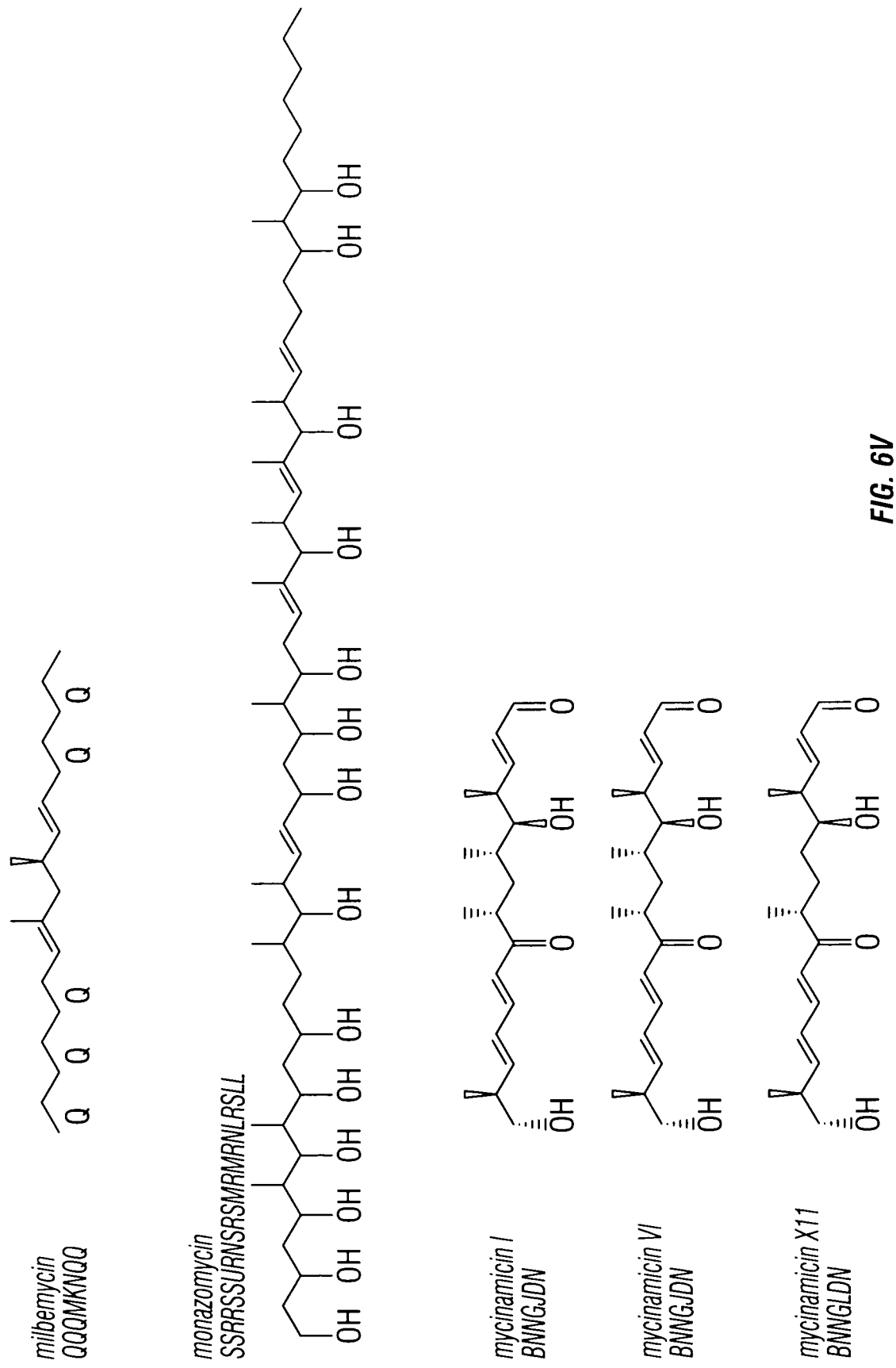
Figure 6X:
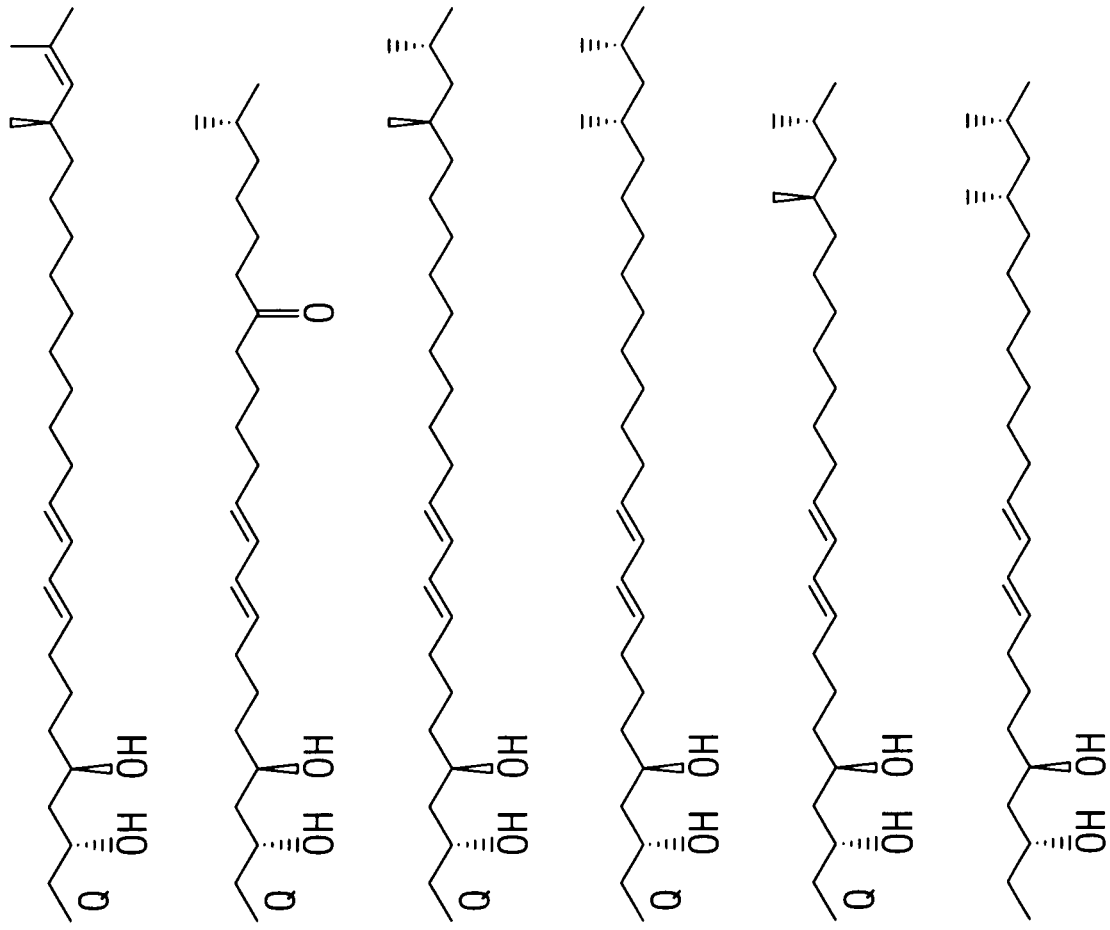
Figure 6Y:
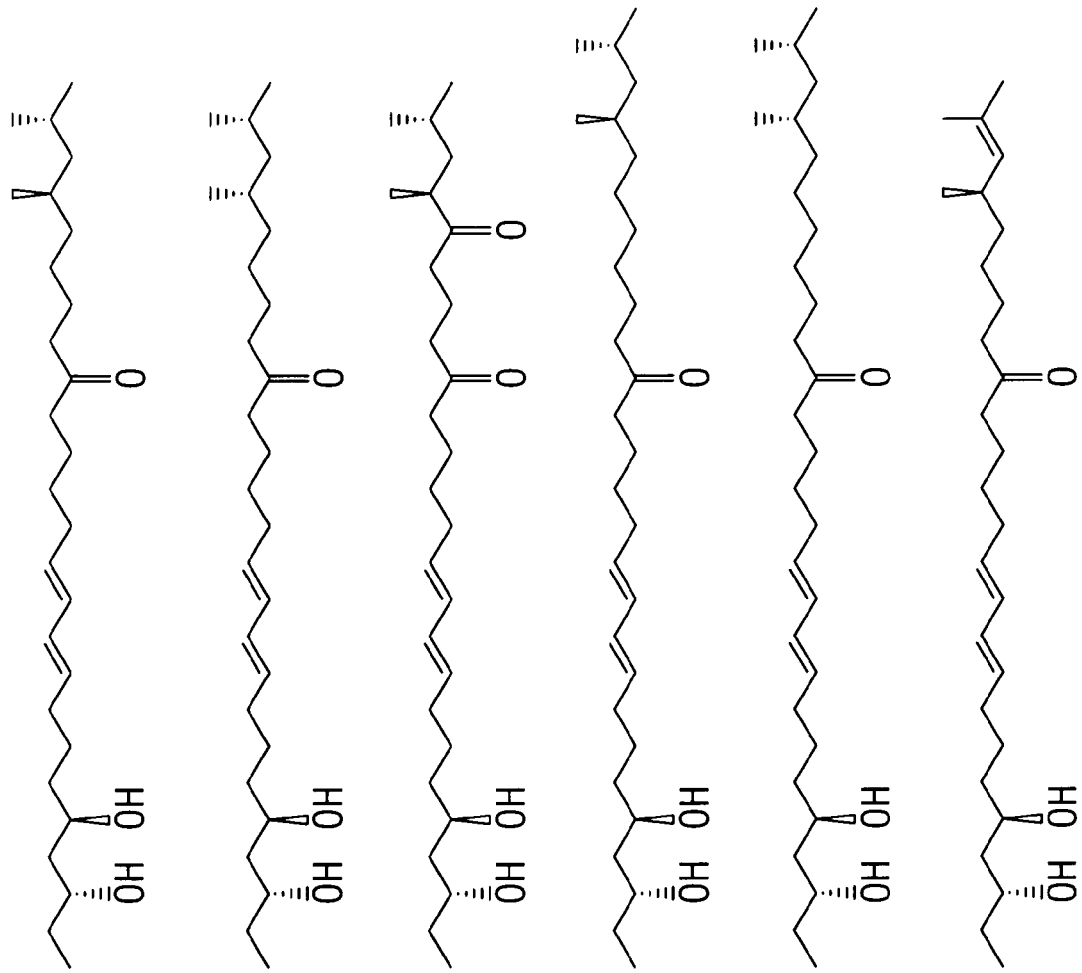
Figure 6Z:
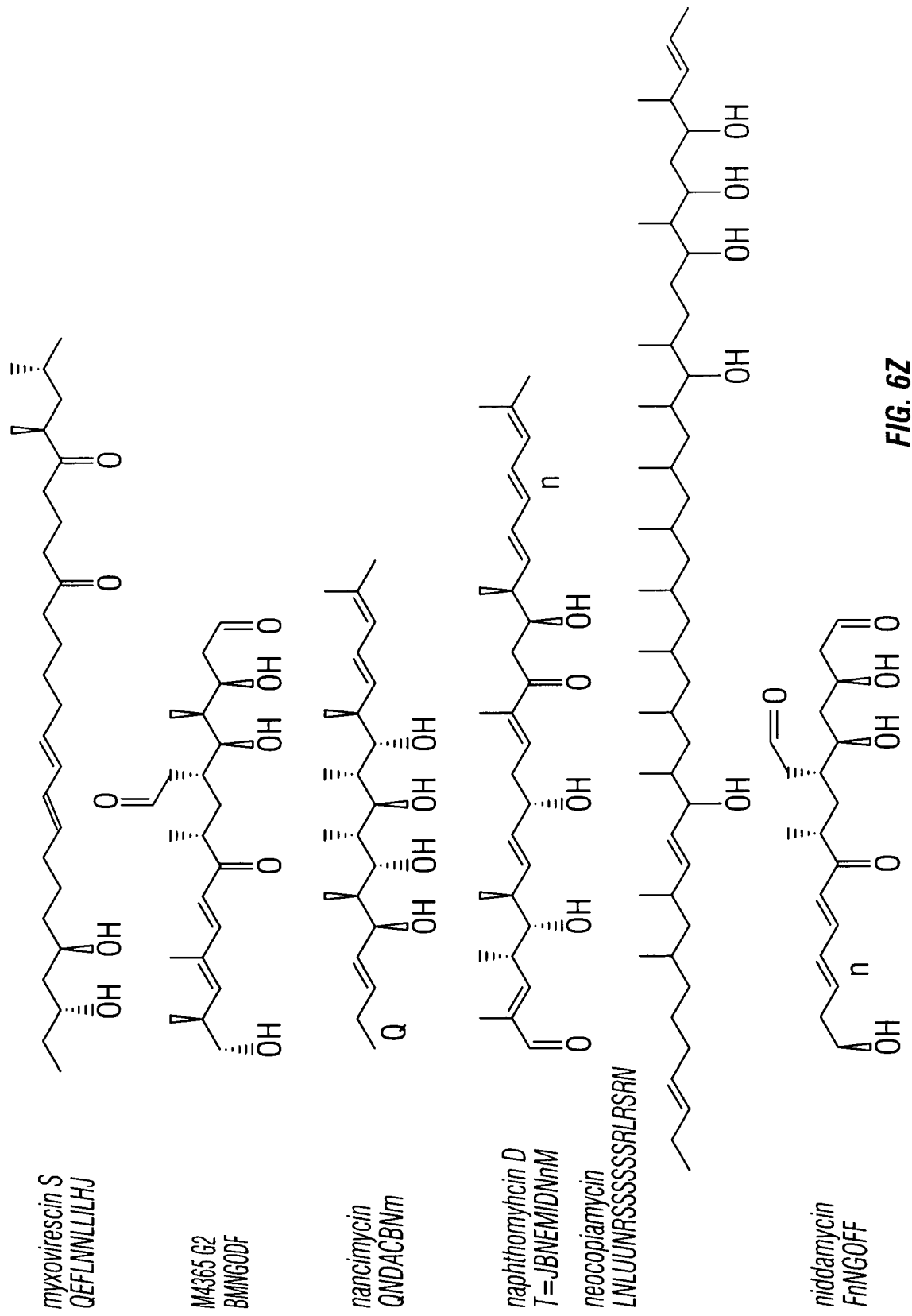
Figure 6A:
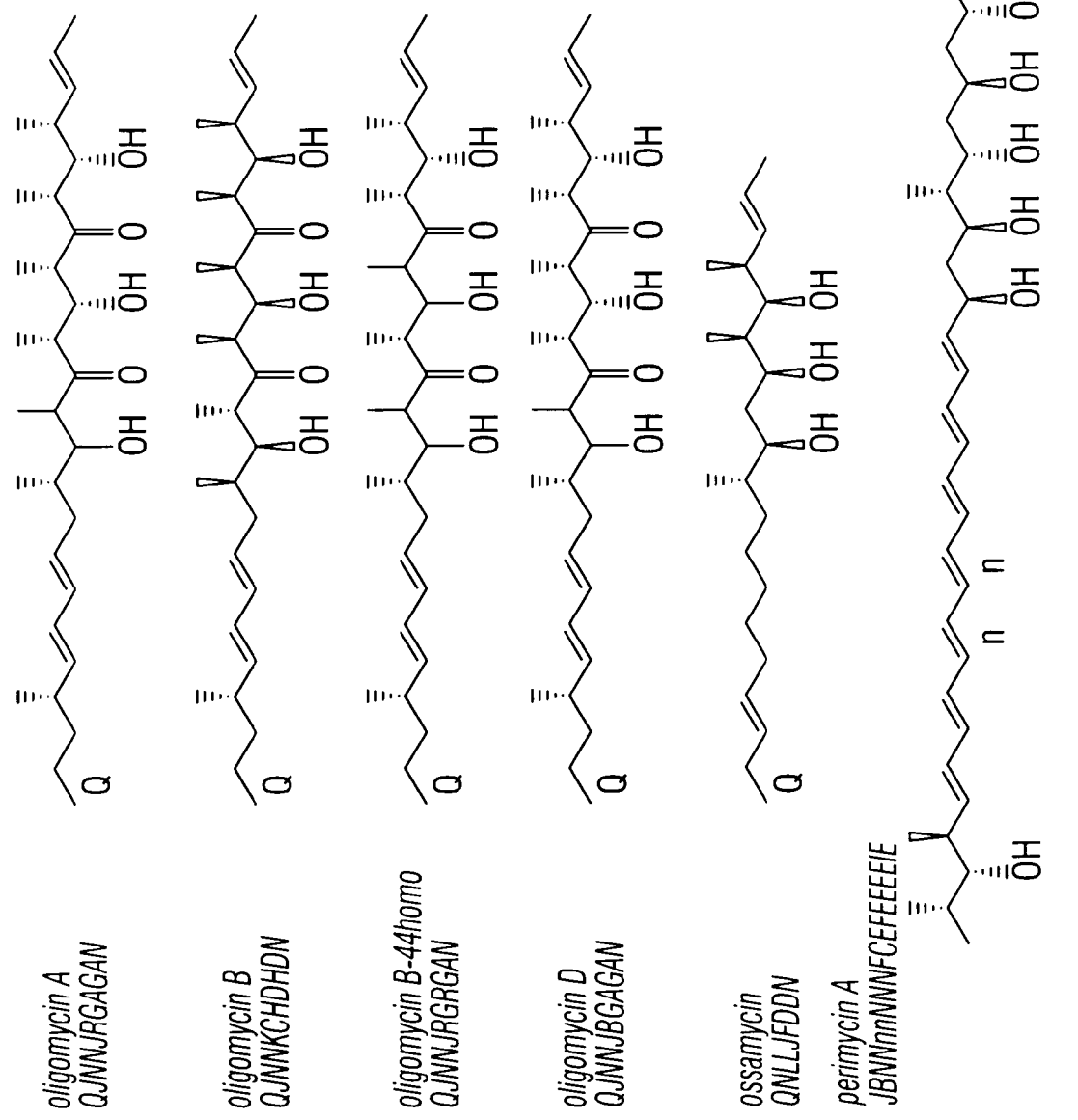
Figure 6A:
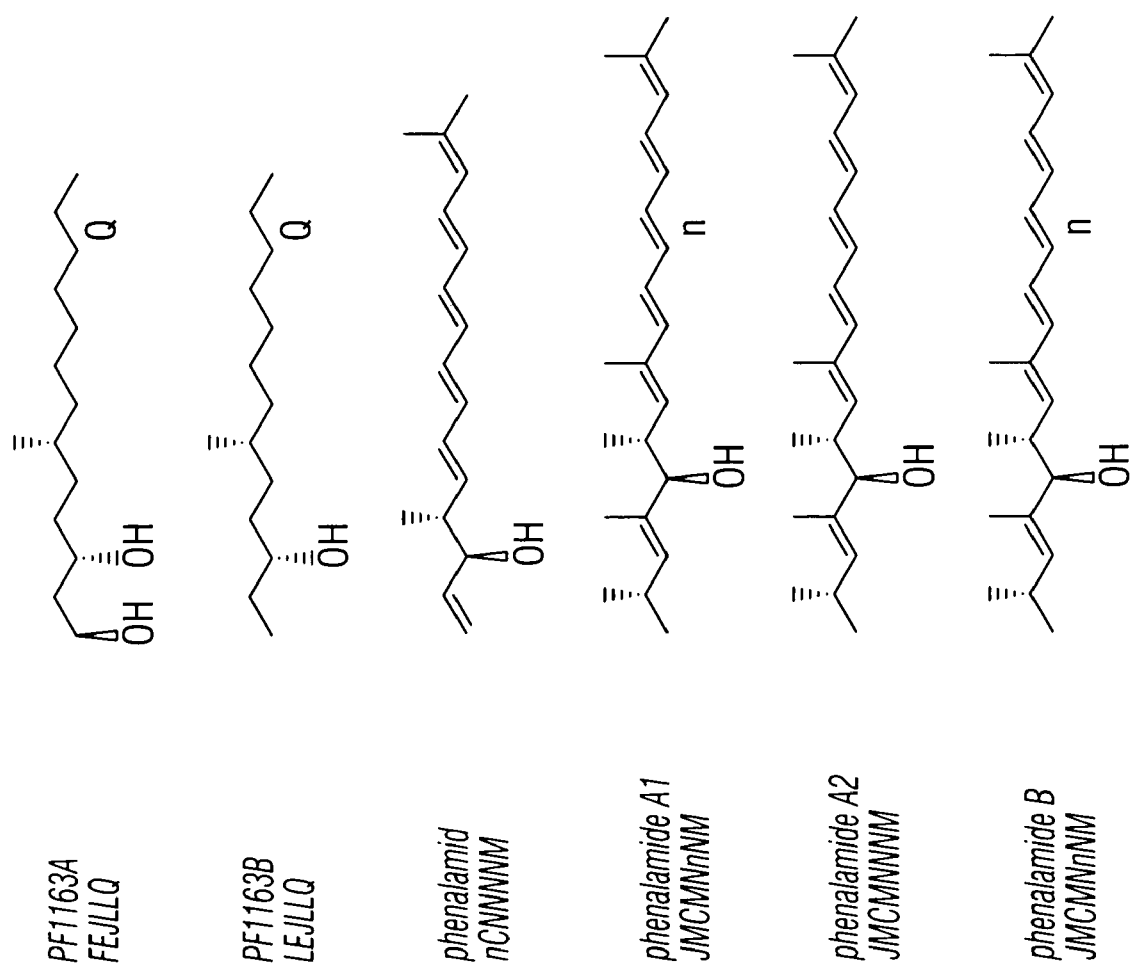
Figure 6A:
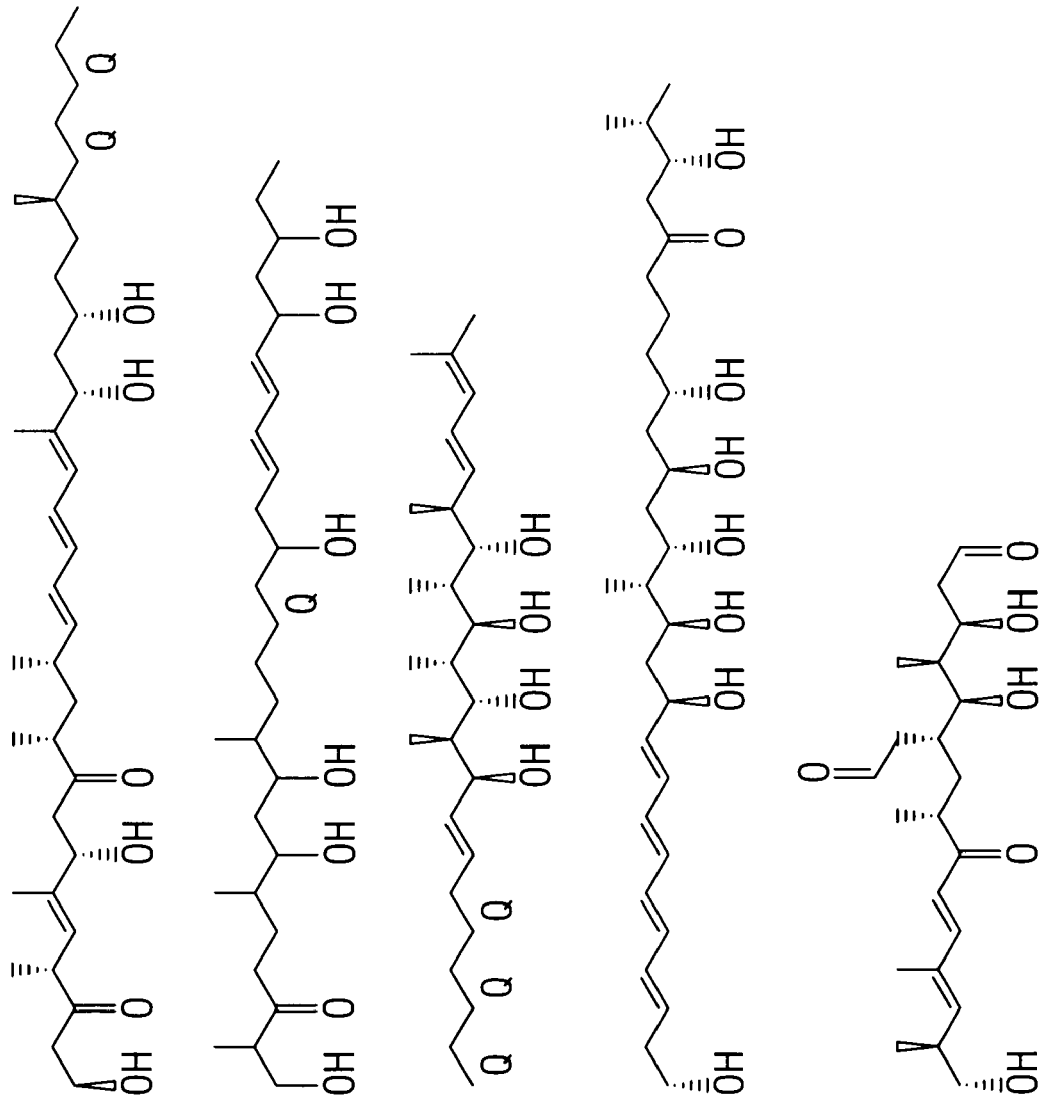
Figure 6A:
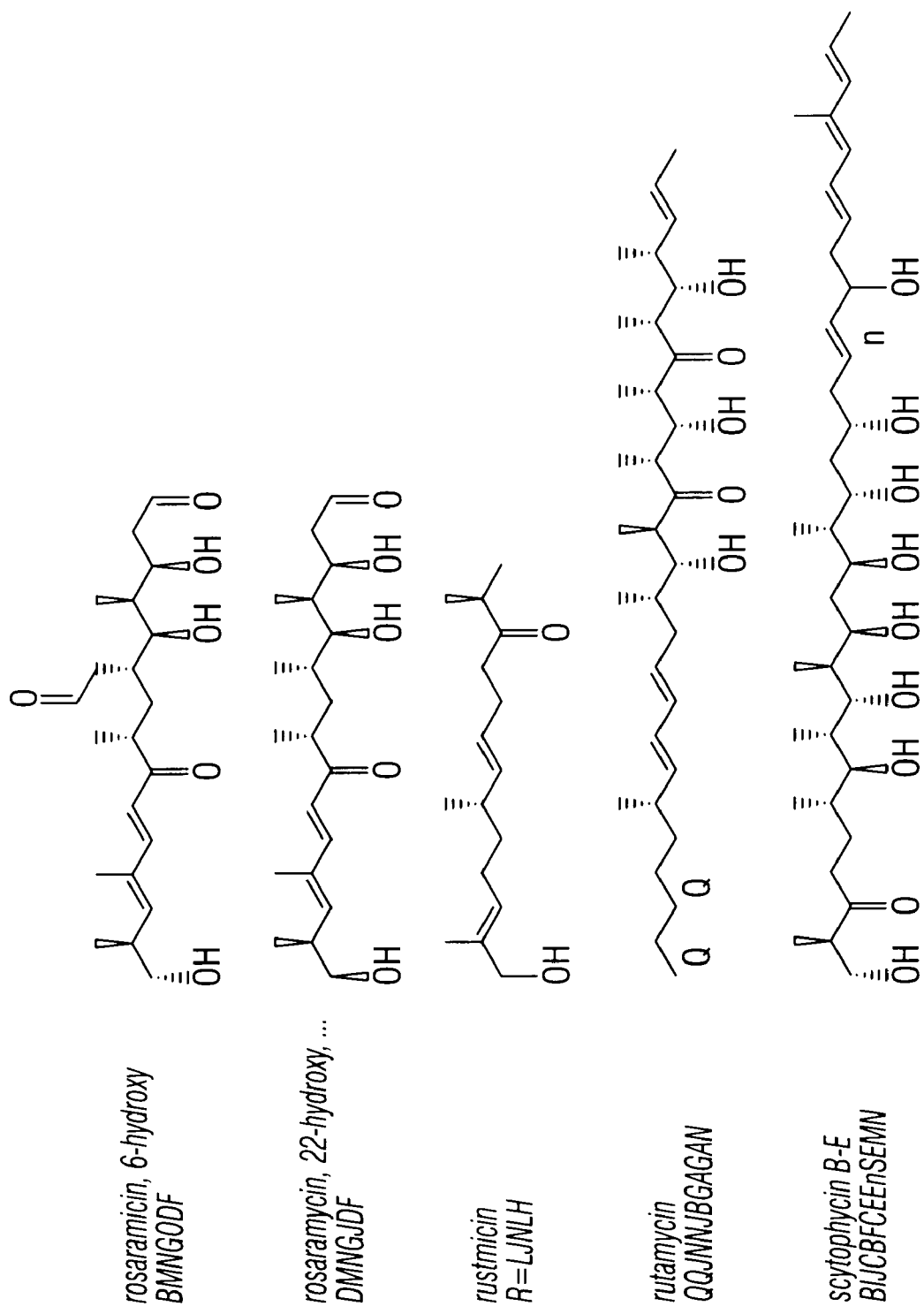
Figure 6A:
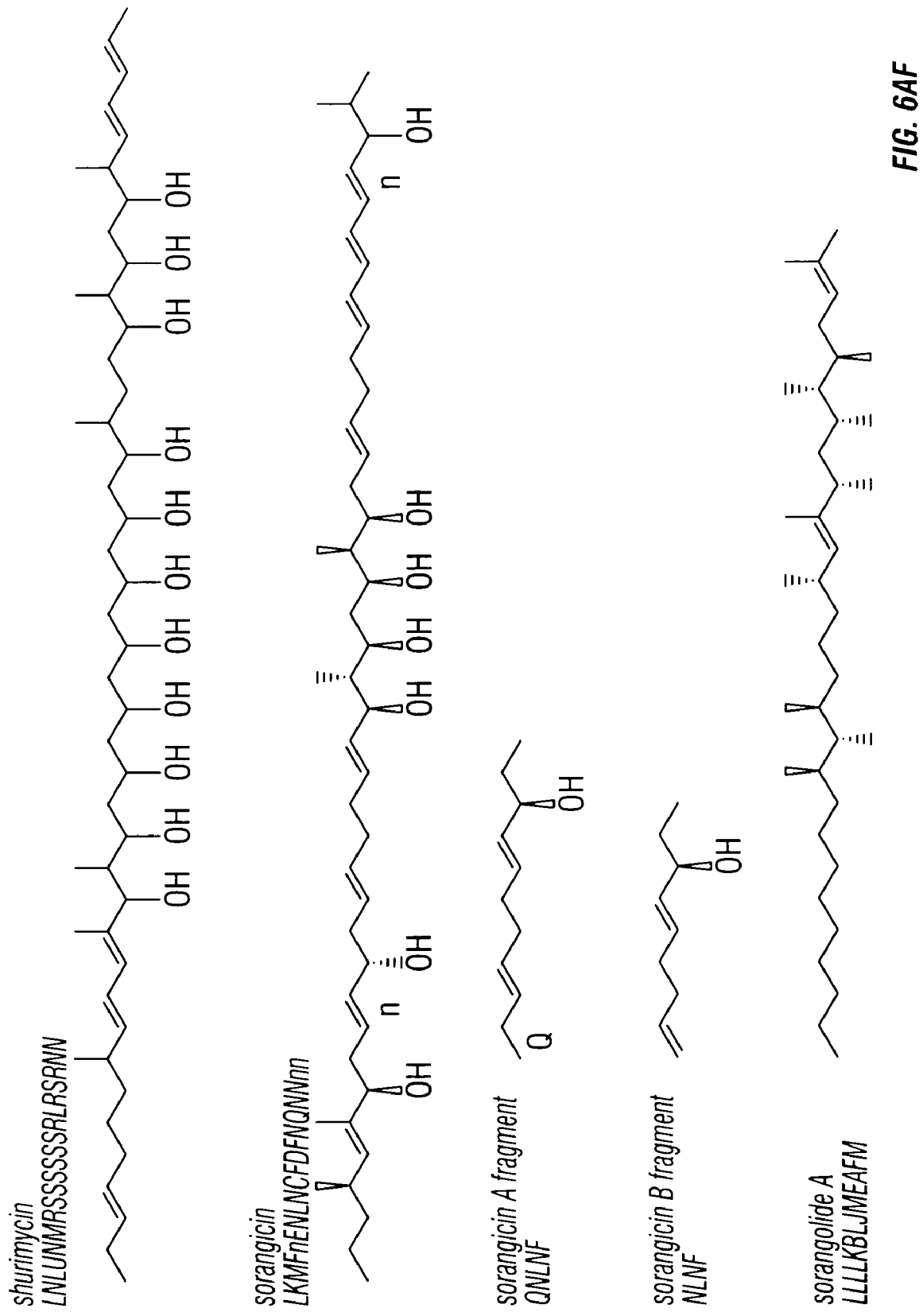
Figure 6A:
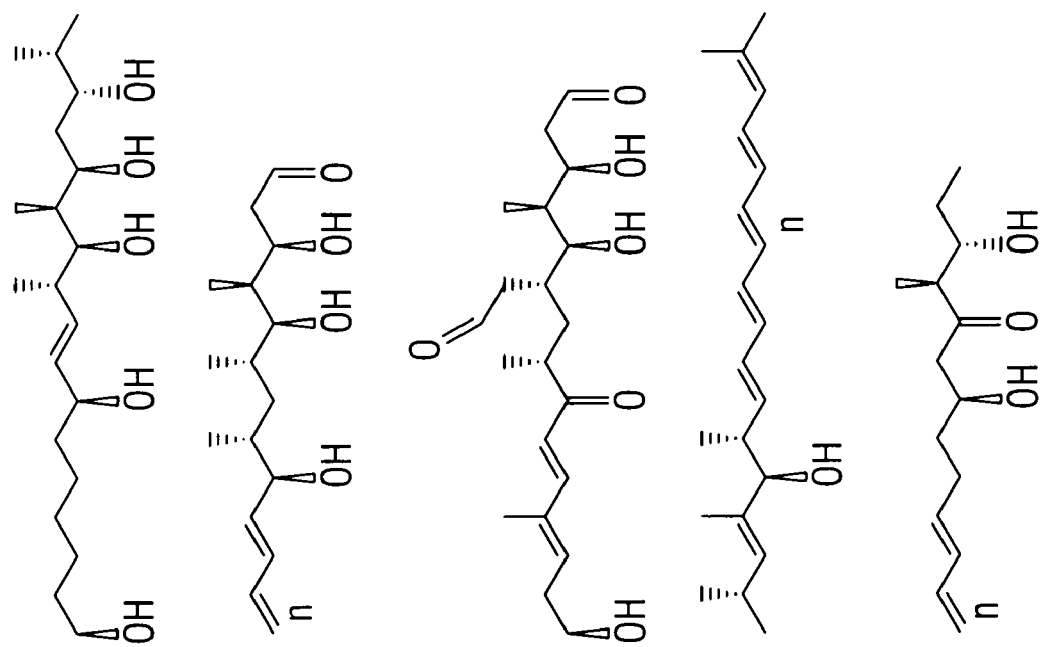
Figure 6A:
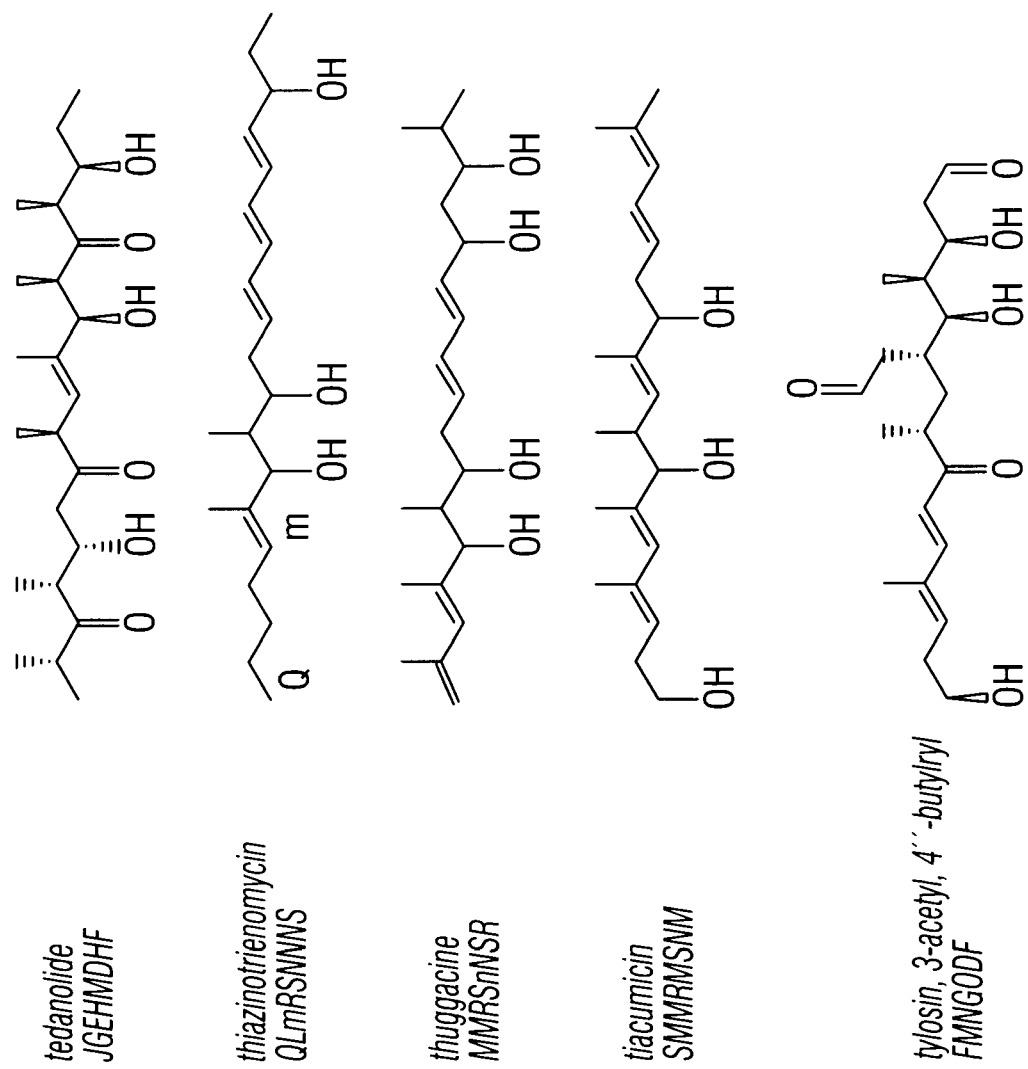
Figure 6A:
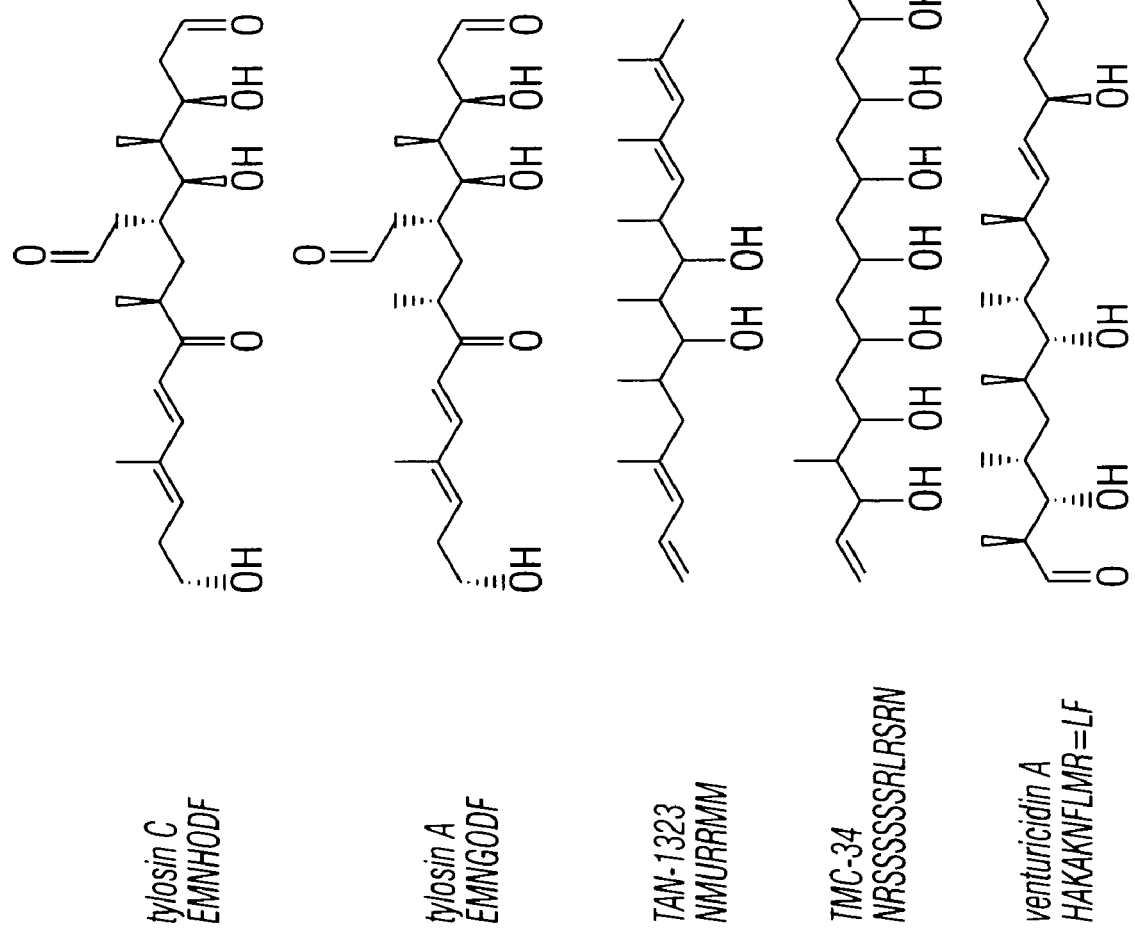

After a particular 2-carbon unit is identified, the next two carbons are processed the same way. This is repeated until all the backbone carbons are identified and labeled as monomers. When all two-carbon units are identified, one has generated an ordered sequence, or string, of monomers, which is a modified CHUCKLES string of the invention. Moieties corresponding to post-PKS modifications are appended to the monomer in the string as an annotation in parentheses. This method of sequencing may be extended to include any type of monomer. FIG. 5 shows a flow chart of this matching method for the generation of the CHUCKLES strings used for all polyketides in a library.

The CHUCKLES string can be in the order corresponding to the direction of biosynthesis on the PKS or its reverse. Each CHUCKLES string has a one-to-many relationship with the PKS gene in the producing organism. Thus, while many different organisms can produce the same polyketide using the same or different PKS genes, each PKS gene generally produces only one PKS that produces only one polyketide (some AT domains can bind different CoAs, leading to the production of multiple polyketides from a single PKS). This allows one to design, from the polyketide structure, a set of PKS genes that would produce that polyketide.

Thus, the present invention provides methods and computational analysis tools for designing PKS genes to produce a desired polyketide. As an illustrative example, the present invention provides a computer program termed MORPH (see the Examples below) that can read the coded library (see the Examples below). An illustrative coded library consists of ~200 unique polyketide CHUCKLES strings. The user specifies the target polyketide, which is converted from molecular structure to a CHUCKLES string.

The program then performs the following, starting with each library compound or string:

(1) aligns library compound and target compound, emphasizing alignment of adjacent monomers common between the two;

(2) fills in the gaps using all possible combinations from all library members;

(3) counts number of non-natural inter-modular boundaries, (4) outputs all these alignments.

The alignments are then sorted based on the number of non-natural inter-modular boundaries.

This illustrative program allows one to design and find PKS genes that encode PKS enzymes that are combinations of two or more different PKS enzymes with the fewest inter-modular boundaries, and optionally the fewest inter-protein boundaries. Many other alternative embodiments are provided by the present invention.

For example, one can include the naturally occurring PKS that produces the target polyketide in the coded library to allow components of that PKS to be incorporated into the design of a new PKS. Also, one can include in the coded library non-naturally occurring PKS enzymes, such as those produced and published in the scientific and patent literature to make novel polyketides, in the coded library. See, e.g., PCT publication Nos. WO 98/49315 and WO 96/40968, both of which are incorporated herein by reference.

This CHUCKLES-coded polyketide library can be stored in a computer file as a set of records. In one embodiment, each record contains the chemical name of the polyketide, the unannotated CHUCKLES (containing basic macrocyclic monomers), the annotated CHUCKLES (containing basic macrocyclic monomers with information about post-PKS modifications), the producing organism(s), and other information (e.g., linearized representation of the polyketide structure, the accession number of organisms or plasmids that have been deposited, gene sequence information, and references).

The MORPH program can read in the polyketide library entries to an array or list of data structures, where each entry data structure contains all or a selected subset of the fields in each library record. The MORPH program then reads in the CHUCKLES-coded TARGET polyketide from the user. This TARGET may optionally be blocked from the library so that it is not used as a STARTER or left in the library, i.e., if it is only distantly related to other known polyketides, or some modules could be useful in designing novel PKS genes, or it is desired to replace only certain PKS modules. This program could also be used for analoging at a particular position via wild-cards defined as part of the TARGET sequence by the user.

Figure 4A:
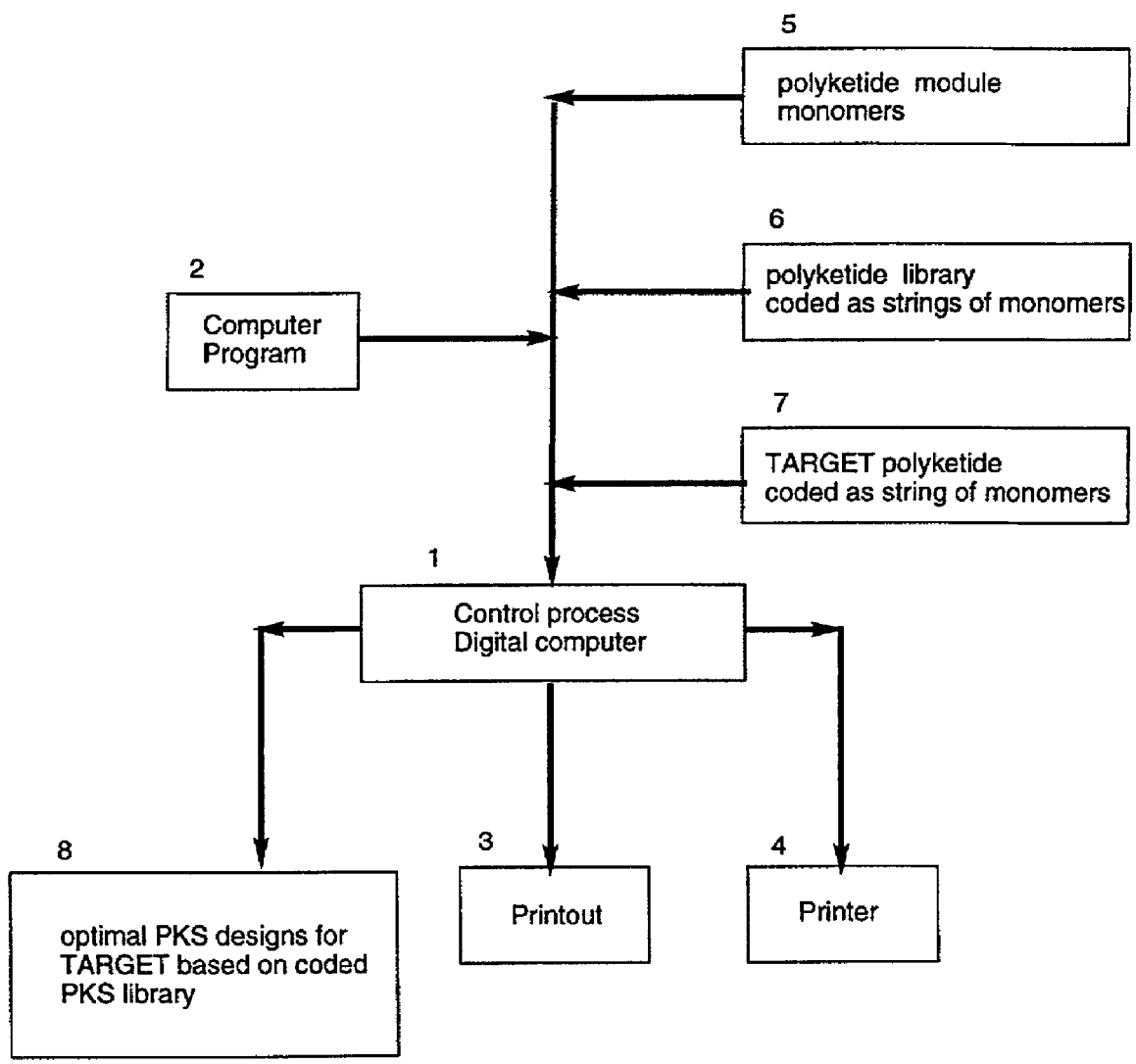
FIG. 4A is a block flow diagram of a computer system to design a novel PKS (and corresponding genes).
Figure 4B:
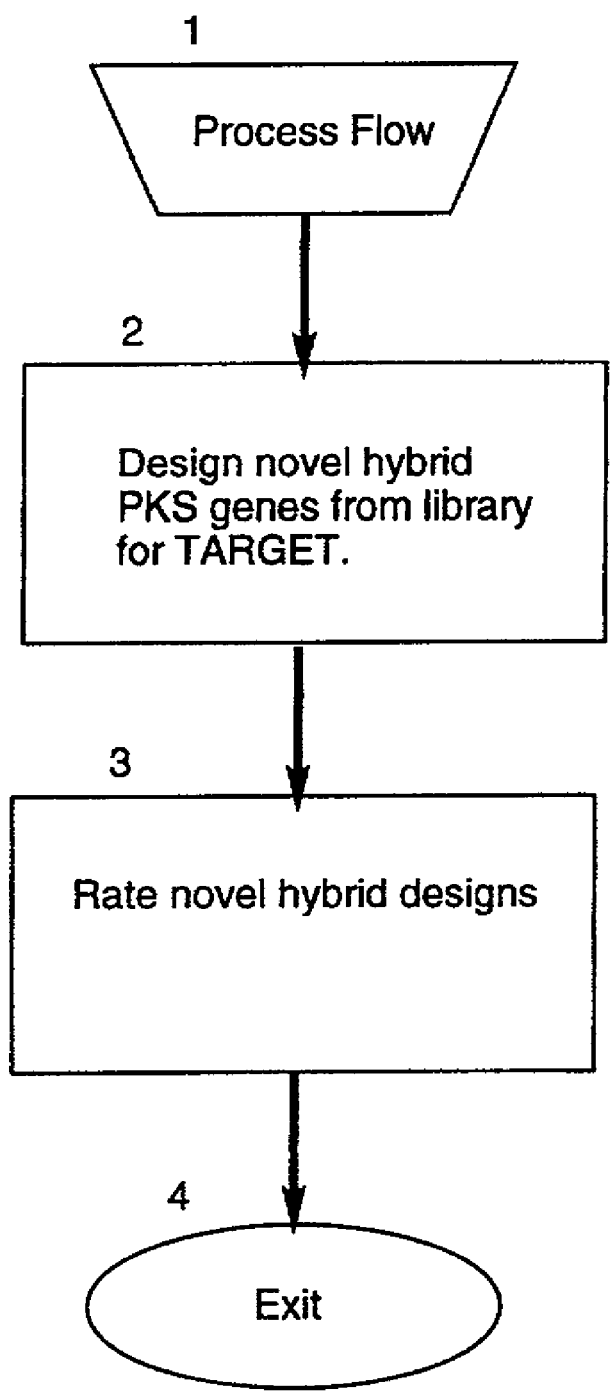
FIG. 4B is a block flow diagram wherein the "Computer Program" block (2) of Flowchart
Figure 4C:
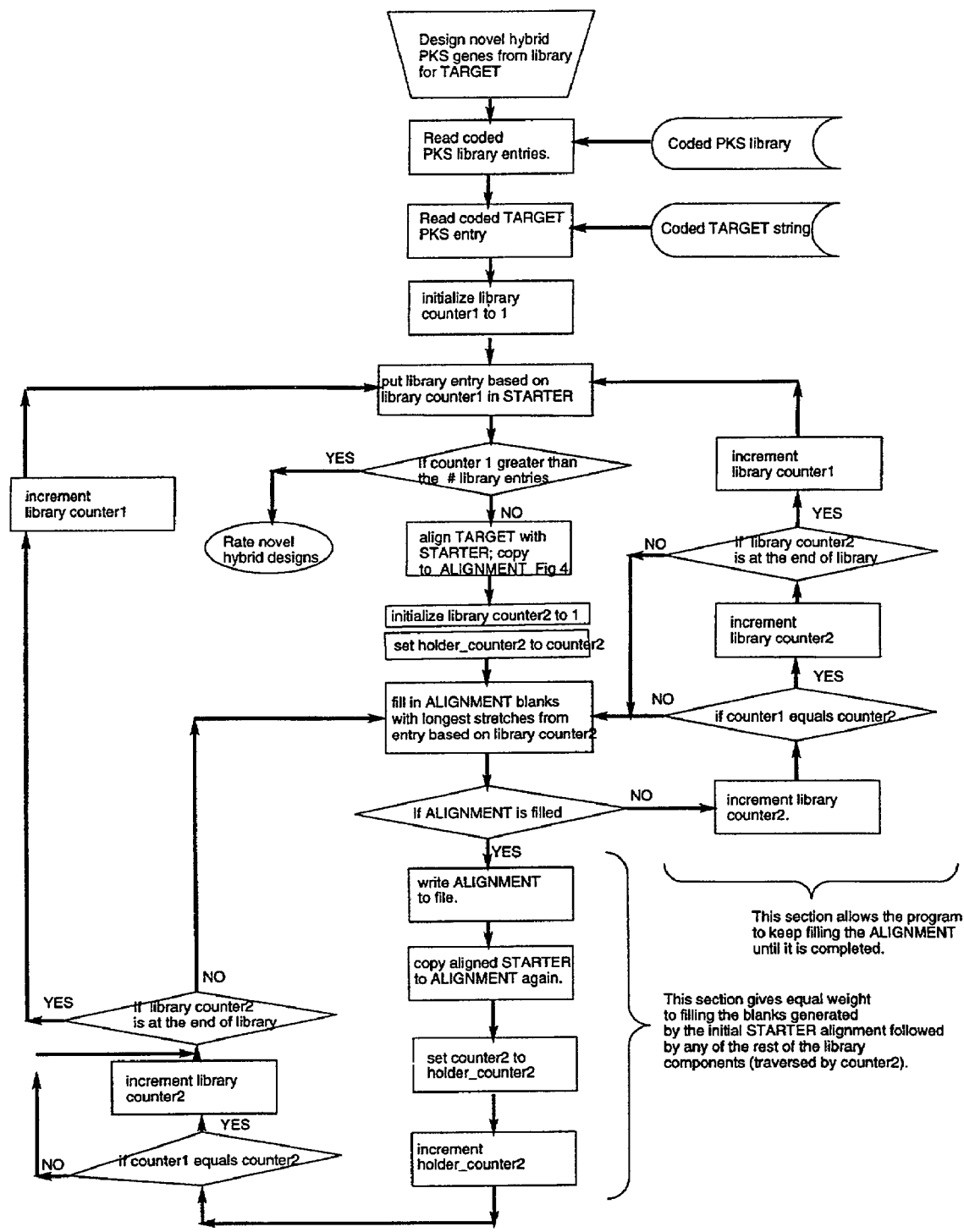
FIG. 4C is a block flow diagram wherein the "Design novel hybrid PKS genes from library for TARGET" block of Flowchart
Figure 4D:
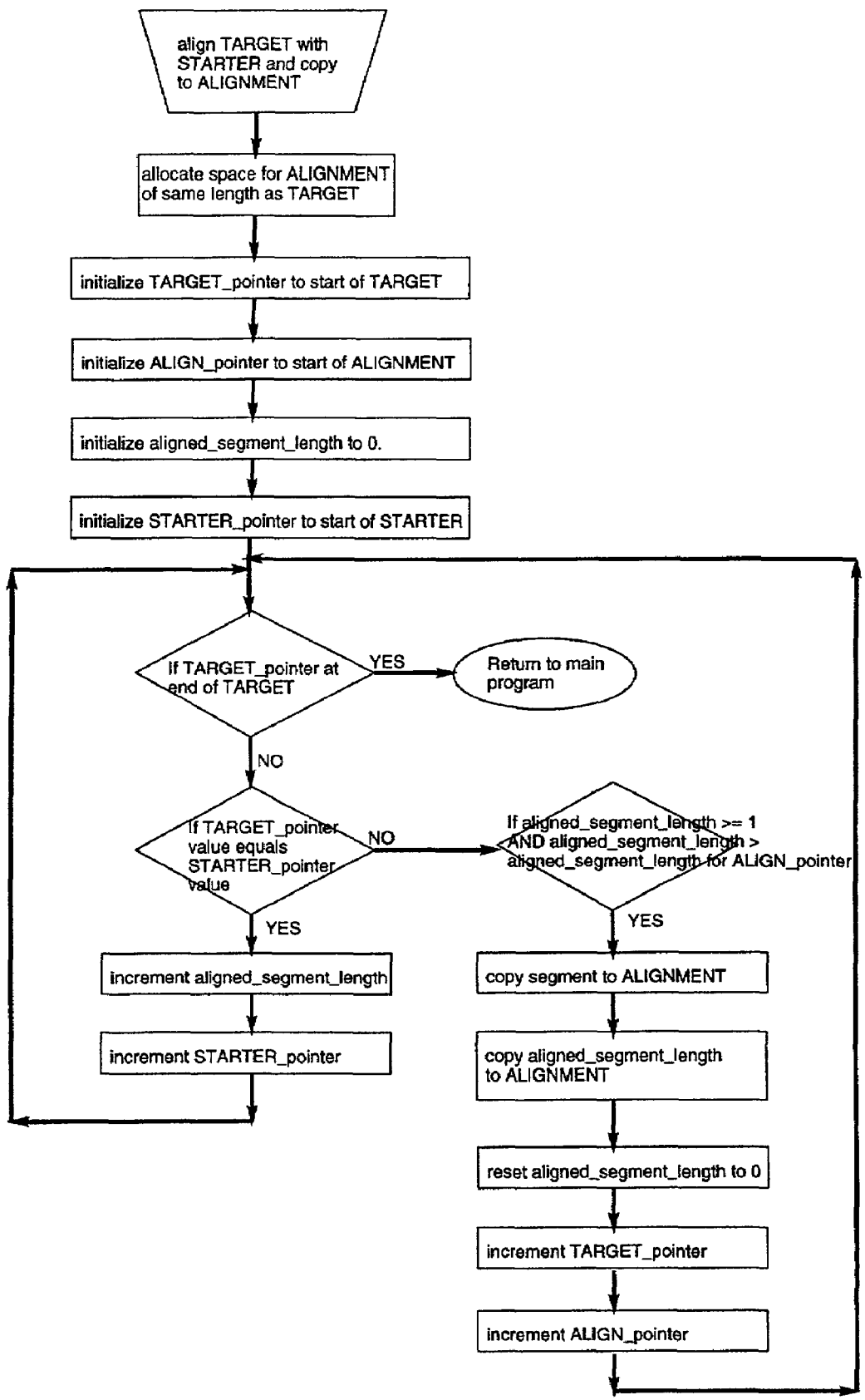
FIG. 4D is a block flow diagram wherein the "align TARGET with STARTER; copy to ALIGNMENT" block of Flowchart
Figure 4E:
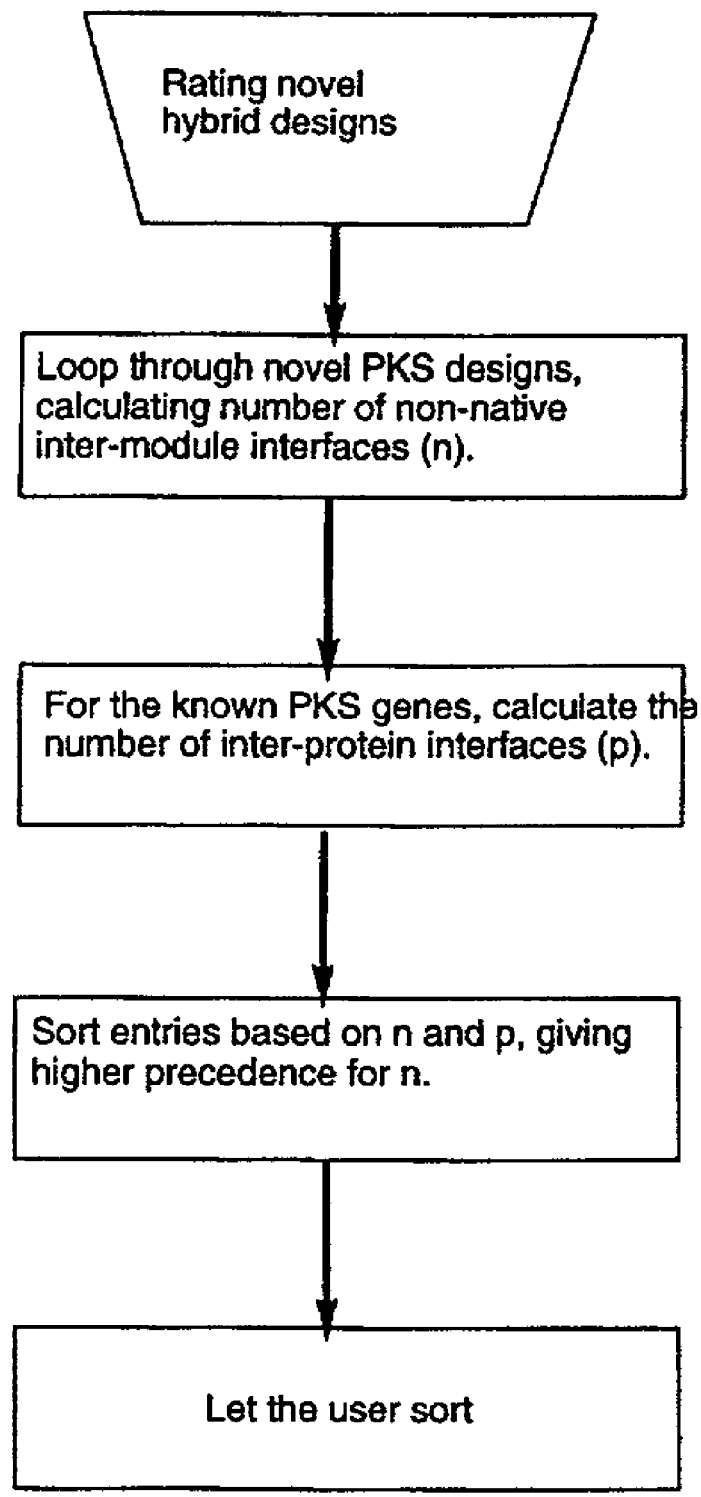
FIG. 4E is a block flow diagram wherein the "Rate novel hybrid designs" block (3) of Flowchart

Each member of the coded PKS library can be selected as a STARTER unit. Thus, during a run, all library members can be given an equal chance as STARTER units. After a STARTER is chosen, the TARGET is aligned with it. See Flowchart FIG. 4D. Any method of alignment can be used such that the maximal number of adjacent STARTER modules is used in the final alignment. After the maximal adjacent modules are used in the ALIGNMENT, smaller adjacent sets or individual modules from the STARTER are used to fill in the gaps. There may be several alignments that are equally good based on the attempt to optimize the number of adjacent modules. For example, if the TARGET contains the "JDG" substring, then 6-dEB, identified with the A1D2G3J4D5D6 CHUCKLES string, may align as

| TARGET | JDG | | TARGET | JDG |
|--------|------|----|--------|------|
| 6-dEB | J4D2G3 | or | 6-dEB | J4D5G3. |

Both of these alignments have different maximal adjacent modules, with the same length of two (D2G3 in the first and J4D5 in the second). Accordingly, either alignment could be used as STARTERs.

With the optimized alignment from the STARTER, other library entries are systematically used to complete the alignment, or fill in the gaps. This part may be performed on either the optimized ALIGNMENT described above, or the ALIGNMENT without the single modules from the STARTER; the removal of the individual modules opens up more space into which larger pieces of the FILLER might be placed. The first library entry is designated as the FILLER. If the FILLER is the same as the STARTER, the next library entry is used as the FILLER. This library entry is flagged as the CURRENT_FILLER_LIBRARY_ENTRY. The same method for finding maximally adjacent modules and then smaller sets or single modules is used to fill the gaps in ALIGNMENT from the FILLER. If not all the gaps are filled in the ALIGNMENT, then the next library entry is used as a new source; that is, it is designated as the FILLER, and the gaps are filled further. This is repeated until the ALIGNMENT is complete or the end of the library is reached.

Assuming all modules in the TARGET are represented in the library, the ALIGNMENT is eventually completely filled. The completed alignment is then written to an output file on the computer disk. When the ALIGNMENT is complete, or there are no more FILLERS in the library, the TARGET and STARTER alignment are re-copied to ALIGNMENT. The CURRENT_FILLER_LIBRARY_ENTRY is incremented, and a new attempt to fill in the gaps is started.

When the CURRENT_FILLER_LIBRARY_ENTRY has reached the end of the library, the ALIGNMENT is wiped, and a new STARTER is chosen. The above process is then repeated for the next STARTER. When all library entries have been used as starters, then all feasible novel polyketide synthases have been generated and written to the computer file. The novel PKSs are then read back into memory and can be further evaluated. An illustrative evaluation process involves:
(1) counting the non-native inter-module interfaces, and
(2) counting the number of native inter-protein interfaces (for known and annotated gene sequences).

The novel PKSs are then sorted based on these two numbers, giving higher priority to the non-native inter-module interfaces. In this mode, the goal is to identify those novel PKSs that contain the fewest non-native interfaces.

By providing methods and means for the computer-assisted analysis of polyketides and PKS genes, the present invention greatly facilitates the identification and production of new polyketides with useful activities. Those of skill in the art will appreciate that while the invention is in part illustrated in the Examples below with respect to the design of new PKS genes for known polyketides, the invention can also be used to design PKS genes for novel polyketides. In this embodiment, one simply provides the structure of the novel polyketide to the MORPH or other program of the invention to generate the desired PKS genes.

Moreover, while the invention is exemplified below by designing new PKS genes composed of the coding sequences for one or more complete modules of two or more different PKS genes, partial modules can also be employed. With the appropriate choice of monomer sets and corresponding coding of the library to be searched, one can generate new PKS gene designs that take advantage of the potential to fuse one PKS gene coding sequence to another at a site corresponding to an intra-modular junction. In another embodiment, one can use "wild-cards" in the encoded polyketide or library to take advantage of known or predicted SAR. Thus, if one knows that a particular position in a polyketide can be varied (i.e., a hydrogen, methyl, or ethyl group at a location determined by an AT domain of a particular module, or a hydroxyl or keto group at a location determined by the presence or absence of a KR domain in a particular module) then one can use a wild-card monomer designation in the polyketide CHUCKLES string to generate PKS genes that produce each of the desired variants.

The methods of the invention have diverse application in addition to the design of new PKS genes. As but one illustrative example, the methods of the invention can be used to design methods to produce a desired compound. Organic molecules containing stereochemical centers are useful for a number of purposes, including use as synthetic or semi-synthetic intermediates. The preparation of such intermediates by organic synthesis can be extremely time consuming and expensive. An alternative source of such intermediates is via specific degradation of a polyketide, and the present invention provides computer-assisted means for designing such production methods.

Thus, certain functional groups of polyketides are susceptible to bond cleavage by specific chemical reactions that do not affect other functional groups. For example, carbon-carbon double bonds can be specifically cleaved by permanganate without affecting other functional groups normally in polyketides, such as ketones, alcohols, and lactones. Likewise, the Baeyer-Villager reaction converts a ketone to an ester (lactone) without affecting other groups of the aglycone. In accordance with the methods of the invention, one can assemble a library of polyketides in a database that can be addressed with a query describing a particular chemical reaction to generate all of the degradation products produced by that reaction upon each of the polyketides in the library. The degradation fragments thus generated serve as a library of the invention that can be sorted by properties, such as size, number and type of stereochemical centers, functional groups, or other factors, and searched for useful compounds. Moreover, the functional groups on the ends of the fragments generated (or at other locations) can also be converted to other functional groups by chemical reactions (optionally employing protecting groups on other functional groups), and the database of compounds can be expanded to include the compounds produced by such reactions.

From even a modest library of ~200 compounds, one can in this manner generate using the methods of the invention, two to three times as many valuable chemical intermediates. Once such an intermediate is identified, the organism that produces the polyketide from which the fragment is derived is fermented the polyketide isolated in bulk, the chemical reaction performed, and the desired degradation product(s) isolated and used. In this manner, the present invention makes available a wide variety of useful products otherwise unattainable.

Thus, the present invention has wide application in the fields of chemistry, particularly medicinal chemistry, molecular biology, and medicine. Those of skill in the art will recognize these and other benefits and applications provided by the present invention. Thus, the following examples are given for the purpose of illustrating the present invention and shall not be construed as being a limitation on the scope of the invention or claims.

EXAMPLE 1

The MORPH Program

This example provides the source code for an illustrative MORPH program of the invention. The MORPH program is a command line driven program that runs on a UNIX system. The program can be run from a shell script, such that the user fills in the entire command ahead of time, then post-processes the output file with UNIX utilities including sort, egrep, and uniq.

The command line appears as follows:

morph3-1 libraryfile-n targetname-t targetsequence [-x X-wildcards] [-y Y-wildcards] [-z Z-wildcards].

The library file is the name of the text file described below in Example 2. The target name is a user-defined identifier to distinguish this target from the library members (e.g., epothiloneD). The target sequence is a string of monomers that represent the CHUCKLES-encoded target polyketide (e.g., MEMLJDGE). Generally, if the target sequence is in the library, it is commented out from the library so that the morph program does not find the target itself. The three different wildcards, X, Y, and Z, are independent sets of monomers that can be included in the target sequence.

The output from the morph program can be redirected to a file. This output file is then post-processed by (1) extracting the HIT lines with valid combinations of modules that yield the target, (2) sorting the HITS based on alphanumeric content using the UNIX sort command, (3) running the UNIX uniq command which removes multiple copies of each HIT, leaving one copy of each, (4) sorting based on the number of pieces in the sequence of modules. Generally, the fewest number of pieces, which correspond to the fewest number of inter-modular interfaces, are desired; these will appear at the top of the output.

Below are some illustrative examples of calls to the MORPH program from a shell script using epothilone as a target. The first example generates combinations that yield epothilone D:

%morph3-1 PKS.lib-n epoD-t MEMLJDGE>omorph3_epoD
%egrep HIT omorph3_epoD | sort | uniq | sort+10-11>omorph3_epoD.uniq.sort The second example generates combinations that yield a derivative of epothilone D having a hydroxyl at C-13:

%morph3-1 PKS.lib-n epoD-13OH-t MEXLJDGE-x ABCD>oepoD-13OH
%egrep HIT oepoD-13OH | sort | uniq | sort+10-11>oepoD-13OH.uniq.sort The third example generates an epothilone having wildcards (set 1):

%morph3-1 PKS.lib-n epoD-set1-t MEXYZDGE-x ABCD-y LEFIN-z JACGM>oepoD-set1
% grep HIT oepoD-set1 | sort | uniq | sort+10-11>oepoD-set1.uniq.sort The fourth example generates an epothilone having another set of wildcards (set 2):

%morph3-1 PKS.lib-n epoD-set2-t MEXYZDgE-x JK-y EF-z JACGM>oepoD-set2
% grep HIT oepoD-set2 |sort |uniq |sort+10-11>oepoD-set2.uniq.sort MORPH in its current implementation operates at the monomer level and thus does not handle intra-modular modifications/splitting. Future implementations could convert the CHUCKLES-encoded strings into the corresponding and equivalent SMILES and then perform more complex chemical analysis of the PKS molecular graphs. Currently, inter-modular double bonds are present in the library, but are ignored by the program. These bonds can be introduced post-biosynthetically and the exact source is generally unknown.

The source code for MORPH is found in Appendix A (version 3.0) and B (version 4.0) (deposited in the microfiche appendix).

EXAMPLE 2

Illustrative Polyketide Library

This example provides the contents of an illustrative CHUCKLES encoded polyketide library. The first column provides the name of the polyketide; the second the CHUCKLES string; the third the annotated CHUCKLES string; and the fourth the source organism. Entries under annotated CHUCKLES and source organism are not complete for all of the polyketides.

| POLYKETIDE | CHUCKLES | annotated-CHUCKLES | SOURCE ORGANISM |
|---|---|---|---|
| 3-acetyl-4"-butyltylosin | FMNGODF | | |
| #aculeximycin | RRNRSMRSRSS SSRLSSN | RR(2-ethyl)NRSMRS(1-glycosyl)RSSS(2-hydroxyl)SR(1-glycosyl)LSSN(2-ethyl) | |
| albocycline-M1-ingramycin-TA2407-cineromycinB-U28010-SR2077 | BLME=JN | BLM(1,2-epoxy)E(1-methoxy)=J(2-hydroxyl)N | |
| albocycline-M2 | BLME=JN | B(2-hydroxyl)LME(1-methoxy)=J(2-hydroxyl)N | |
| albocycline-M3 | BSME=JL | BSME(1-methoxy)=J(2-hydroxyl)L | |
| albocycline-M5 | BSME=JN | BSME(1-methoxy)=J(2-hydroxyl)N | |
| albocycline-M6 | BLME=JL | BL(2-hydroxyl)ME(1-methoxy)=J(2-hydroxyl)L | |
| albocycline-M7 | BLME=JN | BL(2-hydroxyl)ME(1-methoxy)=J(2-hydroxyl)N | |
| albocycline-M8 | BLME=Q | BLME(1-methoxy)=Q | |
| aldgamycin | BMLGJDL | B(1-cyc)MLG(2-hydroxyl)JDL(2-cyc) | |
| amphotericinA | CDNNLNNNF CEFEALEE | CDNNLNNNNF(1-glycosyl)C(1-O-cyc,2-carboxylicacid)EF(1-cyc)EALEE | |
| #amphotericinB | CDNNNNNNF QQQEELEE | CDNNNNNNNF(1-glycosyl)C(1-O-cyc,2-carboxylicacid)EF(1-cyc)EALEE | |
| angiolam | NMFJNSJIQLGAm | | |
| aplyronineA | BFJCENFFMEK AFNN | B(1-C(=O)C)F(1-C(=O)C(C)N(C)C)JCENFFME(1-methoxy)KAF(1-C(=O)C(N(C)C)COC)NN | sea hare *Aplysia kurodai* |
| apoptolidin | EFLMNAMMM | EF(methoxy-1,hydroxy-2)LMNAMMM | |
| aurachinB | MLMLM | MLMLM | |
| aurachinC | MLMLM | MLMLM | |
| A59770 | QQKQQLJFCDN | QQK(2-ethyl)Q=QLJ(2-hydroxyl)F(2-O-glycosyl)CD(2-hydroxyl)N | *Amycolatopsis orientalis* |
| A82548A-cytovaricin | QQQKQNLJFDDN | | |
| A83543A | FLFQQQ | FLFQQQ | *Saccharopolyspora spinosa* |

| POLYKETIDE | CHUCKLES | annotated-CHUCKLES | SOURCE ORGANISM |
|---|---|---|---|
| AB023a | NNNNNRSSSLSR | NNNNNRSSSLSR | |
| AH-758 | RSNMURMN | RS(2-methoxy)NMURMN(2-methoxy) | |
| bafilomcinD | BNHCENMKCMN | BNHCE(1-macrocyc,2-methoxy)NMKCMN(2-methoxy)Q(keto-macrocyc) | S. sp. |
| bafilomycinA1 | BNHCENMKCMN | BNHCE(1-macrocyc,2-methoxy)NMKCMN(2-methoxy)Q(keto-macrocyc) | |
| borrelidin | SNMRUUUS | SNM(2-N)RUUUS | |
| calyculin | QFBBMmNm | QF(1-methoxy)BBMmNm | Discodermia calyx |
| candicidin-candeptin-ascosin-levorin-etc | CDNNNNNNNFCEELIEE | CDNNNNNNNF(1-glycosyl)C(1-O-cyc,2-carboxylicacid)EE(1-cyc)E(2-hydroxyl)LIEE | S. griseus, S. canescus, S. levoris, S. viridoflavus, Stv. grisoviridum |
| candidin | QDNNNNNNNFCEFELIEE | RDNNNNNNNF(1-glycosyl)C(1-O-cyc,2-carboxylicacid)EF(1-cyc)E(2-hydroxyl)LIEE | |
| carbomycin | ENNCODF | EN(1,2-epoxy)NHOF(1-glycosyl,2-methoxy)F(1-C(=O)C) | |
| carbomycinB-magnamycinB | FNNGOFF | FNNGOF(1-glycosyl,2-methoxy)F(1-C(=O)C) | |
| carbomycin-A-magnamycin-deltamycinA4-NSC51001-P597-3628-WC3628 | ENNHOFF | ENNHO(includes CCHO)FF | |
| chalcomycin-myconomycin-aldgamycinDmikonomycin | BNNGKDN | B(2-O-glycosyl)N(1,2-epoxy)NG(2-hydroxyl)KD(1-glycosyl)N | S. bikiniensis, S. albogriseolus |
| chimeramycinB-PTL448 | BMNCODF | B(O-ethyl)MNC(1-glycosyl)OD(1-glycosyl)F | S. ambofaciens ka-448 |
| chivosazolA | SRRnNNSRQNnRMnNn | SRR(1-O-macrocyc)nNNSR(1-methoxy)QNnR(1-glycosyl)MnNnQ(keto-macrocyc) | S. cellulosum |
| cineromycinB | BLME=JN | BLME=J(2-hydroxyl)N | S. cinereochromogenes, S. sp. |
| cineromycinBdehyro | BLMI=JN | BLMI=J(2-hydroxyl)N | S. grieoviridis |
| cineromycinB2,3dihyro | BLME=JL | BLME=J(2-hydroxyl)L | S. grieoviridis |
| cirramycinB1dihydroxy-A6888X | BMNGODF | BM(1,2-epoxy)NGOD(1-glycosyl)F | S. flocculus |
| cirramycinB-cirramycinB1-Acumycin-A688A-B58941-A6888A | AMNGODF | AM(1,2-epoxy)NGOD(1-glycosyl)F | S. cirratius, S. griseoflavus, S. fradiae, S. flocculus |
| cladospolideA | ELLFN | ELLF(2-hydroxyl)N | Cladosporium fulvum, C. cladosporiodes |
| cladospolideB | ELLFn | ELLF(2-hydroxyl)n | Cladosporium fulvum, C. cladosporiodes |
| cladospolideC | ELLEN | ELLE(2-hydroxyl)N | fungus Cladosporium tenuissimum |
| concanamycinA-folimycin-A661-1-S45A-TAN1323B-X4357B | CENMKCCMN | CE(2-methoxy)NMKC(2-ethyl)CMN(2-methoxy) | S diastatochromogenese, S. sp, S. neyagawaensis |
| concanamycinB-S45B | CENMKCCMN | CE(2-methoxy)NMKCCMN(2-methoxy) | S diastatochromogenese |
| concanamycinG-anhydroconcanamycinB | NBNHCENMKCCMN | NBNHCE(2-methoxy)NMKCCMN(2-methoxy) | |
| congloblatin | AJM | A(1-oxazoyl)JM.AJM | |
| #copiamycin | RNRSSSSSSRLRSRN | RNRSSSS(1-O-cyc)S(2-hydroxyl)S(1-cyc)RLRSRN | S. hygroscopicus |
| cytovaricin-H230 | QQQKQNLJFCDN | QQQKQNLJ(2-hydroxyl)F(2-O-glycosyl)CD(2-hydroxyl)N | S. sp., S. collinus |
| cytovaricinB | QQKQNLJFDDN | QQQKQNLJ(2-hydroxyl)F(2-O-glycosyl)CD(2-hydroxyl)N | S. torulosus |

-continued

| POLYKETIDE | CHUCKLES | annotated-CHUCKLES | SOURCE ORGANISM |
|---|---|---|---|
| CP64537 | ARGKDD | A(2-glycosyl)R(1-C(=O)C(O)C(C)C)G(2-hydroxyl)KDD(1-glycosyl) | *Streptomyces toyocaensis humicola* ATCC 39491 |
| damavaricinC | QDQCCNM | QDQCCNM | *S. spectabilis* |
| deltamycinA1 | ENNGOFF | EN(1,2-epoxy)NGOF(1-glycosyl,2-methoxy)F(1-C(=O)C) | *S. deltae, S. halstedii-deltae* |
| deltamycinX-desisovalerylcarbomycinA | ENNGOFF | EN(1,2-epoxy)NGOF(1-glycosyl,2-methoxy)F(1-C(=O)C) | *S. deltae, S. halstedii-deltae* |
| engleromycin | QNJHN | QNJH(2-hydroxyl)N(1,2-epoxy) | *Engleromyces goetzei* |
| #epothilone | MEMLJDgE | MEM(1,2-epoxy)LJDG(2-methyl)E | |
| erythromycin | ADGJDD | A(2-hydroxyl)DGJ(2-hydroxyl)D(1-glycosyl)D(1-glycosyl) | |
| espinomycinA2 | ENNCOFF | ENNCOF(1-glycosyl,2-methoxy)F(1-C(=O)C) | *S. fungicidicus* |
| filipinIII-lagosin14deoxy | ENNNNMEFFFFFFFL | E(2-hydroxyl)NNNNMEFFFFFFF | *S. filipinensis, S. durhamensis* |
| filipin-lagosin | ENNNNMEFFFFFFF | | *S. filipinensis, S. durhamensis* |
| formamicin | CBNMOCMN | CBNMO(includes a long, branched alkyl chain)CMN | |
| foromacidinB-spiramycinII-spiramycinB | ENNAOFF | | *S. ambofaciens* |
| FD891 | RRUSNNLNRMM | RRUS(1-O-macrocyc)NNL(2-hydroxyl)N(1,2-epoxy)RMMQ(keto-macrocyc) | *S. graminofaciens* |
| FK895 | RNRNMRNRLS | R(1-methoxy)N(1,2-epoxy)RNMR(1-O-macrocyc)NR(1-C(=O)C,2-hydroxyl)LSQ(keto-macrocyc) | *S. hygroscopicus* |
| FK-506 | MAEPMJJBKQQ | | |
| gedamycin | IEJBNNNnNNNFAEFEEEEIE | IEJBNNNnNNNF(1-glycosyl)A(1-O-cyc,2-carboxylicacid)EF(2-cyc)EEEEIE | *S. aureofaciens* |
| geldanamycin | QULRMRnM | QUL(2-methoxy)RMS(1-CONH2,2-methoxy)nM | *S. hygroscopicus* var. *gelanus* |
| gephyronicacid | RRTSRRM | | |
| gloeosporone | ELLEIL | ELLE(1-O-cyc)I(2-cyc,2-hydroxyl)L | *Colletotrichum gloeosporioides* f. sp. *jussiaea* |
| GERI-155 | BNLGJDN | B(2-O-glycosyl)N(1,2-epoxy)LG(2-hydroxyl)JD(1-glycosyl)N | *S.* GERI-155 |
| halomicin | QNCRCBNM | QNC(1-methoxy)R(1-C(=O)C)CBNM | *Mic. halophytica* |
| herbimycin | ALDMFnM | A(1-methoxy)L(2-methoxy)D(1-methoxy)MF(1-CONH2,2-methoxy)nM | |
| hygrolidin | CENMJCMM | CE(1-O-macrocyc,2-methoxy)NMJCMMQ(keto-macrocyc) | *S. hygroscopicus* |
| hygrolidin-oxo | BNHCENMJCMN | BNHCE(1-O-macrocyc,2-methoxy)NMJCMN(2-methoxy)Q(keto-macrocyc) | *S. griseus, S. hygroscopicus* |
| irumamycin | URRNSLMQQS | UR(1-O-macrocyc)RNS(1-glycosyl)LMR(1-O-cyc)=QS(2-cyc)Q(keto-macrocyc) | |
| juvenimicinA1-T1124A1-M4365A1 | BMNGFDF | BMNGFDF(includes an ethyl in pos 2) | *Mic. chalcea* |
| juvenimicinA2-T1124A2-M4365A2 | BMNGJDF | | *Mic. chalcea* |
| juvenimicinA4-T1124A4-M4365A4 | BMNGODF | | *Mic. chalcea-Mic. capillata* |
| juvenimicin-T1124 | BNNGJDF | | *Mic. chalcea* |
| kanchanamycin | NMSSSSSSRLRSRNN | | |
| lankamycin-kujimycin-landavamycin-A20338N2 | ADGJDD | | *S. violaceoniger, S. spinichromogenes* |
| leinamycin | QNNIMLN | | |
| leucanicidin | CENMKCMN | CE(2-methoxy)NMKCMN(2-methoxy) | *S. halstedii* |

-continued

| POLYKETIDE | CHUCKLES | annotated-CHUCKLES | SOURCE ORGANISM |
|---|---|---|---|
| leucomycinA12-kitasomycinA12 | FNNCODF | | S. kitasatoensis |
| leucomycinA14-kitasomycinA14 | FnNCOFF | | S. kitasatoensis |
| leucomycinA3-josamycin-platenomycinA3-turimycinA5 | ENNAODF | | S. kitasatoensis, S. hydroscopicus, S. narbonensis, S. platensis |
| leucomycinA5-turimcinH4 | ENNCOFF | | S. kitasatoensis |
| lienomycin | SSSNSSSTSMLNRRNNNNNL | | |
| lucensomycin-etruscomycin-lucimycin-FJ1163-butylpimaricin | SNNNNSREEFN | | Act. sp, S. lucensis, S. glaucus |
| L155175 L681110 | RSNMURmMNMURMN | RS(2-methoxy)NMURmMNMURMN(2-methoxy) | |
| macrocin-lactenocin | BMNHODF | | S. aureus, S. lutea, K. pneum, B. subtl., Shva.. |
| macrocin-YO7625 | QMNGODF | | S. fradiae gs 16 |
| maridomycinI | ENNCOFF | | S. paltensis, S. rimosius, S. capuensis, S. racemochromogenes |
| maridomycin-platenomycinC3-turimycinEP5-B5050A-YL704-C-3 | ENNCJDF | | S. hygroscopicus-S. platensis-malvinus |
| mathemycinA | RSSRSSRSSRRMRMRNLRL | | |
| midecamycinA1-platenomycinB1-SF837 | ENNCOFF | ENNCOF(2-methoxy)F | S. mycarofaciens |
| midecamycinA2-mydecamycinA2-SF837A2 | FNNDJEE | FNNDJE(2-hydroxy)E(1-C(=O)CC) | S. mycarofaciens |
| milbemycin | QQQMKNQQ | | |
| #monazomycin | SSRRSSURNSRSMRMRNLRSLL | | |
| mycinamicin | BNNGJDN | B(1-cyc)NNGJDN(2-cyc) | |
| mycinamicinVI | BNNGJDN | | Micromonospora griseorubida sp. |
| mycinamicinX11 | BNNGLDN | | S. aureus, S. pyogenes, Corynebacterium |
| #mycolactone | SRMUSMSSL.sSMNMMN | SRMUSMSSL.sSMNMMN | |
| mycolactoneA mycolactoneB | SRMUSMSSLsSMNMMN | SRMUSMSSLsSMNMMN | |
| myxovirescinA1 | QQEFLNNLLILKJ | | |
| myxovirescinA2 | QQEFLNNLLILJJ | | |
| myxovirescinB-megovalicinB | QQEFLNNLLILKM | | |
| myxovirescinC-C1 | QQEFLNNLLLLKJ | | |
| myxovirescinD | QQEFLNNLLLLKM | | |
| myxovirescinE | QQEFLNNLLILJ | | |
| myxovirescinF1 | QQEFLNNLLLLKJ | | |
| myxovirescinF2 | QQEFLNNLLLLJJ | | |
| myxovirescinG1 | QQEFLNNLLLKJ | | |
| myxovirescinG2 | QQEFLNNLLLJJ | | |
| myxovirescinH1 | QQEFLNNLLILKJ | | |
| myxovirescinH2 | QQEFLNNLLILJJ | | |

| POLYKETIDE | CHUCKLES | annotated-CHUCKLES | SOURCE ORGANISM |
|---|---|---|---|
| myxovirescinL | QQEFLNNLLILHJ | | |
| myxovirescinP1 | QQEFLNNLLILLKJ | | |
| myxovirescinP2 | QQEFLNNLLILLJJ | | |
| myxovirescinQ | QQEFLNNLLILKM | | |
| myxovirescinS | QQEFLNNLLILHJ | | |
| M4365G2 | BMNGODF | | *Streptoverticillum kitasatoensis, S. thermaotolerans* |
| nancimycin | QNDACBNM | | *S. albovinaceus* |
| neocopiamycin | NRSSSSSRLRSRN | | |
| niddamycin-F3463-3desacetylcarbomycinB | FNNGOFF | FNNGOF(1-glycosyl,2-methoxy)F | *S. aureus, S. lutea, B. subt* |
| oligomycinA | QJNNJRGAGAN | | *diastatochromogenes, S. chibaensis* |
| oligomycinB | QJNNKCHDHDN | | *S. diastatochromogenes* |
| oligomycinB-44homo | QJNNJRGRGAN | | *S. bottropensis* |
| oligomycinD | QJNNJBGAGAN | | *S. arabicus, S. parvulus, S. rutgersensis, S. griseus, S. aureofaciens* |
| ossamycin | QQQNLLKFDDN | | |
| perimycin | JBNNNnNNNFCEFEEEEIE | JBNNNnNNNFCEFEEEEIE | |
| phenalamid | nCNNNNM | | |
| phenalamideA1-fenalamid-I-102-C | JMCMNnNM | | |
| phenalamideA2-102-T | JMCMNNNM | | |
| phenalamideA3 | JMCMNNnM | | |
| phenalamideB | JMCMNnNM | | |
| phenalamideC | JMCMNNNM | | |
| phthoramycin | QQNLUSRRN | | |
| pikromycin | ANGJDH | | |
| prasinon-L155175 | DNMJCMM | | *S. hydroscopicus ma 5285; S. prasinus* |
| protostreptovaricin | QDACDNM | | |
| PD118576A2 | ENMJCMN | | *S. sp. wp 3913* |
| PF1163 | EJLLQ | | |
| #quinolidomicin | SSLULSSNNNSISNNSSSUSRRQQRRSS | | |
| rapamycin | FGMEGJNNMEEKQQ | | |
| rhizopodin | RLQSNNSS | | |
| rifamycin | QQQNDACBNM | | |
| rimocidin | BNNNNFCEFELIA | | |
| rosamicin-repromicin | BMNGODF | | |
| rosaramycin | BMNGODF | | *Micromonospora rosaria* |
| rustmicin | QQQJMOG | QQQJMO(includes COH)G | |
| rutamycin | QQJNNJBGAGAN | | |
| scytohycin | BFCEENQEMN | | |
| scytohycinB-E | BFCEQNQEMN | | |
| shurimycin | NNRSSSSSSRLRSRNN | | |
| sorangicin | LKMFnENLNCFDFNQNNnn | LKMF(2-hydroxyl)nENLNCFDFNQNNnn | |
| sorangicinA | QNLNF | | |
| sorangicinB | NLNF | | |

-continued

| POLYKETIDE | CHUCKLES | annotated-CHUCKLES | SOURCE ORGANISM |
|---|---|---|---|
| sorangolideA | LLLLKBLJMEAFM | | myxobacterium sorangium cellulosum |
| soraphen | ELJFJDFA | | |
| spiramycin | nNCJPF | | |
| staphcoccomycin-angolamycin-shincomycin | CMNGODF | | |
| stipiamide | JMCNNnNM | | |
| tartrolonB2 | nNLFHE | nNLFHE | fragment |
| tedanolide | JGEHMDHF | JGEHMDHF(2-hydroxyl) | |
| thiazinotrienomycin | QLmRSNNNS | | |
| tiacumicin | SMMRMSNM | | |
| tylosinC-macrocin | EMNHODF | | |
| tylosin-A | EMNGODF | | |
| TAN-1323 | NMURRMM | | |
| TMC-34 | NRSSSSSSRLRSRN | | |
| venturicidinA | CKNFLMQQQ | | |
| vicenistatin | LNMULRNN | | |
| viranamycinB-virustomycin-TAN1323C | QNMKCCMN | | S. sp. ch41 |
| zincophorin-griseochelin | KMCNLACC | | S. griseus |

In another embodiment, the polyketide library includes the name of the polyketide, the CHUCKLES string and a linearized representation of the structure. The linearized representations of the CHUCKLES structures for erythromycin and epothilone are as follows:

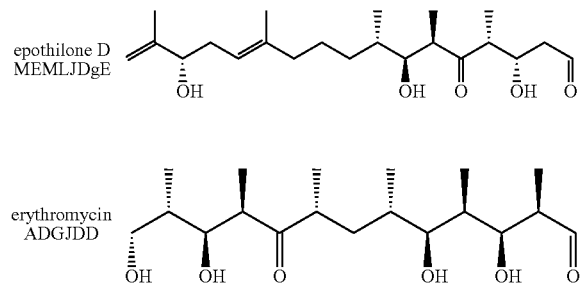

An illustrative example of a polyketide library containing linearized representations of their structures is found in Appendix C (deposited in the microfiche appendix).

EXAMPLE 3

Alternative PKS Genes for Epothilone

This example illustrates the alignment and design of novel PKS genes for the target epothilone. Epothilone is first converted into CHUCKLES string format and then read into the MORPH program as a TARGET. The program then generates all possible alignments of library modules and sorts the alignments to determine preferred combinations of modules for gene construction and production of epothilone via a novel polyketide synthase gene.

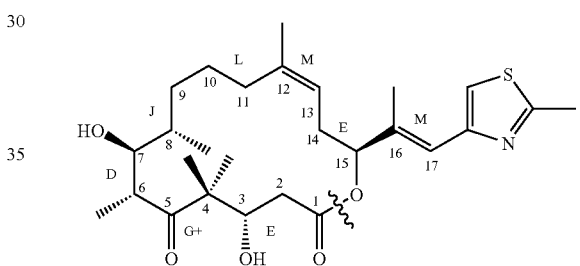

The epothilone D structure above was first opened at the macrolactone ring closure between the C-1-ketone and the C-15-oxygen. The monomer set shown in FIG. 2 was then matched against each of the successive pairs of macrocyclic backbone carbon atoms, starting with C-2 and C-3, which match monomer E. The next two carbon atoms C-4 and C-5 match monomer G with an additional post-synthetic methylation on C-4. C-6 and C-7 match monomer D. C-8 and C-9 match monomer J. C-10 and C-11 match monomer L. C-12 and C-13 match monomer M. C-14 and C-15, where C-15 has a hydroxyl substitution (modified by thioesterase to close the macrocycle), match monomer E. C-16 and C-17 match monomer M.

The rest of the molecule, a methyl-substituted thiazole moiety, does not match any of the monomers in the monomer set. This moiety corresponds to a malonyl CoA loading module and an NRPS module that together generate the methyl-substituted thiazole moiety. This moiety is thus omitted from the CHUCKLES string generated from this illustrative monomer set but can be added simply by adding a monomer to the set. The CHUCKLES string generated is EGDJLMEM, which is in the reverse order of biosynthesis. This sequence is then reversed to MEMLJDGE to yield a monomer sequence that matches the order of biosynthesis. The sequence is then annotated to account for the post-synthetic modifications as follows MEMLJDG (2-methyl)E.

This target sequence is provided to the MORPH program to generate all possible combinations of modules in the CHUCKLES-encoded library that will yield the target CHUCKLES. The valid combinations are then sorted in increasing order of non-native inter-module interfaces. In one implementation, a MORPH run generated 3,452 valid sequences of five inter-module interfaces. Of these, none contain fewer than five inter-module interfaces. Some illustrative sample module combinations appear below. The combinations are shown listing each monomer followed by a colon and the name of the polyketide(s) from which it is derived, followed by a parenthetical showing the associated monomers in that polyketide. Vertical lines represent modular junctions between two different polyketides.

Illustrative PKS Gene 1:

M:3acetyl4"butylrlyltylosin(FMN) | E:tedanolide(GEH) | M:aldgamycin(BML) L:aldgamycin(MLG) | J:aldgamycin (GJD) D:aldgamycin(JDL) | G:tedanolide(JGE) E:tedanolide(GEH)

Illustrative PKS Gene 1 thus comprises one or more open reading frames that encode, in the order listed, the module from the acetyl-4"-butyryltylosin PKS that corresponds to monomer M, the module from the tedeanolide PKS corresponding to monomer E, the modules from the aldgamycin PKS corresponding to monomers M, L, J, and D, and the modules from the tedanolide PKS corresponding to monomers G and E.

Illustrative PKS Gene 2:

M:albocycline-M1-ingramycin-TA407-cineromycinB-U28010-SR077(LME) E:albocycline-M1-ingramycin-TA2407-cineromycinB-U28010-SR2077(MEJ) | M:albocycline-M1-ingramycin-TA2407-cineromycinB-U28010-SR2077(LME) | L:albocycline-M1-ingramycin-TA2407-cineromycinB-U28010-SR2077 (BLM) | J:erythromycin (GJD) D:erythromycin(JDD) | G:tedanolide(JGE) E:tedanolide(GEH)

EXAMPLE 4

Alternative PKS Genes for 6-Deoxervthronolide B

This example illustrates the alignment and design of novel PKS genes for the erythromycin basic polyketide structure (6-dEB) using the MORPH program.

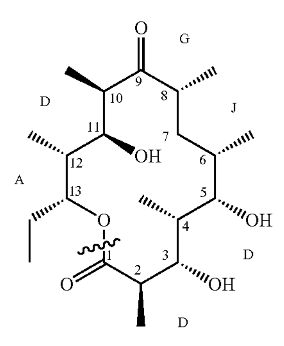

For the 6-dEB structure above, the CHUCKLES string is generated by first opening the macrolactone ring closure between the C-1-ketone and the C-13-oxygen. Using the monomer set and matching protocol described in Example 3, one generates the CHUCKLES string DDJGDA, in the reverse order of biosynthesis. This sequence is then reversed to ADGJDD to yield the monomer sequence that matches the order of biosynthesis. The sequence is then annotated to account for the post-synthetic modifications (erythromycin A) as follows A(Z-hydroxyl) DGJ(2-hydroxyl)D(1-glycosyl) D(1-glycosyl).

This target sequence is supplied to the MORPH program to generate all possible combinations of modules in the CHUCKLES-encoded library. The valid combinations are then sorted in increasing order of non-native inter-module interfaces. In one implementation, a MORPH run generated 19,631 valid sequences of less than or equal to five inter-module interfaces. Of these, 13,306 contain 4 inter-module interfaces, and 256 contain only 3 inter-module interfaces. Some of these contain only two inter-module faces, and one only contains one. Some illustrative sample module combinations follow.

Illustrative PKS Gene 1:

A:amphotericinA(EAL) | D:aldgamycin(JDL) | G:mycinamicin(NGJ)

J:mycinamicin(GJD) D:mycinamicin(JDN) | D:amphotericinA(CDN)

Illustrative PKS gene 1 thus comprises one or more open reading frames that encode, in the order listed, the amphotericin PKS module corresponding to monomer A, the aldgamycin PKS monomer corresponding to monomer D, the mycinamicin PKS modules corresponding to monomers G, J, and D, and the amphotericin PKS module corresponding to monomer D.

Illustrative PKS Gene 2:

A:amphotericinA(EAL) D:aldgamycin(JDL) | G:pikromycin (NGJ) J:pikromycin(GJD) D:pikromycin(JDH) | D:aldgamycin(JDL)

Illustrative PKS Gene3:

A:lankamycin-kujimycin-landavamycin-A20338N2(-AD) D:lankamycin-kujimycin-landavamycin-A20338N2 (ADG) G:lankamycin-kujimycin-landavamycin-A20338N2 (DGJ) J:lankamycin-kujimycin-landavamycin-A20338N2 (GJD) | D:ossamycin(FDD) D:ossamycin(DDN)

Illustrative PKS Gene 4:

A:amphotericinA(EAL) | D:lankamycin-kujimycin-landavamycin-A20338N2(ADG) G:lankamycin-kujimycin-landavamycin-A20338N2(DGJ) J:lankamycin-kujimycin-landavamycin-A20338N2(GJD) | D:A82548A-cytovaricin(FDD) D:A82548A-cytovaricin(DDN)

Illustrative PKS Gene 5:

A:lankamycin-kujimycin-landavamycin-A20338N2(-AD)
D:lankamycin-kujimycin-landavamycin-A20338N2(ADG)
G:lankamycin-kujimycin-landavamycin-A20338N2(DGJ)
J:lankamycin-kujimycin-landavamycin-A20338N2(GJD)
D:lankamycin-kujimycin-landavamycin-A20338N2(JDD)
D:lankamycin-kujimycin-landavamycin-A20338N2(DD-)

Thus, the present invention provides a useful means to generate new PKS genes and corresponding enzymes to produce polyketides. The invention having now been described by way of written description and examples, those of skill in the art will recognize that the invention can be practiced in a variety of embodiments and that the foregoing description and examples are for purposes of illustration and not limitation of the following claims.

What is claimed is:

1. A method of designing and producing a polyketide synthase (PKS) gene, which method comprises:

(a) defining the structure of a desired polyketide by a first string of alphanumeric symbols, wherein each symbol in the first string represents a monomer unit of the desired polyketide, (b) comparing the first string of alphanumeric symbols to a second string of alphanumeric symbols from a database, wherein the database comprises at least one second string of alphanumeric symbols representing a known polyketide, and wherein each alphanumeric symbol in the second string represents a monomer unit of the known polyketide, (c) identifying a common alphanumeric symbol or continuous sequence of alphanumeric symbols in said first and second strings, (d) generating a third string, wherein the third string comprises the name of the known polyketide and the common alphanumeric symbol or continuous sequence of alphanumeric symbols identified from step (c), and wherein the third string represents the structure of a PKS gene encoding a PKS enzyme capable of producing the desired polyketide, (e) storing or displaying the third string, and (f) using the third string to produce the PKS gene; or wherein steps (b) and (c) are repeated.

2. The method of claim 1, wherein more than one third string of alphanumeric symbols is generated and displayed.

3. The method of claim 2, wherein the third strings that are generated are rated in an order based on one or more parameters.

4. The method of claim 3, wherein the parameters are selected from the group consisting of non-native polyketide module interfaces and non-native polyketide protein interfaces.

5. The method of claim 1, wherein the PKS gene is designed using a physical computer-readable medium embodying a set of program instructions configured to enable a computing device to perform the method steps for designing the PKS gene encoding a PKS enzyme capable of producing the desired polyketide.

6. The method of claim 1, wherein more than one third string is generated and stored.

7. The method of claim 6, wherein the third strings that are generated are rated in an order based on one or more parameters.

8. The method of claim 7, wherein the parameters are selected from the group consisting of non-native polyketide module interfaces and non-native polyketide protein interfaces.

9. A physical computer-readable medium embodying a set of program instructions configured to enable a computing device to perform the method steps of claim 1.

10. A computer assisted method for designing and producing a polyketide synthase (PKS) gene, comprising:

(a) receiving a first string of alphanumeric symbols representing the structure of a desired polyketide, wherein each symbol in the first string represents a monomer unit of the desired polyketide, (b) comparing the first string of alphanumeric symbols to a second string of alphanumeric symbols from a database, wherein the database comprises at least one second string of alphanumeric symbols representing a known polyketide, and wherein each alphanumeric symbol in the second string represents a monomer unit of the known polyketide, (c) identifying a common alphanumeric symbol or continuous sequence of alphanumeric symbols in said first and second strings, (d) generating a third string, wherein the third string consists of a the name of the known polyketide and the common alphanumeric symbol or continuous sequence of alphanumeric symbols identified from step (c), and wherein the third string represents the structure of a PKS gene encoding a PKS enzyme capable of producing the desired polyketide, (e) storing or displaying the third string, and (f) using the third string to produce the PKS gene; or wherein steps (b) and (c) are repeated.

11. A PKS gene designed and produced by the method of claim 1.

12. A PKS gene designed and produced by the method of claim 5.

13. A PKS gene designed and produced by the method of claim 10.

14. A PKS gene designed and produced by the method of claim 9.

* * * * *

UNITED STATES PATENT AND TRADEMARK OFFICE
CERTIFICATE OF CORRECTION

PATENT NO.          : 7,680,601 B1                                            Page 1 of 1
APPLICATION NO.     : 09/867845
DATED               : March 16, 2010
INVENTOR(S)         : Ralph Reid et al.

It is certified that error appears in the above-identified patent and that said Letters Patent is hereby corrected as shown below:

Column 30, Line 25

Claim 10 (d) second line:

After "of" delete "a"

Signed and Sealed this

Seventh Day of September, 2010

David J. Kappos
*Director of the United States Patent and Trademark Office*